(12) United States Patent
Ueda et al.

(10) Patent No.: US 6,420,367 B1
(45) Date of Patent: Jul. 16, 2002

(54) PYRIMIDINE DERIVATIVES EXHIBITING ANTITUMOR ACTIVITY

(75) Inventors: Kazuo Ueda, Koka-gun; Hidekazu Tanaka; Hideyuki Takenaka, both of Osaka, all of (JP)

(73) Assignee: Shionogo & Co., Ltd., Osaka (JP)

( * ) Notice: Subject to any disclaimer, the term of this patent is extended or adjusted under 35 U.S.C. 154(b) by 0 days.

(21) Appl. No.: 09/743,721

(22) PCT Filed: Jul. 16, 1999

(86) PCT No.: PCT/JP99/03863

§ 371 (c)(1),
(2), (4) Date: Jan. 16, 2001

(87) PCT Pub. No.: WO00/04014

PCT Pub. Date: Jan. 27, 2000

(30) Foreign Application Priority Data

Jul. 16, 1998 (JP) ............................................ 10-201423
Apr. 19, 1999 (JP) ............................................ 11-110320

(51) Int. Cl.⁷ .................... A61K 31/505; C07D 419/00
(52) U.S. Cl. ........................................ 514/256; 544/328
(58) Field of Search ............................ 514/256; 544/328

(56) References Cited

FOREIGN PATENT DOCUMENTS

JP          61-57587      *  3/1986
JP          8-504215         5/1996

* cited by examiner

*Primary Examiner*—Mukund J. Shah
*Assistant Examiner*—Tamthom N. Truong
(74) *Attorney, Agent, or Firm*—Birch, Stewart, Kolasch & Birch, LLP

(57) ABSTRACT

A compound represented by the formula (I):

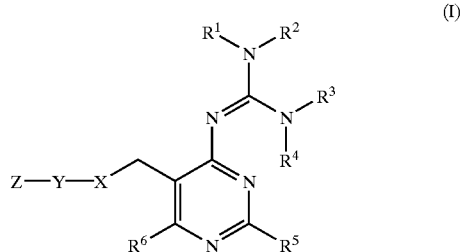

wherein, for example, $R^1$, $R^2$, $R^3$, and $R^4$ are each independently hydrogen atom, alky, and the like, $R^5$ and $R^6$ are each independently hydrogen atom, alkyl, and the like, X is —O—, —S—, and the like, Y is 5-membered heteroaryl-diyl and the like, Z is optionally substituted aryl and the like, the prodrugs thereof, or their pharmaceutically acceptable salts, or their solvates.

13 Claims, No Drawings

PYRIMIDINE DERIVATIVES EXHIBITING ANTITUMOR ACTIVITY

This application is the national phase under 35 U.S.C. §371 of PCT International Application No. PCT/JP99/03863 which has an International filing date of Jul. 16, 1999, which designated the United States of America.

TECHNICAL FIELD

The present invention relates to a novel pyrimidine derivative having an antitumor activity, a cytostatic activity, and an inhibitory activity against a signal derived from Ras oncogene products.

BACKGROUND ART

The oncogene "ras" such as H-ras, K-ras, and N-ras is mutated and activated in many of neoplasms. The "Ras", the products of ras oncogene, strongly concerns tumorigenesis caused by acceleration of cell cycle and induction of expression of many of genes associated with a malignant conversion such as a vascular endothelial growth factor and type-IV coliagenase. Especially, it is found that there is highly frequent ras mutation in solid tumor such as pancreatic cancer (>80%), colon cancer (>40%), and lung cancer (>20%) which are difficult to be cured by using existing chemotherapeutics. Therefore, it is considered that Ras is one of the most important target molecules in the development of the chemotherapeutics against them.

A farnesyl-protein-transferase (FPT) inhibitor (FPTI) is known as chemotherapeutics of which target are Ras (WO95/13059, WO95/25086, WO95/25092, WO95134535, U.S. Pat. No. 5,608,067, and JP-A-7-112930).

In the cells expressing activated Ras, the excess signals reach cell nucleus through some signaling pathways and some signal transmitter molecules such as MAPK (Mitogen Activated Protein Kinase) and P13K (Phosphatidylinositol-3-Kinase). The signals activate the transcription factors such as AP1 (Activator Protein-1) and ETS (E26 transformation specific) in the cell nucleus and then they induce the expression of many genes related to malignant features through transcription activation element such as Ras Responsive Element (RRE). Therefore, it is possible to repress the malignant conversion of the cancer cells, when the signal transmission (a signal derived from ras oncogene products) is inhibited.

DISCLOSURE OF INVENTION

In the above situation, the inventors of the present invention have studied on the antitumor agent having an inhibitory activity against a signal derived from Ras oncogene products.

The activation of gene expression through RRE is in proportion to a signal derived from Ras and the signal can be measured by the amount of its expression. The inventors of the present invention artificially made cells having activated Ras wherein expression of firefly luciferase gene, reporter gene, is regulated by RRE and carried out a screening of the inhibitors taking luciferase activity shown by the cells as an index of signals through Ras. As a result, the inventors of the present invention found that a series of pyrimidine derivatives have a strong inhibitory activity against a signal derived from Ras oncogene products.

The present invention relates to I) a compound represented by the formula (I):

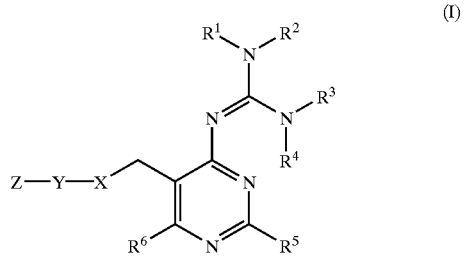

wherein $R^1$, $R^2$, $R^3$, and $R^4$ are each independently hydrogen atom, optionally substituted alky, optionally substituted alkenyl, optionally substituted alkynyl, optionally substituted aryl, optionally substituted heteroaryl, optionally substituted aralkyl, an optionally substituted non-aromatic heterocyclic group, or acyl; or $R^1$ and $R^2$, $R^3$ and $R^4$, and $R^2$ and $R^3$ each taken together with the adjacent nitrogen atom form the same or different 3- to 6-membered ring optionally containing O, S, or N, provided that $R^1$ and $R^2$ and $R^3$ and $R^4$ do not form a ring when $R^2$ and $R^3$ taken together form a ring;

$R^5$ and $R^6$ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl, optionally substituted heteroaryl, optionally substituted aryl alkenyl, or optionally substituted alkenyl; the prodrugs thereof, or their pharmaceutically acceptable salts, or their solvates.

In more detail, the present invention relates to:

II) a compound represented by the formula (II):

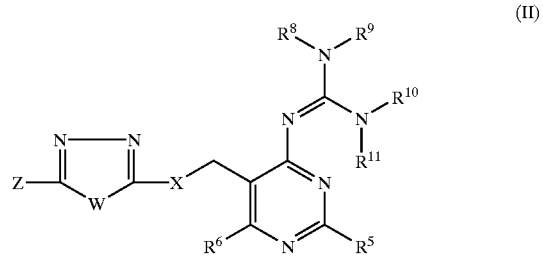

wherein $R^8$, $R^9$, $R^{10}$, and $R^{11}$ are each independently hydrogen atom, optionally substituted alkyl, alkenyl, alkynyl, optionally substituted aryl, optionally substituted heteroaryl, optionally substituted aralkyl, a non-aromatic heterocyclic group, or acyl;

W is —O—, —S—, or —N($R^4$)— wherein $R^4$ is hydrogen atom or optionally substituted alkyl;

$R^5$, $R^6$, X, and Z are as defined above, the prodrugs thereof, or their pharmaceutically acceptable salts, or their solvates, III) a compound represented by the formula (III):

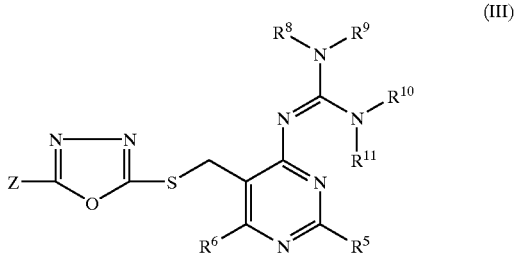

wherein $R^5$, $R^6$, $R^8$, $R^9$, $R^{10}$, $R^{11}$, and Z are as defined above, the prodrugs thereof, or their pharmaceutically acceptable salts, or their solvates, IV) a compound represented by the formula (IV):

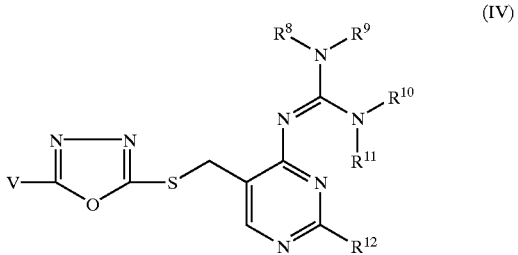

wherein $R^{12}$ is hydrogen atom or alkyl;
V is optionally substituted aryl;
$R^8$, $R^9$, $R^{10}$, and $R^{11}$ are as defined above, the prodrugs thereof, or their pharmaceutically acceptable salts, or their solvates, V) a compound, the prodrugs thereof, or their pharmaceutically acceptable salts, or their solvates as described in above I), wherein $R^1$, $R^2$, $R^3$, and $R^4$ are each independently hydrogen atom, optionally substituted alkyl, alkenyl, alkynyl, or acyl, VI) a compound, the prodrugs thereof, or their pharmaceutically acceptable salts, or their solvates as described in any one of the above II) to IV), wherein $R^8$, $R^9$, $R^{10}$, and $R^{11}$ are each independently hydrogen atom, optionally substituted alkyl, alkenyl, alkynyl, or acyl, VII) a pharmaceutical composition which contains as active ingredient a compound as described in any one of I) to VI), VIII) a pharmaceutical composition for use as an antitumor agent which contains as active ingredient a compound as described in any one of I) to VI)s, IX) a pharmaceutical composition for use as a cytostatic agent which contains as described in any one of I) to VI), X) a pharmaceutical composition for use as an inhibitor against a signal derived from Ras oncogene products which contains as active ingredient a compound as described in any one of I) to VI), XI) use of a compound of any one of I) to VI) for the preparation of a pharmaceutical composition for treating cancer, and XII) a method of treating a mammal, including a human, to alleviate the pathological effects of cancer; which comprises administration to the mammal of a compound as described in any one of I) to VI).

The term "alkyl" employed alone or in combination with other terms in the present specification includes a straight or branched chain monovalent hydrocarbon group having 1 to 8 carbon atoms. Examples of the alkyl include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl and the like. Preferably, C1 to C6 alkyl is exemplified. More preferably, C1 to C3 alkyl is exemplified.

The term "alkenyl" employed alone or in combination with other terms in the present specification includes a straight or branched chain monovalent hydrocarbon group having 2 to 8 carbon atoms and one or more double bonds. An example of the alkenyl includes vinyl, allyl, propenyl, crotonyl, prenyl, a variety of butenyl isomers and the like. Preferably, C2 to C6 alkenyl is exemplified. More preferably, C2 to C3 alkenyl is exemplified.

The term "alkynyl" employed alone or in combination with other terms in the present specification includes a straight or branched chain monovalent hydrocarbon group having 2 to 8 carbon atoms and one or more triple bonds. The alkynyl may contain (a) double bond(s). An example of the alkenyl includes ethynyl, propynyl, 6-heptynyl, 7-octynyl, and the like. Preferably, C2 to C6 alkynyl is exemplified. More preferably, C2 to C3 alkynyl is exemplified.

The term "aryl" employed alone or in combination with other terms in the present specification includes a monocyclic or condensed cyclic aromatic hydrocarbon. An example of the aryl includes phenyl, 1-naphthyl, 2-naphthyl, anthryl and the like. Preferably, phenyl, 1-naphthyl, and 2-naphthyl are exemplified. More preferably, phenyl is exemplified.

The term "aralkyl" in the present specification includes a group wherein the above-mentioned "alkyl" is substituted with the above-mentioned "aryl". An example of aralkyl includes benzyl, phenethyl (e.g., 2-phenylethyl), phenylpropyl (e.g., 3-phenylpropyl), naphthylmethyl (e.g., 1-naphthylmethyl and 2-naphthylmethyl), anthrylmethyl (e.g., 9-anthrylmethyl) and the like. Preferably, benzyl and phenylethyl are exemplified.

The term "heteroaryl" employed alone or in combination with other terms in the present specification includes a 5- to 6-membered aromatic cyclic group which contains one or more hetero atoms selected from the group consisting of oxygen, sulfur, and nitrogen atoms in the ring and may be fused with the above mentioned "aryl", "heteroaryl", "carbocyclic group", and "non-aromatic heterocyclic group". Heteroaryl is bonded at any possible position when the heteroaryl is a condensed ring. Examples of the heteroaryl are pyrrolyl (e.g., 1-pyrrolyl), indolyl (e.g., 3-indolyl), carbazolyl (e.g., 3-carbazolyl), imidazolyl (e.g., 4- imidazolyl), pyrazolyl (e.g., 3-pyrazolyl and 5-pyrazolyl), benzimidazolyl (e.g., 2-benzimidazolyl), indazolyl (e.g., 3-indazolyl), indolizinyl (e.g., 6-indolizinyl), pyridyl (e.g., 3-pyridyl and 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 4-thiazolyl), benzothiazolyl (e.g., 2-benzothiazolyl), furyl (e.g., 2-furyl and 3-furyl), benzofuryl (e.g., 3-benzofuryl), thienyl (e.g., 2-thienyl and 3-thienyl), benzothienyl (e.g., 2-benzothienyl), tetrazolyl, oxadiazolyl (e.g., 1,3,4-oxadiazolyl and 1,2,4-oxadiazolyl), oxazolyl, thiadiazolyl (e.g., 1,3,4-thiadiazolyl and 1,2,4-thiadiazolyl), 4H-1,2,4-triazolyl, quinoxalinyl, 2-pyridone-3-yl, and the like. Preferably, pyridyl, pyrazinyl, furyl, thienyl and the like are exemplified.

The term "5-membered heteroaryl-diyl" herein used includes a 5-membered divalent group derived from above-mentioned "heteroaryl". Examples of the 5-membered heteroaryl-diyl are 2,5-furandiyl, 2,5-thiophendiyl, 2,5-pyrroldiyl, 3,5-pyrazoldiyl, 2,5-(1,3,4-oxadiazole)diyl, 3,5-(1,2,4-oxadiazole)diyl, 2,5-oxazoldiyl, 3,5-isoxazoldiyl, 2,5-(1,3,4-thiadiazole)diyl, 3,5-(1,2,4-thiadiazole)diyl, 3,5-(4H-1,2,4-triazole)diyl, and the like.

The term "non-aromatic heterocyclic group" employed alone or in combination with other terms in the present specification includes a 5- to 7-membered non-aromatic heterocyclic group which contains one or more hetero atoms selected from the group consisting of oxygen, sulfur, and nitrogen atoms in the ring and a cyclic group wherein two or more of the above-mentioned heterocyclic groups are fused. Examples of the heterocyclic group are pyrrolidinyl (e.g., 1-pyrrolidinyl), pyrazolidinyl (e.g., 1-pyrazolidinyl), piperidinyl (e.g., piperidino and 2-piperidinyl), piperazinyl (e.g., 1-piperazinyl), morpholinyl (e.g., morpholino and 3-morpholinyl), and the like.

The term "5-membered non-aromatic heterocycle-diyl" herein used includes a 5-membered divalent group derived from the above-mentioned "non-aromatic heterocyclic group". Examples of the 5-membered non-aromatic heterocycle-diyl are pyrrolidindiyl (e.g., 2,5-pyrrolidindiyl) and the like.

The term "carbocyclic group" herein used includes a 3- to 7-membered non-aromatic carbocyclic group. Examples of the carbocyclic group are cycloalkyl (e.g., cyclopropyl, cyclobutyl, cyclopentyl, cyclohexyl, and cycloheptyl), cycloalkenyl (e.g., cyclopentenyl and cyclohexenyl), and the like.

In this specification, examples of the ring represented by "$R^1$ and $R^2$, $R^3$ and $R^4$, and $R^2$ and $R^3$ each taken together with the adjacent nitrogen atom form the same or different 3- to 6-membered non-aromatic heterocyclic ring" are aziridine, pyrrolidine, piperidine, piperazine, morpholine, imidazolidine, pyrazolidine, pyrrole, py dine, triazine, and the like.

The term "acyl" employed alone or in combination with other terms in the present specification includes alkylcarbonyl of which alkyl part is the above-mentioned "alkyl" and arylcarbonyl of which aryl part is the above-mentioned "aryl". Examples of the acyl are acetyl, propanoyl, benzoyl, and the like.

The term "halogen" herein used means fluoro, chloro, bromo, and iodo.

Examples of "alkyloxy" herein used are methyloxy, ethyloxy, n-propyloxy, isopropyloxy, n-butyloxy, isobutyloxy, sec-butyloxy, tert-butyloxy, and the like. Preferably, methyloxy, ethyloxy, n-propyloxy, and isopropyloxy are exemplified.

Examples of "alkylthio" herein used are methylthio, ethylthio, n-propylthio, isopropylthio, n-butylthio, isobutylthio, sec-butylthio, tert-butylthio, and the like. Preferably, methylthio, ethylthio, n-propylthio, and isopropylthio are exemplified.

Examples of "alkyloxycarbonyl" herein used are methyloxycarbonyl, ethyloxycarbonyl, n-propyloxycarbonyl, and the like.

The term "optionally substituted amino" herein used means amino substituted with one or two of the above-mentioned "alkyl", "aralkyl", "acyl", optionally substituted sulfonyl (e.g., alkyloxyphenylsulfonyl), arylalkylene (e.g., benzylidene), alkylsulfonyl, carbamoyl and the like or non-substituted amino. Examples of the optionally substituted amino are amino, methylamino, ethylamino, dimethylamino, ethylmethylamino, diethylamino, benzylamino, benzoylamino, acetylamino, propionylamino, tert-butyloxycarbonylamino, benzylidenamino, methylsulfonylamino, 4-methoxyphenylsulfonylamino, and the like. Preferably, amino, methylamino, dimethylamino, diethylamino, acetylamino are exemplified.

Substituentson the aromatic ring of "optionally substituted aralkyl" are, for example, hydroxy, alkyloxy (e.g., methyloxy and ethyloxy), mercapto, alkylthio (e.g., methylthio), cycloalkyl (e.g., cyclopropyl, cyclobutyl, and cyclopentyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), aryloxy (e.g., phenyloxy), optionally substituted amino (e.g., amino, methylamino, dimethylamino, diethylamino, and benzylidenamino), alkyl (e.g., methyl, ethyl, n-propyl, isopropyl, n-butyl, isobutyl, sec-butyl, tert-butyl, n-pentyl, isopentyl, and neopentyl), alkenyl (e.g., vinyl and propenyl), alkynyl (e.g., ethynyl and phenylethynyl), formyl, lower alkanoyl (e.g., acetyl and propionyl), acyloxy (e.g., acetyloxy), acylamino, alkylsulfonyl (e.g., methylsulfonyl), and the like. These substituents may be substituted at one or more possible position(s).

Substituents of "optionally substituted alkyl", "optionally substituted alkyloxy", and "optionally substituted alkyloxycarbonyl" are, for example, hydroxy, alkyloxy (e.g., methyloxy and ethyloxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), optionally substituted amino (e.g., amino, methylamino, dimethylamino, carbamoylamino, and tert-butyloxycarbonylamino), acyloxy (e.g., acetyloxy), optionally substituted aralkyloxy (e.g., benzyloxy and 4-methyloxyphenylmethyloxy), and the like. These substituents may be substituted at one or more possible position(s).

Substituents of "optionally substituted alkenyl" and "optionally substituted alkynyl" are, for example, hydroxy, alkyloxy (e.g., methyloxy and ethyloxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), optionally substituted amino (e.g., amino, methylamino, dimethylamino, carbamoylamino, and tert-butyloxycarbonylamino), acyloxy (e.g., acetyloxy), optionally substituted aralkyloxy (e.g., benzyloxy and 4-methyloxyphenylmethyloxy), optionally substituted aryl (e.g., phenyl), and the like. These substituents may be substituted at one or more possible position(s).

The preferable examples of "optionally substituted alkyl" are methyl, ethyl, n-propyl, isopropyl, n-butyl, trifluoromethyl, 2,2,2-trifluoroethyl, hydroxymethyl, cyclohexylmethyl, carboxyethyl, acetyloxyethyl, and benzyloxymethyl. More preferably, methyl, ethyl, n-propyl, isopropyl, n-butyl, trifluoromethyl, 2,2,2-trifluoroethyl are exemplified.

Substituents of "optionally substituted aryl", "optionally substituted heteroaryl", "optionally substituted 5-membered heteroaryl-diyl", "optionally substituted 5-membered non-aromatic heterocycle-diyl", and "an optionally substituted non-aromatic heterocyclic group" are, for example, hydroxy, optionally substituted alkyloxy (e.g., methyloxy, ethyloxy, n-propyloxy, isopropyloxy, ethyloxycarbonylmethyloxy, carboxymethyloxy and 4-methoxyphenylmethyloxy), mercapto, alkylthio (e.g., methylthio), cycloalkyl (e.g., cyclopropyl, cyclobutyl, cyclopentyl), halogen (e.g., fluoro, chloro, bromo, and iodo), carboxy, alkyloxycarbonyl (e.g., methyloxycarbonyl, ethyloxycarbonyl, and tert-butyloxycarbonyl), nitro, cyano, haloalkyl (e.g., trifluoromethyl), aryloxy (e.g., phenyloxy), optionally substituted amino (e.g., amino, methylamino, dimethylamino, ethylamino, diethylamino, N,N-acetylmethylamino, benzylidenamino, 4-methoxyphenylsulfonylamino, methylsulfonylamino, benzoylamino, acetylamino, propionylarmino, and tert-butyloxycarbonylamino), optionally substituted aminosulfonyl (e.g., aminosulfonyl), optionally substituted alkyl (e.g., methyl, ethyl, n-propyl, isopropyl, n-butyl, isobutyl, sec-butyl, tert-butyl, n-pentyl, isopentyl, neopentyl, t-butyloxycarbonylaminomethyl, and aminomethyl), alkenyl (e.g., vinyl, propenyl, and prenyl), optionally substituted alkynyl (e.g., ethynyl and phenylethynyl), alkenyloxy (e.g., propenyloxy and prenyloxy), formyl, acyl (e.g., acetyl, propionyl, and benzoyl), acyloxy (e.g., acetyloxy), optionally substituted carbamoyl (e.g., carbamoyl and dimethylaminocarbonyl), alkylsulfonyl (e.g., methylsulfonyl), aryl (e.g., phenyl), aralkyl (e.g., benzyl), carbothioamide, optionally substituted heterocyclic group (e.g., dioxolanyl, 2-methyl-1,3-dioxolane-2-yl, pyrrolidinyl, and piperidino), optionally substituted heteroaryl (e.g., 2-pyridyl, 3-pyridyl, 4-pyridyl, pyridine N-oxide-4-yl, 1-methyl-2-pyridone-4-yl, 1-pyrrolyl, 2-pyrrolyl, and 3-pyrrolyl), and the like. These substituents may be substituted at one or more possible position(s). Preferably, optionally substituted amino, halogen, nitro, alkyl, and alkyloxy are exemplified.

Examples of "optionally substituted aryl" are phenyl, 2-aminophenyl, 3-aminophenyl, 4-aminophenyl, 2-acetylaminophenyl, 4-acetylaminophenyl, 2-benzoylaminophenyl, 4-benzoylaminophenyl, 2-methylsulfonylaminophenyl, 2-propionylaminophenyl, 2-methylaminophenyl, 4-methylaminophenyl, 2-dimethylaminophenyl, 4-dimethylaminophenyl, 2-ethylaminophenyl, 4-ethylaminophenyl, 4-diethylaminophenyl, 2-(4-methoxyphenylsulfonylamino)phenyl, 2-hydroxyphenyl, 4-hydroxyphenyl, 2-ethyloxycarbonylmethyloxyphenyl, 2-carboxymethyloxyphenyl, 2-chlorophenyl, 4-chlorophenyl, 4-bromophenyl, 4-iodophenyl, 4-trifluoromethylphenyl, 2-methylphenyl, 4-methylphenyl, 4-methyloxyphenyl, 4-ethyloxyphenyl, 4-n-propyloxyphenyl, 4-isopropyloxyphenyl, 4-tert-butyloxycarbonylphenyl, 4-prenyloxyphenyl, 2-nitrophenyl, 4-nitrophenyl, 4-(4-methoxyphenylmethyloxy)phenyl, 4-methyloxycarbonylphenyl, 4-aminosulfonylphenyl, 4-(N,N-dimethylaminocarbonyl)phenyl, 4-carboxyphenyl, 4-biphenylyl, 4-benzoylphenyl, 4-pyrrolidinophenyl, 4-piperidinophenyl, 2-(3-amino)naphthyl, 2-amino-5-chlorophenyl, 2-amino-3-chlorophenyl, 2-amino-4-chlorophenyl, 2-amino-6-chlorophenyl, 4-amino-2-chlorophenyl, 2-amino-4-fluorophenyl, 2-amino-5-fluorophenyl, 2-amino-6-fluorophenyl, 4-amino-2-fluorophenyl, 2-amino-4,5-difluorophenyl, 2-amino-3-methylphenyl, 2-amino-4-methylphenyl, 2-amino-5-methylphenyl, 2-amino-6-methylphenyl, 4-amino-3-methylphenyl, 4-amino-3-methyloxyphenyl, 2-amino-4-nitrophenyl, 4-amino-3-hydroxyphenyl, 2-amino-4-carboxyphenyl, 2-amino-4-methyloxycarbonylphenyl, 4-amino-2-hydroxyphenyl, 4-amino-3-(4-methoxyphenylmethyloxy)phenyl, 2,4-diaminophenyl, 3,4-diaminophenyl, 2-(N-acetyl-N-methylamino)phenyl, 2-acetylamino4-fluorophenyl, 2-acetylamino-4-chlorophenyl, 2,3-dichlorophenyl, 2,4-dichlorophenyl, 2-(3-amino)naphthyl, 4-amino-2-methylphenyl, 2-fluoro-4-nitrophenyl, 4-amino-2-methyloxyphenyl, 2-methyloxy-4-nitrophenyl, 4-fluoro-2-nitrophenyl, 4-amino-2-trifluoromethylphenyl, 4-amino-2-ethyloxyphenyl, 4-amino-2-trifluoromethyloxyphenyl, 2-chloro-4-nitrophenyl, 2-methyl-4-nitrophenyl, 4-nitro-2-trifluoromethyloxyphenyl, 4-nitro-2-trifluoromethylphenyl, 2-ethyloxy-4-nitrophenyl, and the like.

Examples of "optionally substituted heteroaryl" are 3-pyridyl, 3-(2-amino)pyridyl, 5-(2-amino)pyridyl, 2-(3-amino)pyrazinyl, 4-(3-amino)pyrazolyl, 5-(4-amino-2-methyl)pyrimidinyl, 3-(2-amino)thienyl, 2-(3-methyl)thienyl, 2-(5-methyl)thienyl, 2-furyl, 3-furyl, 3-(2-methyl)turyl, 3-(2,5-dimethyl)furyl, 2-(5-bromo)faryl, 4-(2-nitro)furan, 3-(1-methyl-4-nitro)pyrazolyl, 5-(1-methyl-4-nitro)pyrazolyl, 3-(5-nitro)pyrazolyl, 3-(4-nitro)pyyazoyl, 2-(3-pyridyl)-thiazole-4-yl, 2-(4-pyridyl)-thiazole4-yl, 6-(1-pyrrolyl)-pyridine-3-yl, N-methyl-2-pyridone-3-yl, and the like.

Examples of "optionally substituted 5-membered heteroaryl-diyl" are 2,5-flurandiyl, 2,5-thiophendiyl, 2,5-pyrroldiyl, 3,5-pyrazoldiyl, 2,5-(1,3,4-oxadiazole)diyl, 3,5-(1,2,4-oxadiazole)diyl, 2,5-oxazoldiyl, 3,5-isooxazoldiyl, 2,5-(1,3,4-thiadiazole)diyl, 3,5-(1,2,4-thiadiazole)diyl, 3,5-(4H-1,2,4-triazole)diyl, 3,5-(1-methylpyrazole)diyl, and the like.

Examples of "optionally substituted arylalkenyl" are 4-aminophenylethenyl and the like.

Preferable example of $R^1$ to $R^6$, X, Y, and Z of the compound represented by the formula (I) are shown below as groups (a) to (s).

$R^1$ and $R^2$ are (a) each independently hydrogen atom, optionally substituted alky, alkenyl, or alkynyl; (b) each independently hydrogen atom, alkyl optionally substituted with halogen, alkenyl, or alkynyl; and (c) one is hydrogen atom and the other is C1 to C3 alkyl optionally substituted with halogen.

$R^3$ and $R^4$ are (d) each independently hydrogen atom, optionally substituted alkyl, alkenyl, or alkynyl; (e) each independently hydrogen atom, alkyl optionally substituted with halogen, alkenyl, or alkynyl; and (f) one is hydrogen atom and the other is C1 to C3 alkyl optionally substituted with halogen.

$R^5$ is (g) hydrogen atom, alkyloxy, alkylthio, or optionally substituted alkyl; (h) hydrogen atom or alkyl; and (i) hydrogen or $C^1$ to C2 alkyl.

$R^6$ is (j) hydrogen atom or alkyl; and (k) hydrogen atom. X is (l) —O— or —S—; and (m) —S—.

Y is (n) 5-membered heteroaryl-diyl; (o) 2,5-(1,3,4-oxadiazole)diyl, 3,5-(1,2,4-oxadiazole)diyl, 2,5-(1,3,4-thiadiazole)diyl, or 3,5-(1,2,4-thiadiazole)diyl; and (p) 2,5-(1,3,4-oxadiazole)diyl.

Z is (q) optionally substituted aryl or optionally substituted heteroaryl; (r) optionally substituted phenyl or optionally substituted monocyclic heteroaryl; and (s) phenyl, pyridyl, thienyl, or furyl, which are substituted with 1 to 3 substituents selected from the group consisting of optionally substituted amino, halogen, alkyl, alkyloxy, acyl, phenyl, alkyloxycarbonyl, hydroxy, nitro, or haloalkyl.

A preferred group of compounds represented by the formula (I) is shown below. [($R^1$, $R^2$), ($R^3$, $R^4$), $R^5$, $R^6$, X Y]=[a, d, g, j, l, n], [a, d, g, j, l, o], [a, d, g, j, l, p], [a, d, g, j, m, n], [a, d, g, j, m, o], [a, d, g,j, m, p], [a, d, g, k, l, n], [a, d, g, k, l, o], [a, d, g, k, l, p], [a, d, g, k, m, n], [a, d, g, k, m, o], [a, d, g, km, p], [a, d, h, j, l, n], [a, d, h,j, l, o][a, d, h, j, l, p], [a, d, h, j, m, n], [a, d, h,j, m, o], [a, d, h,j, m, p], [a, d, h, k, l, n], [a, d, h, k, l, o], [a, d, h, k, l, p], [a, d, h, k, m, n], [a, d, h, k, m, o], [a, d, h, k, m, p], [a, d, i, j, l, n], [a, d, i, j, l, o], [a, d, i, j, l, p], [a, d, i, j, m, n], [a, d, i,j, m, o], [a, d, i, j, m, p], [a, d, i, k, l, n], [a, d, i, k, l, o], [a, d, i, k, l,p], [a, d, i, k, m, n], [a, d, i, k, m, o], [a, d, i, k, m, p], [a, e, g, j, l, n], [a, e, g, j, l, p], [a, e, g, j, m, n], [a, e, g, j, m, o], [a, e, g, j, m,o], [a, e, g, j, m, p], [a, e, g, k, l, n], [a, e, g, k, l, o], [a, e, g, k, m, n], [a, e, g, k, m, n], [a, e, g, k, m, o], [a, e, g, k, m, p], [a, e, h, j, l, n], [a, e, h, j, l, o], [a, e, h, j, l,p], [a, e, h,j, m, n], [a, e, h, j, m, o], [a, e, h i, m, p], [a, e, h, k, l, n], [a, e, h, k, l, o], [a, e, , k, l, p], [a, e, h, k, m, n], [a, e, h, k, m, o], [a, e, h, k, p], [a, e, i, j, l, n], [a, e, i, j, l, o], [a, e, i, j, l, p], [a, e, i, j, m, n], [a, e, i, j, m, o], [a, e, i, j, m, p], [a, e, i, k, l, n], [a, e, i, k, l, o], [a, e, i, k, 1 p], [a, e, i, k, m, n], [a, e, i, k, m, o], [a, e, i, k, m, p], [a, f, g, j, l, n], [a, f, g, j, l, o], [a, f, g,j, , p], [a, f g,j, m, n], [a, f, g, j, m, o], [a, f, g, j, m, p], [a, f, g, k, l, n], [a, f, g, k, l, o], [a, f, g, k, l, p], [a, f, g, k, m, n], [a,f, g, k, m, o], [a, f, g, k, m, p], [a, f, h, j, l, n], [a, f, h, j, l, o], [a, f, h, j, l, p], [a, f, h, j, m, n], [a, f, h, j, m, o], [a, f, h, j, m, p), [a, f, h, k, l, n], [a, f, h, k, l, o], [a, f, h, k, l, p], [a, f, h, k, m, n], [a, f, h, k, o], [a, f, h, k, m, p], [a, f, i, j, l, n], [a, f i, j, l, o], [a, f, i, j, l, p], [a, f, i, j, m, n], [a, f, i, j, m, o], [a, f, i, j, m, p], [a, f i, k, l, n], [a, f, i, k, l, o], [a, f, i, k, l, p], [a, f, i, k, m, n], [a, f, i, k, m, o], [a, f, i, k, n, p], [b, d, g, j, l, n], [b, d, g, j, l, o], [b, d, g, j, l, p], [b, d, g, j, m, n], [b, d, g, j, m, o], [b, d, g, j, m, p], [b, d, g, k, l, n], [b, d, g, k, l, o], [b, d, g, k, l, p], [b, d, g, k, m, n], [b, d, g, k, m o], [b, d, g, k, m, p], [b, d, h, j, l, n], [b, d, h, j, l, o], [b, d, h, j, l, p], [b, d, h, j, m, n], [b, d, h, j, m, o], [b, d, h, j, m, p], [b, d, h, k, l, n], [b, d, h, k, l, o], [b, d, h, k, l, p], [b, d, h, k, m, n], [b, d, h, k, m, o], [b, d, h, k, m, p], [b, d, i, j, l, n ], [b, d, i, j, l, o], [b, d, i, j, l, p], [b, d, i, j, l, n], [b, d, i, j, m, o], [b, d, i, j, m, p], [b, d, i, k, l, n], [b, d, i, k, l, o], [b, d, i, k, l, p], [b, d, i, k, m, n], [b, d, i, k, m, o], [b, d, i, k, m, p], [b, e, g, j, l, n], [b, e, g, j, l, o], [b, e, g, j, l, p], [b, e, g, j, m, n], [b, e, g, j, m, o], [b, e, g, j, m, p], [b, e, g, k, l, n][b, e, g, k, l, o], [b, e, g, k, l, p], [b, e, g, k, m, n], [b, e, g, k, m, o], [b, e, g, k, m, p], [b, e, h, j, l, n], [b, e, h, j, l, o], [b, e, h, j, l, p], [b, e, h, j, m, n], [b, e, h, j, m, o], [b, e, h, j, m, p], [b, e, h, k, l, n], [b, e, h, k, l, o], [b, e, h, k, l, p], [b, e, h, k, m, n], [b, e, h, k, m, o], [b, e, h, k, m, p], [b, e, i, j, l, n], [b, e, i, j, l, o], [b, e, i, j, l, p], [b, e, i, j, m, n], [b, e, i, j, m, o], [b, e, i, j, m, p], [b, e, i, k, l, n], [b, e, i, k, l, o], [b, e, i, k, l, p], [b, e, i, k, m, n], b, e, i, k, m, o], [b, e, i, k, m, p], [b, f, g, j, l, n], [b, f, g, j, l, o], [b, f, g, j, l, p], [b, f, g, m, n], [b, f, g, j, m, o], [b, f, g, j, m, p], [b, f, g, k, l, n], [b, f, g, k, l, o], [b, f, g, k, l, p], [b, f, g, k, m, n], [b, f, g, k, m, o], [b, f, g, k, m, p], [b, f, h, j, l, n], [b, f, h, j, l, o], [b, f, h, j, l, p], [b, f, h, j, m, n], [b, f, h, j, m, o], [b, f, h, j, m, p], [b, f, h, k, l, n], [b, f, h, k, l, o], [b, f, h, k, l, p], [b, f, h, k, m, n], [b, f, h, k, m, o], [b, f, h, k, m, p], [b, f, i, j, l, n], [b, f, i, j, l, o], [b, f, i, j, l, p], [b, f, i, j, m, n,], [b, f, i, j, m, o], [b, f, i, j, m, p], [b, f, i, k, l, n], [b, f, i, k, l, o], [b, f, i, k, l, p], [b, f, i, k, m, n], [b, f, i, k, m, o], [b, f, i, k, m, p], [c, d, g, j, l, n], [c, d, g, j, l, o], [c, d, g, j, l, p], [c, d, g, j, m, n], [c, d, g, j, m, o], [c, d, g, j, m, p], [c, d, g, k, l, n], [c, d, g, k, l, o], [c, d, g, k, l, p], [c, d, g, k, m, n], [c, d, g, k, m, o], [c, d, g, k, m, p], [c, d, h, j, l, n], [c, d, h, j, l, o], [c, d, h, j, l, p], [c, d, h, j, m, n], [c, d, h, j, m, o], [c, d, h, j, m, p], [c, d, h, k, l, n], [c, d, h, k, l, o], [c, d, h, k, l, p], [c, d, h, k, m, n], [c, d, h, k, m, o], [c, d, h, k, m, p], [c, d, i, j, l, n], [c, d, i, j, l, o], [c, d, i, j, m, p], [c, d, i, k, l, n], [c, d, i, k, l, o], [c, d, i, k, l, p], [c, d, i, k, m, n], [c, d, i, k, m, o], [c, d, i, k, m, p], [c, e, g, j, l, n], [c, e, g, j, l, o], [c, e, g, j, l, p], [c, e, g, j, m, n], [c, e, g, j, m, o], [c, e, g, j, m, p], [c, e, g, k, l, n], [c, e, g, k, l, o], [c, e, g, k, l, p], [c, e, g, k, m, n], [c, e, g, k, m o], [c, e, g, k, m, p], [c, e, h, j, l, n], [c, e, h, j, l, o], [c, e, h, j, l, p], [c, e, h, j, m, n], [c, e, h, j, m, o], [c, e, h, j, m, p], [c, e, h, k, l, n], [c, e, h, k, l, o], [c, e, h, k, 1 ,p], [c, e, h, k, m, n], [c, e, h, k, m, o], [c, e, h, k, m, p], [c, e, i, j, l, n], [c, e, i, j, l, o], [c, e, i, j, l, p], [c, e, i, j, m, n], [c, e, i, j, m, o], [c, e, i, j, m, p], [c, e, i, k, l, n], [c, e, i, k, l, o], [c, e, i, k, l, p], [c, e, i, k, m, n], [c, e, i, k, m, o], [c, e, i, k, m, p], [c, f, g, j, l, n], [c, f, g, j, l, o], [c, f, g, j, l, p], [c, f, g, j, m, n], [c, f, g, j, m, o], [c, f, g, j, m, p], [c, f, g, k, l, n], [c, f, g, k, l, o], [c, f, g, k, l, p], [c, f, g, k, m n], [c, f, g, k, m, o], [c, f, g, k, m, p], [c, f, h, j, l, n], [c, f, h, j, l, o], [c, f, h, j, l, p], [c, f, h, j, m, n], [c, f, h, j, m, o], [c, f, h, j, m, p], [c, f, h, k, l, n], [c, f, h, k, l, o], [c, f, h, k, l, p], [c, f, h, k, m, n], [c, f, h, k, m, o], [c, f, h, k, m, p], [c, f, i, j, l, n], [c, f, i, j, l, o], [c, f, i, j, l, p], [c, f, i, j, m, n], [c, f, i, j, m, o], [c, f, i, j, m, p], [c, f, i, k, l, n], [c, f, i, k, l, o], [c, f, i, k, l, p], [c, f, i, k, m, n], [c, f, i, k, m, o], [c, f, i, k, m, p]

Preferred embodiments of this invention are compounds wherein Z is any one of (q) to (s) and [($R^1$, $R^2$), ($R^3$, $R^4$), $R^5$, $R^6$, X, Y] is any one of the above combinations.

In this specification, the compound represented by the formula (I) wherein $R^1$ is hydrogen atom may be represented as an isomer of the following formula (V):

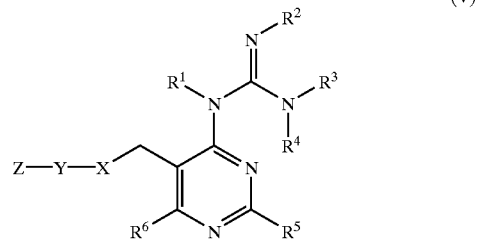

wherein $R^2$, $R^3$, $R^4$, $R^5$, $R^6$, X, Y, and Z are as defined above and $R^1$ is hydrogen atom.

The compounds represented by the formula (II), (III), and (IV) may be each isomer as well.

The compound represented by the formula (XXV):

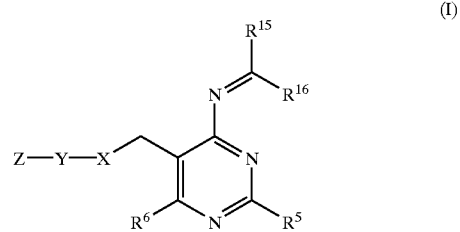

wherein one of $R^{15}$ and $R^{16}$ is —$NR^1R^2$ wherein $R^1$ and $R^2$ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, or acyl, or $R^1$ and $R^2$ together with the adjacent nitrogen atom may form 3- to 6-membered ring, and the other is alkylthio;

or both of $R^{15}$ and $R^{16}$ are alkylthio;

$R^5$ and $R^6$ are each independently hydrogen atom, optionally substituted alkyl, optionally substituted alkenyl, optionally substituted alknyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

X is —N(R$^7$)—, —NH—NH—, —O—, or —S— wherein R$^7$ is hydrogen atom or optionally substituted alkyl;

Y is optionally substituted 5-membered non-aromatic heterocycle-diyl or optionally substituted 5-membered heteroaryl-diyl; and Z is optionally substituted aryl, optionally substituted heteroaryl, or optionally substituted alkenyl;

the prodrugs thereof, or their pharmaceutically acceptable salts, or their solvates are also useful as a pharmaceutical composition, an anti tumor agent, a cytostatic agent, and an inhibitor against a signal derived from Ras oncogene products.

BEST MODE FOR CARRYING OUT THE INVENTION

The compound of the present invention represented by the formula (I) can be synthesized by the well-known method described in the literature of chemistry. A summary of the useful method for synthesis of the compound of the present invention is shown below.

(Synthetic method)

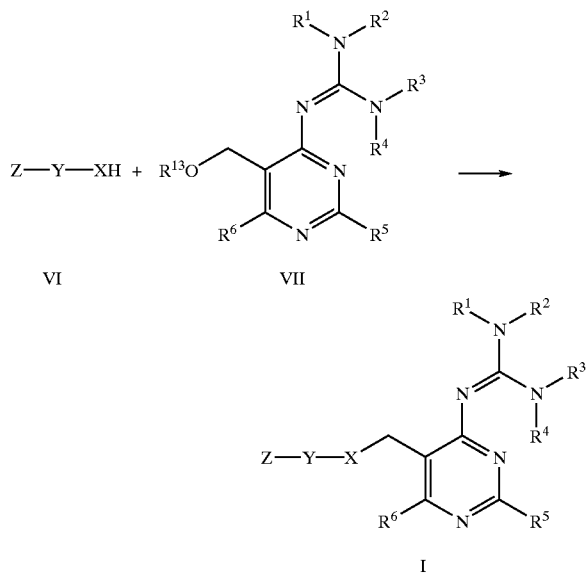

wherein R$^1$, R$^2$, R$^3$, R$^4$, R$^5$, R$^6$, X, Y, and Z are as defined above; R$^{13}$ is hydrogen atom or a protective group of a hydroxy group.

The compound represented by the formula (I) can be synthesized by reacting Z—Y—XH (VI) with the guanidinopyrimidine derivatives (VII). The guanidinopyrimidine derivatives (VII) in a solvent such as water, acetic acid, pyridine, and the like is treated with a hydrohalogenic acid such as hydrochloric acid and hydrobromic acid to give hydrogen halide salts of 5-halogenomethylpyrimidine. When R$^{13}$ is hydrogen atom, a halogenation agent such as thionyl halide and phosphorous halide can be used. The obtained salt and Z—Y—XH (VI) in a solvent such as water, methanol, ethanol, N,N-dimethylformamide, dimethylsulfoxide, tetrahydrofuran are reacted with an appropriate base, for example an inorganic base such as sodium hydroxide, potassium butoxide, sodium hydride, potassium hydride, and potassium carbonate or an organic base such as triethylamine, pyridine, and diisopropylethylamine, at −20° C. to 100° C., preferably 0° C. to 30° C. for 1 min to 24 h, preferably 10 min to 12 h to give the aimed compound (I).

Compound (VI) and compound (VII) can be synthesized by the methods A to I and the methods J to N as shown below.

In the methods A to I, Z represents optionally substituted aryl or optionally substituted heteroaryl. The starting material of each method is commercially available or can be synthesized by well-know method from the compound which is commercially available.

Method A: Synthetic method of the compound wherein Y is an oxadiazole ring and X is —S—.

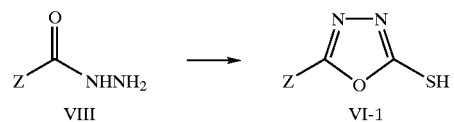

Compound (VIII) in a solvent such as ethanol and benzene is reacted with carbon disulfide and a base such as triethylamnine, sodium hydroxide, potassium carbonate at 0° C. to 100° C., preferably 60° C. to 100° C. for 10 min to 24 h, preferably 2 h to 12 h to give compound (VI-1).

Method B: Synthetic method of the compound wherein Y is an oxadiazole ring and X is —O—.

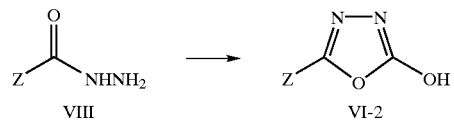

To a solution of compound (VIII) in a solvent such as tetrahydrofuran and toluene is added carbonyldiimidazole and the mixture is reacted at 0° C. to 120° C., preferably 60° C. to 120° C. for 10 min to 24 h, preferably 2 h to 12 h to give compound (VI-2).

Method C: Synthetic method of the compound wherein Y is an oxadiazole ring and X is —N(R$^7$)—.

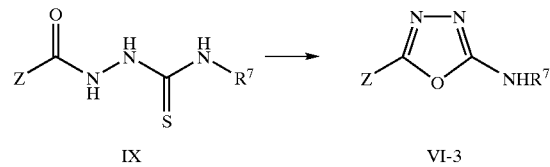

wherein R$^7$ is as defined above.

To a solution of compound (IX) in a solvent such as ethanol and tetrahydroftiran is added mercury oxide and the mixture is reacted at 0° C. to 120° C., preferably 30° C. to 80° C. for 0.5 h to 24 h, preferably 1 h to 24 h to give compound (VI-3).

Method D: Synthetic method of the compound wherein Y is a thiadiazole ring and X is —S—.

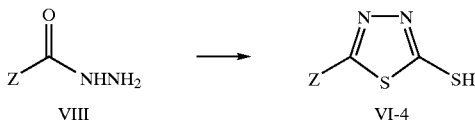
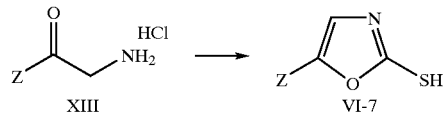

To a solution of compound (VIII) in a solvent such as ethanol and tetrahydrofuran are added carbon disulfide and a base such as triethylamine and sodium hydroxide and the mixture is reacted at 0° C. to 100° C., preferably 20° C. to 60° C. for 0.5 h to 24 h, 1 h to 12 h. After the solvent is removed, the residue is reacted with conc. sulfuric acid at −20° C. to 40° C., preferably 0° C. to 20° C. for 1 min to 12 h, preferably 10 min to 1 h to give compound (VI-4).

Method E: Synthetic method of the compound wherein Y is a furan ring and X is —S—.

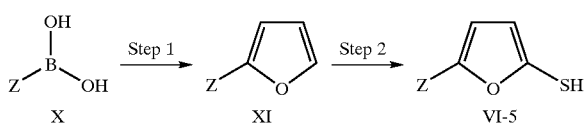

(Step 1)
Halogenated furan such as 2-bromofuran is reacted with compound (X) in a solvent such as dimethylformamide, toluene, xylene, benzene, tetrahydrofliran, and ethanol in the presence of palladium catalyst such as Pd(Ph$_3$P)$_4$ and a base such as potassium carbonate, calcium carbonate, triethylamine, and sodium methoxide to give the aimed compound (XI) (Suzuki reaction). The reaction temperature is room temperature to 100° C., preferably room temperature to 80° C. and the reaction time is 5 to 50 h, preferably 15 to 30 h.

(Step 2)
To a solution of compound (XI) in a solvent such as tetrahydrofuran, diethyl ether, and toluene is added a base such as n-butyllithium and sec-butyllithium and the mixture is stirred at −100° C. to 50° C., preferably −80° C. to 0° C. for 1 min to 24 h, preferably 10 min to 60 min. To the mixture is added sulfur and the resulting mixture is reacted at −100° C. to 50° C., preferably −80° C. to 0° C. for 1 h to 24 h, preferably 1 h to 12 h to give the a compound (VI-5).

Method F: Synthetic method of the compound wherein Y is a thiophene ring and X is —S—.

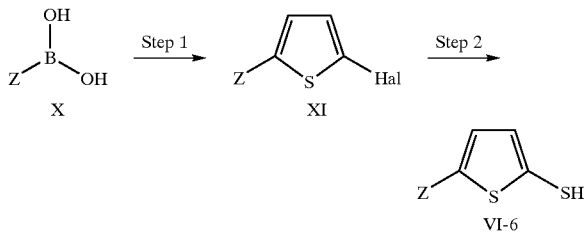

wherein Hal is halogen.

The steps 1 and 2 can be carried out in a manner similar to those described in step 1 and 2 of Method E.

Method G: Synthetic method of the compound wherein Y is an oxazole ring and X is —S—.

To a solution of compound (XIII) in a solvent such as dichloromethane, toluene, and diethyl ether is added thiophosgene in the presence of a base such as triethylamine and sodium hydroxide and the mixture is reacted at −20° C. to 100° C., preferably 0° C. to 40° C. for 1 h to 48 h, preferably 1 h to 24 h to give compound (VI-7).

Method H: Synthetic method of the compound wherein Y is an oxazole ring and X is —O— or —S—.

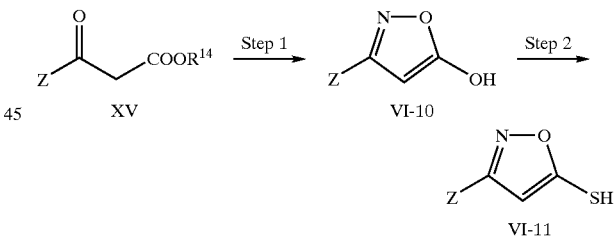

(Step 1)
Compound (XIV) in a solvent such as dichloromethane and acetonitrile is reacted with a condensing agent such as dicyclohexylcarbodiimide at −20° C. to 50° C., preferably 0° C. to 20° C. for 5 min to 24 h, preferably 10 min to 2 h to give compound (VI-8).

(Step 2)
To a solution of compound (VI-8) in a solvent such as toluene and dioxane is added Lawesson's reagent and the mixture is reacted at 60° C. to 150° C., preferably 80° C. to 120° C. for 1 h to 24 h, preferably 2 to 12 h to give compound (VI-9).

Method I: Synthetic method of the compound wherein Y is an isoxazole ring and X is —O— or —S—.

wherein $R^{14}$ is C1 to C3 alkyl.

(Step 1)
Compound (XV) in a solvent such as methanol and tetrahydrofuran is reacted with hydroxylamine at 20° C. to 100° C., preferably 50° C. to 80° C. for 1 h to 24 h, preferably 2 h to 12 h to give compound (VI-10).

(Step 2)
Compound (VI-11) can be obtained in a manner similar to that described in step 2 of Method H.

The compounds which are not concretely shown in the above methods can be synthesized by a combination of some of the above methods A to I and well-know method.

In the methods J to N, $R^1$, $R^2$, $R^3$, $R^4$, $R^5$, $R^6$, and $R^{13}$ are as defined above. The starting material of each method is commercially available or can be synthesized by well-know method from the compound which is commercially available.

Methods J and K are process for construction of a pyrimidine ring and can be carried out in accordance with well-known method (see Journal of Chemical Society, 1937, p-364, ibid., 1943, p-388 and J. Pharm. Soc. Japan 1954, p-742).

Methods L to N are processes that a guanidino group is introduced to the pyrimidine derivative obtained in the Method J and Method K and can be carried out in accordance with well-known method (see Journal of Chemical Society, 1948, p-58, ibid., 1946, p-1063 and Synthesis, 1988, p-460).

Method J: Synthesis of a pyrimidine ring

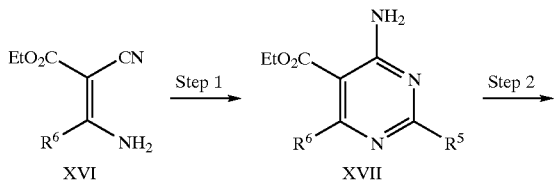

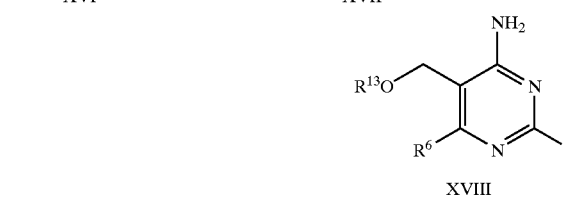

(Step 1)

Compound (XVI) in a solvent such as ethanol, tetrahydrofuran, and dimethylformamide is reacted with $R^5$—C(=S)—$NH_2$ in the presence of a base such as sodium ethylate and sodium hydroxide at 0° C. to 150° C., preferably 60° C. to 100° C. for 0.5 h to 48 h, preferably 1 h to 12 h to give compound (XVII).

(Step 2)

Compound (XVII) in a solvent such as ether and tetrahydrofuran or a mixed in solvent such as ether-tetrahydrofuran is reacted with a reducing agent such as lithium aluminum hydride and lithium borohydride at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like to give compound (XVIII). Methyl, ethyl, trimethylsilyl, tert-butyldimetylsilyl, and the like are exemplified as $R^{13}$.

Method K: Synthesis of a pyrimidine ring

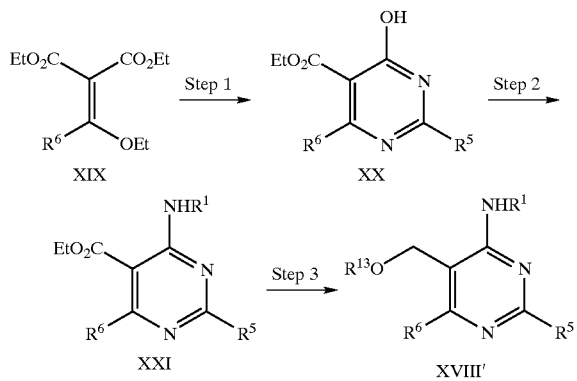

(Step 1)

Compound (XIX) in a solvent such as ethanol, tetrahydrofuran, and dimethylformamide is reacted with $R^5$—C(=NH)—$NH_2$ or its salt in the presence of a base such as sodium ethylate and sodium hydroxide at 0° C. to 150° C., preferably 60° C. to 100° C. for 0.5 h to 48 h, preferably 1 h to 12 h to give compound (XX) or its salt.

(Step 2)

Compound (XX) or its salt in a solvent such as toluene and dichloroethane or without a solvent is reacted with a halogenation agent such as thionyl chloride and phosphorus oxychloride at 0° C. to 150° C., preferably 60° C. to 120° C. for 0.5 h to 12 h, preferably 1 h to 5 h to give a halogenated derivative. The obtained halogenated derivative in a solvent such as ethanol and tetrahydrofuran is reacted with $R^1NH_2$ at −80° C. to 100° C., preferably −20° C. to 30° C. for 0.5 h to 48 h, preferably 1 h to 12 h to give compound (XX).

(Step 3)

This step can be carried out in a manner similar to that described in step 2 of Method J.

Method L: Introduction of a guanidino group

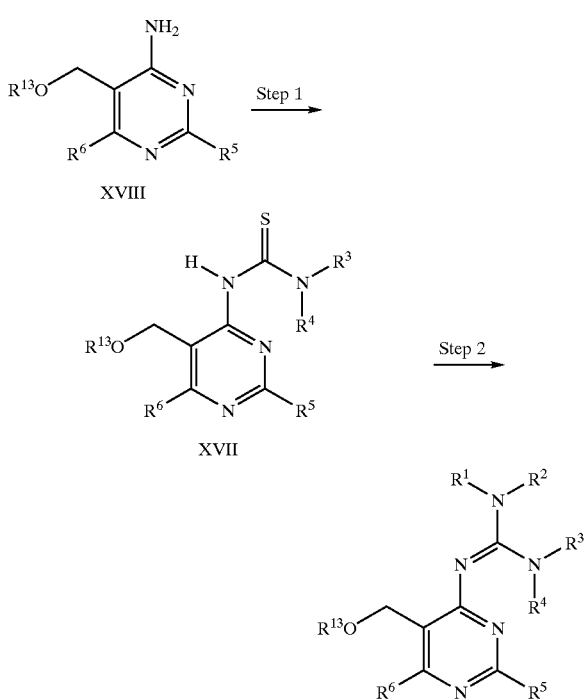

(Step 1)

Compound (XVIII) in a solvent such as dimethylformamide, pyridine, and tetrahydrofuran is reacted with $R^3$-NCS or $R^3R^4$NCS-Hal wherein Hal is halogen in the presence or absence of a base such as sodium hydride at −20° C. to 120° C., preferably 0° C. to 120° C. for 0.5 h to 48 h, preferably 1 h to 24 h to give compound (XXII).

(Step 2)

To a solution of compound (XXII) in a solvent such as methanol and tetrahydrofiran are added a heavy metal salt or heavy metal oxide such as HgO and $R^1R^2$NH and the mixture is reacted at −20° C. to 100° C., preferably 0° C. to 50° C. for 0.5 h to 48 h, preferably 1 h to 12 h to give compound (VII).

Method M: Introduction of a guanidino group

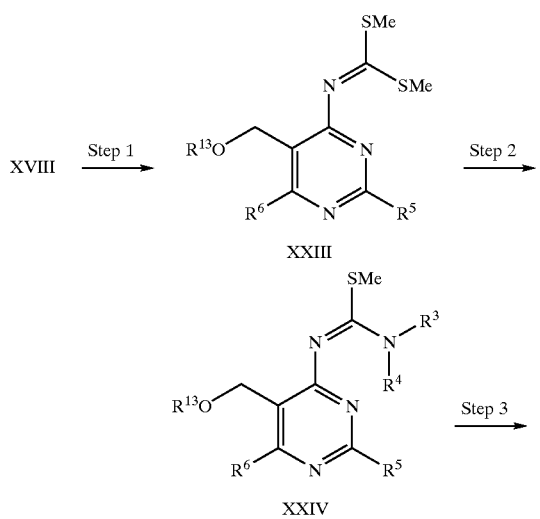

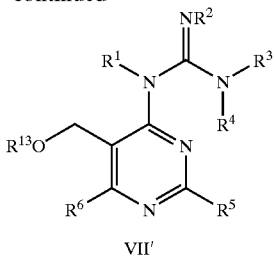

(Step 1)

Compound (XVIII) in a solvent such as dimethylformamide and tetrahydrofuran is reacted with a base such as sodium hydride and potassium butoxide at 0° C. to 100° C., preferably 20° C. to 60° C. for 0.5 h to 48 h, preferably 1 h to 12 h. To the mixture are added carbon disulfide and then methyl iodide and the resulting mixture is reacted at 0° C. to 100° C., preferably 20° C. to 60° C. for 0.5 h to 48 h, preferably 1 h to 12 h to give compound (XXII).

(Step 2)

Compound (XXIII) in a solvent such as methanol and dimethylformamide is reacted with $R^3R^4NH$ at 0° C. to 150° C., preferably 0° C. to 100° C. for 0.5 h to 48 h, preferably 1 h to 12 h to give compound (XXIV).

(Step 3)

Compound (XXIV) in a solvent such as methanol and dimethylformamide is reacted with $R^1R^2NH$ at 20° C. to 150° C., preferably 40° C. to 80° C. for 0.5 h to 48 h, preferably 4 h to 24 h to give compound (VII).

Method N: Introduction of a guanidino group ($R^1$=H)

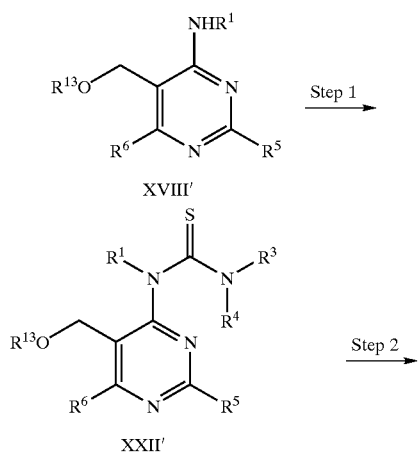

-continued (Step 1)
This step can be carried out in a manner similar to that described in step 1 of Method L.

(Step 2)
This step can be carried out in a manner similar to that described in step 2 of Method L.

When a compound contains a functional group(s) possibly interfering the reaction such as hydroxy, mercapto, and amino in the each step of Method A to Method N, it can previously be protected and deprotected at an appropriate stage in accordance with the literature such as Protective Groups in Organic Synthesis, Theodora W. Green (John Wiley & Sons).

In the specification, the term "solvate" includes, for example, solvates with organic solvents, hydrates, and the like.

The term "the compounds of the present invention" herein used includes pharmaceutically acceptable salts and hydrates of the compounds. For example, salts with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, maleic acid, fumaric acid, benzenesulfonic acid, and p-toluenesulfonic acid) and hydrates of them are exemplified. These salts and hydrates can be formed by usual methods. The hydrates may coordinate with an arbitrary number of water molecules.

Prodrug is a derivative of the compound of the present invention having a group which can be decomposed chemically or metabolically, and such prodrug is converted to a pharmaceutically active compound of the present invention by means of solvolysis or by placing the compound in vivo under a physiological condition. The selection method and the process method of an appropriate prodrug derivative are described in the literature such as Design of Prodrugs, Elsevier, Amsterdam 1985. When the compounds of the present invention have a carboxyl group, an ester derivative prepared by reacting a basal acid compound with a suitable alcohol or an amide prepared by reacting a basal acid compound with a suitable amine are exemplified as prodrugs. Particularly preferred esters as prodrugs are methyl ester, ethyl ester, n-propyl ester, isopropyl ester, n-butyl ester, isobutyl ester, tert-butyl ester, morpholinoethyl ester, N, N-diethylglycolamido ester, and the like. When the compounds of the present invention have a hydroxy group, an acyloxy derivative prepared by reacting with a suitable acyl halide or a suitable acid anhydride are exemplified as prodrugs. Particularly preferred acyloxy derivatives as prodrugs are —$OCOC_2H_5$, —$OCO'$—Bu, —$OCOC_{15}H_{31}$, —$OCO(m$—$COONa$—$Ph)$, —$OCOCH_2CH_2COONa$, —$OCOCH(NH_2)CH_3$, and —$OCOCH_2N(CH_3)_2$, and the like. When the compounds of the present invention have an amino group, an amide derivative prepared by reacting with a suitable acid halide or a suitable acid anhydride are exemplified as prodrugs. Particularly preferred amide derivatives as prodrugs are —NHCO(CH$_2$)$_{20}$CH$_3$ and —NHCOCH(NH$_2$)CH$_3$, and the like.

The compound of the present invention is not restricted to any particular isomers but includes all possible isomers and racemic modifications.

The compounds of the present invention have an inhibitory activity against a signal derived from Ras oncogene products as shown in the experimental examples below.

Consequently, the compounds of the present invention can be used as a therapeutic agent for cancer.

When the compound of this invention is administered to a patient for the treatment or prevention of the above diseases, it can be administered by oral administration such as powder, granules, tablets, capsules, pilulae, and liquid medicine, or by parenteral administration such as injections, suppository, percutaneous formulations, insufflation, or the like. An effective amount of the compound of tis invention is formulated by being mixed with appropriate medicinal admixture such as excipient, binder, penetrant, disintegrators, lubricant, and the like, if necessary. When parenteral injection is prepared, the compound of this invention and an appropriate carrier are sterilized to prepare it.

An appropriate dosage varies with the conditions of the patients, an administration route, their age, and their body weight. In the case of oral administration to an adult, the dosage can generally be between 0.01–100 mg/kg/day, preferably 0.1–20 mg/kg/day.

The following examples are provided to further illustrate the present invention and are not to be construed as limiting the scope thereof.

In the examples, the following abbreviations are used.
Me: methyl
Et : ethyl
Pr: n-propyl
i-Pr: isopropyl
Bu : n-butyl
i-Bu: isobutyl
tBu: tert-butyl
Ac: acetyl
Ph: phenyl
MPM: p-methoxyphenylmethyl
DMF: dimethylformamide
THF: tetrahydrofuran
DMSO: dimethylsulfoxide
TsOH: p-toluene sulfonic acid
TBS : tert-butyldimethylsilyl In $^1$H-NMR, the value of δ is represented by ppm, s is singlet, d is doublet, t is triplet, q is quartet, quit is quintet, sext is sextet, and br is broad. The value of J is represented by Hz.

EXAMPLE

Reference Example 1

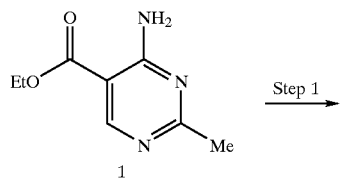

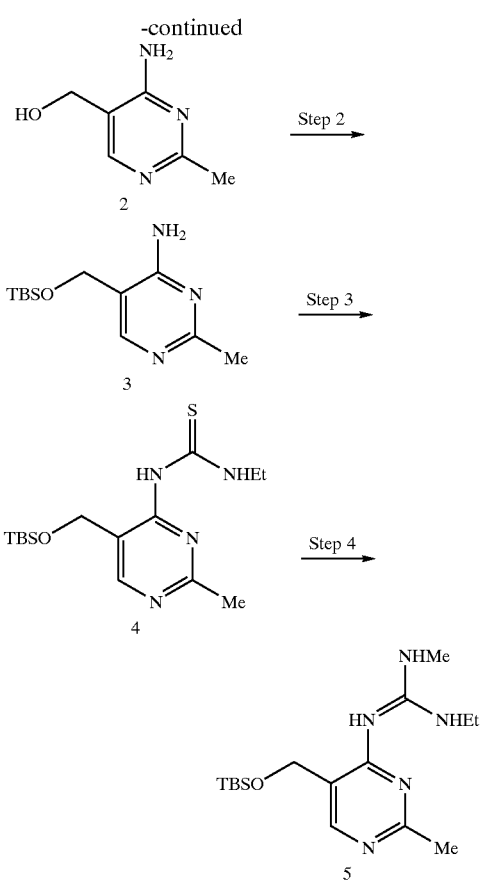

Step 1

To a suspension of lithium aluminum hydride (4.4 g) in 220 ml of THF was added dropwise a solution of compound 1 (22.0 g) which was obtained by well-known method (G. W. Kenner, B. Lythgoe, A. R. Todd and A. Topham, J. Chem. Soc., 388(1943)) in 220 ml of THF with stirring at ice-cooling. The reaction mixture was allowed to room temperature and stirred for 2 h. To the resulting mixture was added excess ice and stirred for an additional 2 h. Anhydrous sodium sulfate was added to the mixture and the precipitate was filtered off and washed with methanol. The combined filtrate was concentrated in vacuo and the residue was dissolved in ethanol with heating. The appeared insoluble material was filtered off and ethanol solution was allowed to cool. The insoluble material was filtered off again. The filtrate was diluted with diethyl ether and appeared crystal was filtered to give 14.5 g of compound 2.

Melting point: 119–121° C.; $^1$H-NMR(CDCl$_3$): 0.09(6H, s), 0.90(9H, s), 2.50(3H, s), 4.60(2H, s), 5.39(2H, br), 7.95(1H, s).

Step 2

To a solution of compound 2 (13.9 g) and 7.7g of imidazole in 200 ml of DMF was added 7.7 g of t-butyldimethylsilyl chloride with stirring at ice-cooling. The mixture was stirred over night and 2.0 g of imidazole and 3.4 g of t-butyldimethylsilyl chloride were added to the mixture. The mixture was stirred for 6 h and added ethyl acetate. The organic layer was washed with saturated aqueous sodium bicarbonate and brine, dried over anhydrous sodium sulfate, and concentrated in vacuo. Ethyl acetate was added to the residue and the mixture was diluted with hexane. The appeared crystal was filtered to give 12.8 g of compound 3.

Melting point: 119–121° C.; $^1$H-NMR(CDCl$_3$): 0.09(6H, s), 0.90(9H, s), 2.50(3H, s), 4.60(2h, s), 5.39(2H, br), 7.95(1H, s).

Step 3

To a suspension of 2.9 g of sodium hydride in 90 ml of DMF was added dropwise a solution of compound 3 (18.1 g) in 90 ml of DMF with stirring. The mixture was stirred for 1h and 6.3 ml of ethyl isothiocyanate was added to the mixture dropwise at ice-cooling. The resulting mixture was stirred for an additional 30 min at room temperature, ice-cooled, added 4.5 ml of acetic acid, and added ethyl acetate. The organic layer was washed with aqueous potassium hydrogen sulfate and brine, dried over anhydrous sodium sulfate, and concentrated in vacuo. The residue was subjected to silica gel column chromatography to give 15.8 g of compound 4.

Melting point: 86–87° C.; $^1$H-NMR(CDCl$_3$): 0.17(6H, s), 0.95(9H, s), 1.36(3H, t, J=7.3 Hz), 2.60(3H, s), 3.76(2H, dq, J=4.9, 7.3 Hz), 4.69(2H, s), 8.19(1H, s), 9.36(1H, br), 11.5(1H, br).

Step 4

To the mixture of compound 4 (8.0 g), 5.6 g of mercuric oxide (red), and 60 ml of methanol was added 40 % methylamine in methanol with stirring at room temperature. The resulting mixture was stirred for 4h and insoluble material was filtered off. The filtrate was concentrated in vacuo and methanol/diethyl ether was added to the residue. The insoluble material was filtered off and the solvent was concentrated in vacuo. Toluene/hexane was added to the residue to give 7.81 g of compound 5 as crystal.

Melting point: 150–151° C.; $^1$H-NMR(CDCl$_3$): 0.10(6H, s), 0.95(9H, s), 1.28(3H, t, J=7.0 Hz), 2.49(3H, s), 2.92(3H, d, J=4.9 Hz), 3.34(2H, quint, J=7.0 Hz), 4.76(2H, s), 8.30 (1H, s).

Reference Example 2

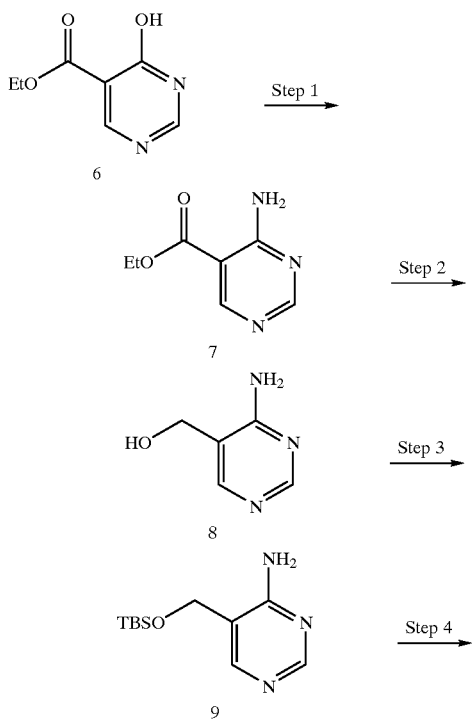

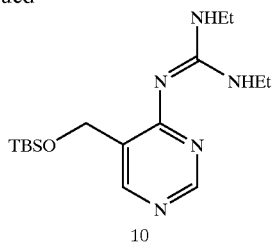

Step 1

To a solution of phosphorus oxychloride (61.5 g) in 35 ml of toluene was added 9.0 g of a sodium salt of compound 6 which was obtained by well-known method (A. Kreutzberger and C. Grundmann, J. Org. Chem., 26, 388 (1961)) and the resulting mixture was stirred for 1 h at 100° C. Excess phosphorus oxychlorde was removed under reduced pressure and 18 ml of 10% ammonia in ethanol was added to the mixture at 0° C. The mixture was stirred for 130 min at room temperature and insoluble material was removed. The solvent was concentrated in vacuo and the resulting residue was purified by column chromatography on silica gel to give 4.78 g of compound 7.

$^1$H-NMR(CDCl$_3$): 1.40(3H, t, J=7.3 Hz), 4.38(2H, q, J=7.3 Hz), 5.61(1H br), 7.86(1H, br), 8.62(1H, s), 8.90(1H, s).

Step 2

To a suspension of lithium aluminum hydride (1.19 g) in 30 ml of THF was added a solution of compound 7 (4.77 g) in 42 ml of THF at 0° C. and the resulting mixture was stirred for 1 h. A little water was added to the mixture and then stirred for an additional 50 min. The insoluble material was filtered off and the filtrate was concentrated in vacuo. Recrystallization from ethanol gave 1.77 g of compound 8.

$^1$H-NMR(CDCl$_3$): 4.65(2H, s), 8.09(1H, s), 8.54(1H, s).

Step 3

To a solution of compound 8 (1.63 g) in 13 ml of DMF was added a solution of 1.33 g of imidazole and 2.36 g of t-butyl dimethylsilyl chloride in 13 ml of DMF and the resulting mixture was stirred for 19 h at room temperature. Water was added to the reaction mixture and the mixture was extracted with ethyl acetate. The organic layer was washed with brine, dried, and concentrated in vacuo. The residue was purified by column chromatography on silica gel to give 2.68 g of compound 9.

$^1$H-NMR(CDCl$_3$): 0.10(6H, s), 0.90(9H, s), 4.62(2H, s), 5.43(2H, br), 8.04(1H, s), 8.51(1H, s).

Step 4

To a suspension of 1.67 g of sodium hydride in 10 ml of DMF was added a solution of compound 9 (4.00 g) and 3. 81 g of carbon disulfide in 40 ml of DMF. After stirring for 1 h at room temperature, to the mixture was added 7.11 g of methyl iodide and resulting mixture was stirred for an additional 4 h. To the mixture was added aqueous potassium hydrogen sulfate and the mixture was extracted with ethyl acetate. The organic layer was washed with brine, dried, and concentrated in vacuo. To the residue was added 70% ethtylamine solution (21.4 g) and the mixture was stirred for 15 h at 60° C. Excess ethylamine was removed under reduced pressure. The resulting residue was purified by column chromatography on silica gel to give 3.11 g of compound 10.

$^1$H-NMR(CDCl$_3$): 0.11(6H, s), 0.96(9H, s), 1.28(6H, t, J=7.3 Hz), 3.33(4H, dq, J=5.6, 7.3Hz), 4.77(2H, s), 8.38(1H, s), 8.52(1H, s).

Reference Example 3 Synthesis of Compound G-1

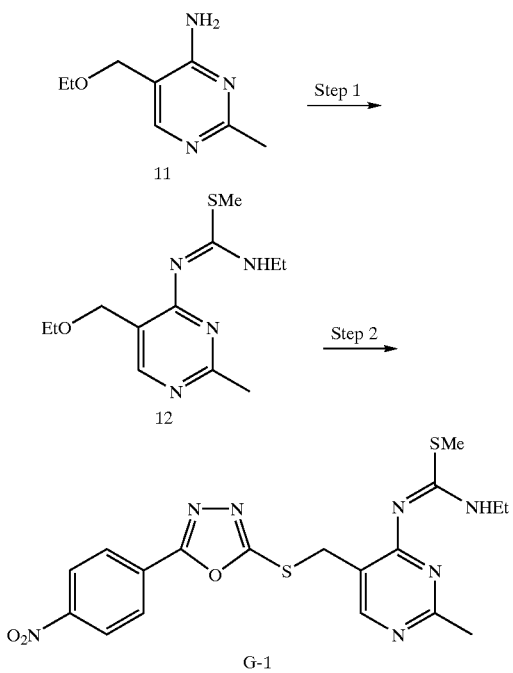

Step 1

To a solution of 4-amino-5-ethoxymethyl-2-methylpyrimidine 11 (1.0 g) which was obtained by well-known method (M. Tomita, S. Uyeo, A. Takamizawa, and R. Maeda, Yakugakuzassi, 74, 742 (1943)) and 0.74 g of potassium t-butoxide in 12 ml of DMF was added dropwise 0.58 ml of ethyl isothiocyanate with stirring at ice-cooling. After the addition was completed, the mixture was stirred for 1 h at room temperature. The disappearance of compound 11 was confirmed, then to the mixture was added 0.42 ml of methyl iodide at ice-cooling and the resulting mixture was stirred for 10 min at ice-cooling and for an additional 10 min at room temperature. The reaction mixture was extracted with ethyl acetate and the organic layer was washed with water and brine, dried over anhydrous magnesium sulfate, and concentrated in vacuo. The residue was subjected to silica gel column chromatography to yield 1.42 g of compound 12.

Melting point 52–53° C.; $^1$H-NMR(CDCl$_3$): 1.26(3H, t, J=6.9 Hz), 1.33(3H, t, J=7.3 Hz), 2.51(3H, s), 2.55(3H, s), 3.43(2H, dq, J=7.3, 5.3 Hz), 3.60(2H, q, J=6.9 Hz), 4.61(2H, s), 8.41(1H, s), 11.18(1H, br).

Step 2

Compound 12 was dissolved in 25 % solution of hydrogen bromide in acetic acid (35 ml) and the mixture was stirred for 8 h at 70° C. The solvent was removed under reduced pressure. The residue was dissolved in 15 ml of DMF and the resulting mixture was added to a suspension of 2-(4-nitrophenyl)-5-mercapto-1,3,4-oxadiazole (2.69 g) and potassium carbonate (6.05 g) in 15 ml of DMF. After the reaction mixture was stirred for 1.5 h at room temperature, water was added to the mixture. The precipitated crystal was collected by filtration to give 4.15 g of compound G-1.

Melting point 156–157° C.; $^1$H-NMR(CDCl$_3$): 1.35(3H, t, J=7.3 Hz), 2.55(3H, s), 2.57(3H, s), 3.45(2H, dq, J=7.3, 5.3Hz), 4.58(2H, s), 8.16(2H, d, J=8.7 Hz), 8.36(2H, d, J=8.7 Hz), 8.53(1H, s), 11.13(1H, br).

Example 1 Synthesis of Compound A-1

Compound 5 (6.5 g) was dissolved in 25% solution of hydrogen bromide in acetic acid and the mixture was stirred over night at 40° C. The solvent was removed under reduced pressure and the residue was dissolved in 43 ml of methanol. The mixture was added to a solution of 2-(2-aminophenyl)-5-mercapto-1,3,4-oxadiazole (11.9 g) which was obtained in accordance with the method described in R. W. Young and K. H. Wood, J. Am. Chem. Soc., 77, 400 (1955) and potassium hydroxide (3.3 g) in 54.5 ml of methanol at ice-cooling. The reaction mixture was stirred for 3 h at room temperature and insoluble material was removed by filtration. The solvent was removed under reduced pressure. To the residue was added dichloromethane and precipitate was removed by filtration. The solvent was removed under reduced pressure and the residue was subjected to silica gel column chromatography to give compound A-1. Further purification by the crystallization from diethyl ether gave 5.6 g of compound A-1. The physical data was shown in Table 1.

Example 2 Synthesis of Compound A-2

To a solution of compound A-1 (4.77 g) in 120 ml of pyridine was added dropwise 1.0 ml of acetyl chloride with stirring at ice-cooling. After 2.5 h, the mixture was warmed to room temperature and stirred for an additional 30 min. To the mixture was added about 5% of methanol in chloroform. The organic layer was washed with sat. sodium bicarbonate aq., dried over anhydrous sodium sulfate, and concentrated in vacuo. The residue was purified by column chromatography on silica gel to give 4.37 g of compound A-2. The physical data was shown in Table 1.

Example 3 Synthesis of Compound A-3

Compound 10 (0.17 g) was dissolved in 25% solution of hydrogen bromide in acetic acid (1 ml) and the mixture was stirred for 15 h at 40° C. The solvent was removed under reduced pressure and the residue was dissolved in 3 ml of DMF. The mixture was added to a solution of 2-(4-aminophenyl)-5-mercapto-1,3,4-oxadiazole (0.12 g) and potassium t-butoxide (0.2 g) in 1 ml of DMF at ice-cooling. The reaction mixture was stirred for 1 h at room temperature and extracted with ethyl acetate. The organic layer was washed with water and dried. The residue was purified by silica gel column chromatography to give 0.07 g of compound A-3. The physical data was shown in Table 1.

Example 4 Synthesis of Compound A-4

To a solution of 4-amino-5-ethoxymethyl-2-methylpyridine (4.8 g) which was obtained in accordance with the method described in M. Tomita, S. Uyeo, A. Takamizawa and R. Maeda, Yakugakuzasshi, 74, 742 (1954) in 48 ml of pyridine was added 4.2 g of methyl isothiocyanate and the resulting mixture was heated at reflux for 7 h. Additionally, 1.1 g of methyl isothiocyanate was added and the mixture was heated at reflux for 4 h. The solvent was removed under reduced pressure and the residue was purified by silica gel column chromatography to give 4.18 g of 4-(N'-methylthioureido)-5-ethoxymethyl-2-methylpyrimidine.

$^1$H-NMR (CDCl$_3$): 1.35(3H, t, J=7.0 Hz), 2.61(3H, s), 3.28(3H, d, J=4.9 Hz), 3.62(2H, q, J=7.0 Hz), 4.52(2H, s), 8.23(1H, s), 9.48(1H, br), 11.40(1H, br).

To a solution of 4-(N'-methylthioureido)-5-ethoxymethyl-2-methylpyrimidine(300 mg) in 6 ml of 10% ammonia—ethanol was added 400 mg of red mercuric oxide and the resulting mixture was stirred for 15 min at room temperature. After removing the insoluble material by filtration, crystallization from ethyl acetate gave 117 mg of 4-(methylguanidino)-5-ethoxymethyl–2-methylpyrimidine.

¹H-NMR (CDCl₃): 1.26(3H, t, J=7.0 Hz), 2.51(3H, s), 2.92(3H, s), 3.59(2H q, J=7.0 Hz), 4.52(2H, s), 6.49(1H, s), 8.25(1H, s).

A solution of 4-(methylguanidino)-5-ethoxymethyl-2-methylpyrimidine (500 mg) in 10 ml of 25% of hydrogen bromide in acetic acid was heated at reflux for 6 h. The solvent was removed under reduced pressure and the residue was dissolved in 14.5 ml of ethanol. To the mixture were added 2-(2-aminophenyl)-5-mercaptooxadiazole (290 mg) and potassium hydroxide (350 mg) and the resulting mixture was stirred for 2 h at ice-cooling. The insoluble material was removed by filtration and the filtrate was concentrated in vacuo. The residue was purified by silica gel column chromatography to give 210 mg of the desired compound. The physical data was shown in Table 1.

Example 5 Synthesis of Compound A-5

To a suspension of compound A-4 (200 mg) in 5 ml of methanol was added 5 ml of 10% hydrochloric acid in methanol and the resulting mixture was stirred for 5 min. The solvent was removed under reduced pressure and the residue was dissolved in ethanol. To the solution was added ethyl acetate and the precipitate was collected to give 193 mg of compound A-5.

The result of elemental analysis (C, H, N, Cl) showed the compound was dihydrochloride. The physical data was shown in Table 1.

Example 6–Example 190

Compounds A-6 to A-190 were synthesized in a manner similar to those described in Example 1 to 5. The physical data were shown in Tables 1 to 21. CDCl₃ was used when there is no description of the solvents for the ¹H-NMR spectrum.

TABLE 1

| Example No. | Compound No. | $R^{15}$ | $R^{16}$ | $R^{17}$ | $R^{18}$ | Salt | ¹H-NMR (δ) ppm |
|---|---|---|---|---|---|---|---|
| 1 | A-1 | Et | Me | Me | 2-NH₂ | — | 2.48(3H, s), 4.46(2H, s), 4.54(2H, s), 5.75(2H, br), 6.72(1H, ddd, J=8.1, 7.2, 0.9), 6.76(1H, dd, J=8.5, 0.9), 7.24(1H, ddd, J=8.5, 7.2, 1.5), 7.27–7.39(5H, m), 7.63(1H, dd, J=8.1, 1.5), 8.40(1H, s) |
| 2 | A-2 | Et | Me | Me | 2-NHAc | — | 1.31(3H, t, J=7.2), 2.31(3H, s), 2.49(3H, s), 2.98(3H, d, J=4.9), 3.41(2H, br.), 4.50(2H, s), 7.14(1H, t, J=8.1), 7.49(1H, ddd, J=8.5, 8.1, 1.6), 7.80(1H, dd, J=8.1, 1.6), 8.35(1H, s), 8.76(1H, d, J=8.5), 10.84(1H, br) |
| 3 | A-3 | Et | Et | H | 4-NH₂ | — | 1.30(6H, t, J=7.3), 3.38(4H, br), 4.01(2H, s), 4.45(2H, s), 6.71(2H, d, J=8.5), 7.77(2H, d, J=8.5), 8.39(1H, s), 8.54(1H, s) |
| 4 | A-4 | H | Me | Me | 2-NH₂ | — | 2.50(3H, s), 2.93(3H, s), 4.44(2H, s), 5.76(2H, br), 6.73(1H, t, J=7.8), 6.77(1H, d, J=7.8), 7.24(1H, t, J=7.8), 7.64(1H, d, J=7.8), 8.34(1H, s) |
| 5 | A-5 | H | Me | Me | 2-NH₂ | 2HCl | 2.60(3H, s), 2.93(3H, s), 4.47(2H, s), 6.98(1H, t, J=7.9), 7.07(1H, d, J=7.9), 7.45(1H, t, J=7.9), 7.67(1H, d, J=7.9), 8.48(1H, s) (in D₂O) |
| 6 | A-6 | H | Me | Me | 2-NH₂ | TsOH | 2.39(3H, s), 2.52(3H, s), 2.86(3H, s), 4.39(2H, s), 6.90(1H, t, J=7.8), 7.00(1H, d, J=7.8), 7.35(2H, t, J=8.4), 7.41(1H, t, J=7.8), 7.64(1H, d, J=7.8), 7.69(2H, d, J=8.4), 8.29(1H, s) (in D₂O) |
| 7 | A-7 | H | Me | Me | 2-NH₂, 5-Cl | — | 2.51(3H, s), 2.94(3H, s), 4.46(2H, s), 5.79(2H, br), 6.71(1H, d, J=8.7), 7.18(1H, dd, J=8.7, 2.5), 7.60(1H, d, J=2.5), 8.34(1H, s) |
| 8 | A-8 | H | Et | Me | 2-NH₂ | — | 1.31(3H, t, J=7.3), 2.51(3H, s), 3.33(2H, br), 4.47(2H, s), |

TABLE 1-continued

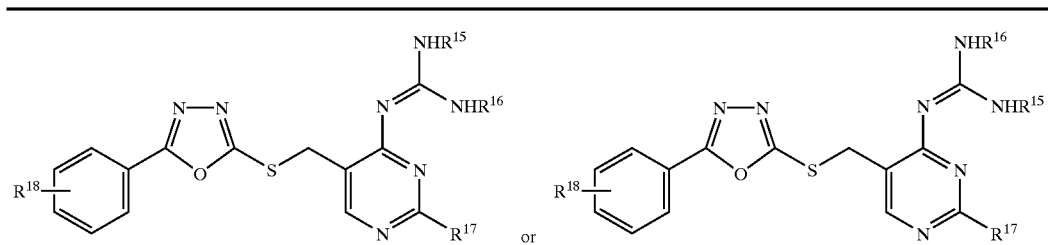

| Example No. | Compound No. | R15 | R16 | R17 | R18 | Salt | 1H-NMR (δ) ppm |
|---|---|---|---|---|---|---|---|
| | | | | | | | 5.76(2H, br), 6.72(1H, t, J=7.8), 6.77(1H, d, J=7.8), 7.24(1H, t, J=7.8), 7.64(1H, d, J=7.8), 8.38(1H, s) |

TABLE 2

| Example No. | Compound No. | R15 | R16 | R17 | R18 | Salt | 1H-NMR (δ) ppm |
|---|---|---|---|---|---|---|---|
| 9 | A-9 | H | Bu | Me | 2-NH$_2$ | — | 0.98(3H, t, J=7.3), 1.46(2H, sext, J=7.3), 1.65(2H, quint, J=7.3), 2.50(3H, s), 3.25(2H, br), 4.45(2H, s), 5.76(2H, br), 6.73(1H, ddd, J=7.9 7.0, 0.9), 6.77(1H, dd J=8.4, 0.9), 7.24(1H, ddd, J=8.4, 7.0, 1.5), 7.64(1H, dd, J=7.9, 1.5), 8.35(1H, s) |
| 10 | A-10 | H | Et | Me | 2-NH$_2$ | 2HCl | 1.25(3H, t, J=7.3), 2.58(3H, s), 3.26(2H, q, J=7.3), 4.44(2H, s), 6.96(1H, t, J=7.9), 7.05(1H, d, J=7.9), 7.44(1H, t, J=7.9), 7.66(1H, d, J=7.9), 8.45(1H, s) (in D$_2$O) |
| 11 | A-11 | H | 4-Cl—C$_6$H$_4$ | Me | 2-NH$_2$ | — | 2.53(3H, s), 4.49(2H, s), 5.76(2H, br), 6.73(1H, ddd, J=8.0, 7.0, 0.7), 6.77(1H, dd, J=8.3, 0.7), 7.22–7.26(3H, m), 7.39(2H, d, J=8.6), 7.65(1H, dd, J=8.0, 1.5), 8.44(1H, s) |
| 12 | A-12 | H | CH$_2$Ph | Me | 2-NH$_2$ | — | 2.48(3H, s), 4.46(2H, s), 4.54(2H, s), 5.75(2H, br), 6.72(1H, ddd, J=8.1, 7.2, 0.9), 6.76(1H, dd, J=8.5, 0.9), 7.24(1H, ddd, J=8.5, 7.2, 1.5), 7.27–7.39(5H, m), 7.63(1H, dd, J=8.1, 1.5), 8.40(1H, s) |
| 13 | A-13 | Et | 1-pyrrolidinyl | Me | 2-NH$_2$ | — | 1.21(3H, t, J=7.2), 2.00(4H, br), 2.53(3H, s), 3.27(2H, dq, J=5.6, 7.2), 3.50(4H, br), 4.30(2H, s), 5.79(2H, br), 6.73(1H, dd, J=8.0, 7.1), 6.79(1H, d, J=8.3), 7.25(1H, ddd, J=8.3, 7.1, 1.5), 7.64(1H, dd, J=8.0, 1.5), 7.98(1H, s) |
| 14 | A-14 | H | Et | Me | 2-NHSO$_2$(4-MeOC$_6$H$_4$) | — | 1.30(3H, t, J=7.3), 2.51(3H, s), 3.30(2H, br), 3.78(3H, s), 4.46(2H, s), 6.83(2H, d, J=9.0), 7.10(1H, t, J=7.8), 7.41(1H, t, J=7.8), 7.67(1H, d, J=7.8), 7.77–7.81(3H, m), 8.37(1H, s), 10.41(1H, br) |
| 15 | A-15 | Et | Ac | Me | 2-NH$_2$ | — | 1.28(3H, t, J=7.2), 2.23(3H, s), 2.55(3H, s), 3.55(2H, dq, J=5.6, 7.2), 4.48(2H, s), 5.76(2H, br), 6.72(1H, t, J=7.9), 6.77(1H, d, J=7.9), 7.24(1H, dt, J=1.5, 7.9), 7.63(1H, dd, J=7.9, 1.5), 8.48(1H, s), 8.84(1H, br), 14.12(1H, br) |

TABLE 3

| Example No. | Compound No. | $R^{15}$ | $R^{16}$ | $R^{17}$ | $R^{18}$ | $^1$H-NMR ($\delta$) ppm |
|---|---|---|---|---|---|---|
| 16 | A-16 | Et | Ac | Me | 2-NHAc | 1.29(3H, t, J=7.3), 2.24(3H, s), 2.32(3H, s), 2.56(3H, s), 3.57(2H, dq, J=5.6, 7.3), 4.50(2H, s), 7.14(1H, ddd, J=8.1, 7.1, 1.1), 7.50(1H, ddd, J=8.6, 7.1, 1.5), 7.80(1H, dd, J=8.1, 1.5), 8.51(1H, s), 8.76(1H, dd, J=8.6, 1.1), 8.88(1H, br), 10.80(1H, br), 14.11(1H, br) |
| 17 | A-17 | H | Et | Me | 2-NHCOPh | 1.28(3H, t, J=7.2), 2.50(3H, s), 3.29(2H, q, J=7.2), 4.48(2H, s), 7.20(1H, t, J=7.9), 7.55–7.59(4H, m), 7.86(1H, dd, J=7.9, 1.5), 8.16–8.18 (2H, m), 9.00(1H, d, J=7.9), 11.68(1H, br) |
| 18 | A-18 | H | Et | Me | 2-NHAc | 1.31(3H, t, J=7.2), 2.31(3H, s), 2.51(3H, s), 3.26(2H, q, J=7.2), 4.48(2H, s), 7.14(1H, dd, J=8.0, 7.5), 7.50(1H, ddd, J=8.6, 7.5, 1.5), 7.80(1H, dd J=8.0, 1.5), 8.39(1H, s), 8.76(1H, d, J=8.6), 10.84(1H, br) |
| 19 | A-19 | H | Me | Me | 2-NHAc | 2.31(3H, s), 2.51(3H, s), 2.95(3H, s), 4.48(2H, s), 7.14(1H, t, J=7.8), 7.50(1H, ddd, J=8.5, 7.8, 1.5), 7.79(1H, dd J=7.8, 1.5), 8.39(1H, s), 8.76(1H, d, J=8.5), 10.84(1H, br) |
| 20 | A-20 | H | Me | Me | 2-NHCOEt | 1.31(3H, t, J=7.6), 2.51(3H, s), 2.57(2H, q, J=7.6), 2.95(3H, s), 4.52(2H, s), 7.13(1H, dd, J=7.9, 7.1), 7.49(1H, ddd, J=8.7, 7.1, 1.7), 7.78(1H, dd, J=7.9, 1.7), 8.42(1H, s), 8.77(1H, d, J=8.7), 10.82(1H, br) |
| 21 | A-21 | Et | Me | Me | H | 1.30(3H, t, J=7.2), 2.49(3H, s), 2.97(3H, br), 3.40(2H, br), 4.49(2H, s), 7.45–7.51(3H, m), 7.97–7.99(2H, m), 8.36(1H, s) |
| 22 | A-22 | H | Et | Me | 2-NHCOEt | 1.31(3H, t, J=7.2), 1.32(3H, t, J=7.6), 2.51(3H, s), 2.56(2H, q, J=7.6), 3.31(2H, q, J=7.2), 4.48(2H, s), 7.14(1H, t, J=7.9), 7.50(1H, dt, J=1.6, 7.9), 7.80(1H, dd, J=7.9, 1.6), 8.39(1H, s), 8.79(1H, d, J=7.9), 10.83(1H, br) |
| 23 | A-23 | Et | Me | Me | 2-NHCOEt | 1.31(3H, t, J=7.1), 1.32(3H, t, J=7.6), 2.49(3H, s), 2.56(2H, q, J=7.6), 2.98(3H, d, J=4.7), 3.40(2H, br), 4.50(2H, s), 7.13(1H, t, J=7.8), 7.49(1H, t, J=7.8), 7.80(1H, d, J=7.8), 8.35(1H, s), 8.79(1H, d, J=7.8) |

TABLE 4

| Example No. | Compound No. | $R^{15}$ | $R^{16}$ | $R^{17}$ | $R^{18}$ | $^1$H-NMR ($\delta$) ppm |
|---|---|---|---|---|---|---|
| 24 | A-24 | Et | Et | Me | 2-NH$_2$ | 1.30(6H, t, J=7.2), 2.48(3H, s), 3.38(4H, br), 4.47(2H, s), 5.76(2H, br), 6.72(1H, dd, J=8.1, 7.1), 6.77(1H, d, J=8.5), 7.24(1H, ddd, J=8.5, 7.1, 1.5), 7.64(1H, dd, J=8.1, 1.5), 8.33(1H, s) |
| 25 | A-25 | Et | Et | Me | 2-NHAc | 1.31(6H, t, J=7.2), 2.31(3H, s), 2.48(3H, s), 3.38(4H, br), 4.49(2H, s), 7.14(1H, ddd, J=8.1, 7.1, 1.0), 7.49(1H, ddd, J=8.5, 7.1, 1.7), 7.80(1H, dd, J=8.1, 1.7), 8.35(1H, s), 8.76(1H, dd, J=8.5, 1.0), 10.8(1H, br) |
| 26 | A-26 | Et | Et | Me | 2-NHCOEt | 1.31(6H, t, J=7.2), 1.32(3H, t, J=7.6), 2.48(3H, s), 2.57(2H, q, J=7.6), 3.38(4H, br), 4.49(2H, s), 7.13(1H, ddd, J=8.1, 7.1, 1.0), 7.49(1H, ddd, J=8.5, 7.1, 1.5), 7.80(1H, dd, J=8.1, 1.5), 8.35(1H, s), 8.79(1H, dd, J=8.5, 1.0), 10.8(1H, br) |

TABLE 4-continued

| Example No. | Compound No. | R¹⁵ | R¹⁶ | R¹⁷ | R¹⁸ | ¹H-NMR (δ) ppm |
|---|---|---|---|---|---|---|
| 27 | A-27 | Et | Me | Me | 2-OH | 1.30(3H, t, J=7.2), 2.49(3H, s), 2.97(3H, d, J=4.6), 3.39(2H, br), 4.49(2H, s), 6.97(1H, ddd, J=7.8, 7.1, 1.2), 7.10(1H, dd, J=8.5, 1.2), 7.41(1H, ddd, J=8.5, 7.1, 1.7), 7.65(1H, dd, J=7.8, 1.7), 8.33(1H, s), 9.95(1H, s) |
| 28 | A-28 | Et | Me | Me | 2-OCH₂CO₂Et | 1.26(3H, t, J=7.2), 1.30(3H, t, J=7.2), 2.48(3H, s), 2.97(3H, t, J=4.4), 3.40(2H, br), 4.25(2H, q, J=7.2), 4.49(2H, s), 4.77(2H, s), 6.92(1H, d, J=8.3), 7.10(1H, t, J=7.7), 7.45(1H, ddd, J=8.3, 7.7, 1.7), 7.92(1H, dd, J=7.7, 1.7), 8.33(1H, s) |
| 29 | A-29 | Et | Me | Me | 2-NHSO₂Me | 1.30(3H, t, J=7.2), 2.49(3H, s), 2.97(3H, d, J=4.6), 3.07(3H, s), 3.40(2H, br), 4.49(2H, s), 7.20(1H, t, J=7.9), 7.51(1H, td, J=7.9, 1.5), 7.83(1H, dd, J=7.9, 1.5), 7.85(1H, d, J=7.9), 8.33(1H, s) |
| 30 | A-30 | —CH₂—CH₂— | | Me | 2-NH₂ | 2.52(3H, s), 3.68(4H, s), 4.43(2H, s), 5.76(2H, br), 6.73(1H, t, J=7.8), 6.77(1H, d, J=7.8), 7.24(1H, t, J=7.8), 7.64(1H, d, J=7.8), 8.36(1H, s) |
| 31 | A-31 | Et | Me | Me | 2-OCH₂CO₂H | 1.19(3H, t, J=7.1), 2.53(3H, s), 2.97(3H, br), 3.45(2H, br), 4.75(2H, s), 5.16(2H, s), 7.03(1H, t, J=7.6), 7.29(1H, d, J=8.4), 7.42(1H, dd, J=8.4, 7.6), 8.05(1H, d, J=7.6), 8.73(1H, s) (in C₅D₅N) |

TABLE 5

| Example No. | Compound No. | R¹⁵ | R¹⁶ | R¹⁷ | R¹⁸ | ¹H-NMR (δ) ppm |
|---|---|---|---|---|---|---|
| 32 | A-32 | Et | Et | Ph | 2-NH₂ | 1.36(6H, t, J=7.3), 3.42(4H, br), 4.55(2H, s), 5.77(2H, br), 6.72(1H, t, J=7.9), 6.77(1H, d, J=7.9), 7.24(1H, t, J=7.9), 7.43–7.46(3H, m), 7.65(1H, dd, J=7.9, 1.4), 8.18–8.20(2H, m), 8.53(1H, s) |
| 33 | A-33 | Et | Et | H | 2-NH₂ | 1.31(6H, t, J=7.2), 3.39(4H, br), 4.48(2H, s), 5.77(2H, br), 6.72(1H, dd, J=8.3, 7.8), 6.78(1H, d, J=8.3), 7.24(1H, m), 7.65(1H, d, J=7.8), 8.41(1H, s), 8.55(1H, s) |
| 34 | A-34 | Et | Et | SMe | 2-NH₂ | 1.29(6H, t, J=7.3), 2.48(3H, s), 3.38(4H, br), 4.44(2H, s), 5.77(2H, br), 6.69–6.79(2H, m), 7.23(1H, d, J=8.0), 7.65(1H, dd, J=8.0, 1.5), 8.24(1H, s) |
| 35 | A-35 | Et | Et | OH | 2-NH₂ | 1.30(6H, t, J=7.1), 3.39(4H, br), 4.30(2H, s), 5.74(2H, br), 6.73(1H, ddd, J=8.3, 8.1, 1.0), 6.77(1H, d, J=8.3), 7.25(1H, td, J=8.1, 1.0), 7.57(1H, s), 7.64(1H, dd, J=8.1, 1.5), 8.84(1H, br) |
| 36 | A-36 | Et | Pr | Me | 2-NH₂ | 1.04(3H, t, J=7.3), 1.30(3H, t, J=7.2), 1.71(2H, sext, J=7.3), 3.28(2H, br), 3.41(4H, br), 4.46(2H, s), 5.76(2H, br), 6.72(1H, ddd, J=8.1, 7.1, 0.9), 6.77(1H, dd, J=8.4, 0.9), 7.24(1H, ddd, J=8.4, 7.1, 1.7), 7.65(1H, dd, J=8.1, 1.7), 8.32(1H, s) |
| 37 | A-37 | Et | Et | Et | 2-NH₂ | 1.29(6H, t, J=7.5), 1.30(3H, t, J=7.4), 2.78(2H, q, J=7.4), 3.37(4H, br), 4.47(2H, s), 5.77(2H, br), 6.73–6.77(2H, m), 7.24(1H, t, J=8.1), 7.64(1H, dd, J=8.1, 1.5), 8.35(1H, s) |
| 38 | A-38 | Et | Me | Me | 2-NHMe | 1.30(3H, t, J=7.2), 2.48(3H, s), 2.97(3H, d, J=4.6), 2.99(3H, d, J=4.9), 3.39(2H, br), 4.47(2H, s), |

TABLE 5-continued

| Example No. | Compound No. | $R^{15}$ | $R^{16}$ | $R^{17}$ | $R^{18}$ | $^1$H-NMR ($\delta$) ppm |
|---|---|---|---|---|---|---|
| | | | | | | 6.68(1H, t, J=8.1), 6.74(1H, d, J=8.5), 7.35(1H, ddd, J=8.5, 8.1, 1.6), 7.36(1H, br), 7.67(1H, dd, J=8.1, 1.6), 8.32(1H, s) |
| 39 | A-39 | Et | Me | Me | 2-NMe$_2$ | 1.30(3H, t, J=7.2), 2.49(3H, s), 2.76(6H, s), 2.97(3H, d, J=4.9), 3.40(2H, br), 4.47(2H, s), 6.97(1H, t, J=7.7), 7.06(1H, d, J=8.3), 7.40(1H, ddd, J=8.3, 7.7, 1.7), 7.72(1H, dd, J=7.7, 1.7), 8.33(1H, s) |

TABLE 6

| Example No. | Compound No. | $R^{15}$ | $R^{16}$ | $R^{17}$ | $R^{18}$ | $^1$H-NMR ($\delta$) ppm |
|---|---|---|---|---|---|---|
| 40 | A-40 | Et | Me | Me | 2-NHEt | 1.30(3H, t, J=7.1), 1.37(3H, t, J=7.1), 2.49(3H, s), 2.98(3H, br), 3.32(2H, dq, J=5.1, 7.1), 3.40(2H, br), 4.47(2H, s), 6.66(1H, t, J=7.4), 6.75(1H, d, J=8.7), 7.32(1H, ddd, J=8.7, 7.4, 1.7), 7.33(1H, br), 7.67(1H, dd, J=7.4, 1.7), 8.33(1H, s) |
| 41 | A-41 | Et | Et | Me | 3-NH$_2$ | 1.30(6H, t, J=7.2), 2.48(3H, s), 3.37(4H, br), 3.83(2H, br), 4.46(2H, s), 6.80(1H, ddd, J=8.1, 2.4, 1.0), 7.22–7.35(3H, m), 8.32(1H, s) |
| 42 | A-42 | Et | Et | Me | 4-NH$_2$ | 1.29(6H, t, J=7.2), 2.48(3H, s), 3.37(4H, br), 4.00(2H, br), 4.38(2H, s), 6.71(2H, d, J=8.5), 7.76(2H, d, J=8.5), 8.30(1H, s) |
| 43 | A-43 | Et | Et | Me | 2-NH$_2$-3-Cl | 1.30(6H, t, J=7.3), 2.48(3H, s), 3.37(4H, br), 4.47(2H, s), 6.31(2H, br), 6.67(1H, t, J=6.9), 7.36(1H, dd, J=6.9, 1.5), 7.59(1H, dd, J=6.9, 1.5), 8.33(1H, s) |
| 44 | A-44 | Et | Et | Me | 2-NH$_2$-4-Cl | 1.30(6H, t, J=7.3), 2.48(3H, s), 3.37(4H, br), 4.46(2H, s), 5.88(2H, s), 6.69(1H, dd, J=7.6, 1.8), 6.77(1H, d, J=1.8), 7.56(1H, d, J=7.6), 8.31(1H, s) |
| 45 | A-45 | Et | Et | Me | 2-NH$_2$-6-Cl | 1.30(6H, t, J=7.2), 2.48(3H, s), 3.39(4H, br), 4.67(2H, s), 5.62(2H, br), 6.67(1H, dd, J=8.1, 1.0), 6.79(1H, dd, J=8.1, 1.0), 7.11(1H, t, J=8.1), 8.23(1H, s) |
| 46 | A-46 | Et | Et | CF$_3$ | 2-NH$_2$ | 1.32(6H, t, J=7.2), 3.39(4H, br), 4.48(2H, s), 5.76(2H, br), 6.70(1H, ddd, J=8.5, 7.8, 1.0), 6.77(1H, dd, J=8.3, 1.0), 7.24(1H, ddd, J=8.5, 8.3, 1.5), 7.63(1H, dd, J=7.8, 1.5), 8.50(1H, s) |
| 47 | A-47 | Et | Et | Me | 2-NH$_2$-5-Cl | 1.30(6H, t, J=7.2), 2.48(3H, s), 3.37(4H, br), 4.47(2H, s), 5.80(2H, br), 6.71(1H, d, J=8.8), 7.18(1H, dd, J=8.8, 2.4), 7.60(1H, d, J=2.4), 8.31(1H, s) |
| 48 | A-48 | Et | Et | CF$_3$ | 2-NHAc | 1.32(6H, t, J=7.2), 2.32(3H, s), 3.39(4H, br), 4.50(2H, s), 7.14(1H, ddd, J=8.0, 7.8, 1.0), 7.50(1H, ddd, J=8.5, 8.0, 1.5), 7.79(1H, dd, J=7.8, 1.5), 8.54(1H, s), 8.76(1H, dd, J=8.5, 1.0), 10.81(1H, s) |
| 49 | A-49 | Et | Et | Me | 2-NH$_2$-4-F | 1.30(6H, t, J=7.3), 2.47(3H, s), 3.37(4H, br), 4.45(2H, s), 5.93(2H, br), 6.43(1H, m), 6.47(1H, s), 7.62(1H, dd, J=9.8, 6.1), 8.31(1H, s) |

TABLE 7

| Example No. | Compound No. | R¹⁵ | R¹⁶ | R¹⁷ | R¹⁸ | ¹H-NMR (δ) ppm |
|---|---|---|---|---|---|---|
| 50 | A-50 | Et | Et | Me | 2-NH$_2$-5-F | 1.30(6H, t, J=7.3), 2.48(3H, s), 3.38(4H, br), 4.47(2H, s), 5.63(2H, br), 6.72(1H, dd, J=9.2, 4.3), 6.99(1H, m), 7.33(1H, dd, J=9.2, 3.1), 8.32(1H, s) |
| 51 | A-51 | Et | Et | Me | 2-NH$_2$-6-F | 1.31(6H, t, J=7.3), 2.47(3H, s), 3.40(4H, br), 4.45(2H, s), 6.01(2H, br), 6.04–6.56(2H, m), 7.16(1H, dt, J=7.9, 6.1), 8.33(1H, s) |
| 52 | A-52 | Et | Et | Me | 2-NH$_2$-4,5-F$_2$ | 1.31(6H, t, J=7.3), 2.48(3H, s), 3.40(4H, br), 4.46(2H, s), 5.78(2H, br), 6.55(1H, dd, J=12.2, 6.7), 7.43(1H, dd, J=10.4, 8.5), 8.31(1H, s) |
| 53 | A-53 | Et | Et | Me | 2-NH$_2$-3-Me | 1.30(6H, t, J=7.3), 2.23(3H, s), 2.48(3H, s), 3.38(4H, br), 4.47(2H, s), 5.83(2H, br), 6.67(1H, t, J=7.9), 7.16(1H, d, J=7.9), 7.56(1H, d, J=7.9), 8.33(1H, s) |
| 54 | A-54 | Et | Et | Me | 2-NH$_2$-5-Me | 1.30(6H, t, J=7.3), 2.26(3H, s), 2.48(3H, s), 3.37(4H, br), 4.47(2H, s), 5.60(2H, br), 6.69(1H, d, J=8.5), 7.06(1H, d, J=8.5), 7.44(1H, s), 8.32(1H, s) |
| 55 | A-55 | Et | Et | Me | 2-NH$_2$-6-Me | 1.30(6H, t, J=7.3), 2.45(3H, s), 2.48(3H, s), 3.38(4H, br), 4.47(2H, s), 5.62(2H, br), 6.57(1H, d, J=7.9), 6.62(1H, d, J=7.9), 7.10(1H, t, J=7.9), 8.32(1H, s) |
| 56 | A-56 | Et | Et | Me | 4-NHAc | 1.30(6H, t, J=7.1), 2.21(3H, s), 2.47(3H, s), 3.38(4H, br), 4.46(2H, s), 7.63(2H, d, J=8.6), 7.94(2H, d, J=8.6), 8.31(1H, s) |
| 57 | A-57 | Et | Et | H | 2-NHAc | 1.31(6H, t, J=7.3), 2.32(3H, s), 3.39(4H, br), 4.50(2H, s), 7.14(1H, ddd, J=7.8, 7.6, 1.0), 7.49(1H, ddd, J=8.5, 7.6, 1.5), 7.80(1H, dd, J=7.6, 1.5), 8.43(1H, s), 8.55(1H, s), 8.76(1H, dd, J=8.5, 1.0), 10.83(1H, s) |
| 58 | A-58 | Et | Et | Me | 2-NHMe | 1.30(6H, t, J=7.2), 2.48(3H, s), 2.99(3H, d, J=5.1), 3.38(4H, br), 4.46(2H, s), 6.68(1H, ddd, J=7.9, 7.1, 1.0), 6.74(1H, dd, J=8.5, 1.0), 7.35(1H, ddd, J=8.5, 7.1, 1.5), 7.36(1H, br), 7.67(1H, dd, J=7.9, 1.5), 8.32(1H, s) |
| 59 | A-59 | Et | Et | Me | 2-NMeAc | 1.31(6H, t, J=7.2), 1.75(3H, s), 2.47(3H, s), 3.19(3H, s), 3.38(4H, br), 4.48(2H, s), 7.33(1H, dd, J=7.8, 1.4), 7.50(1H, dt, J=1.4, 7.8), 7.59(1H, dt, J=1.4, 7.8), 8.06(1H, dd, J=7.8, 1.4), 8.33(1H, s) |

TABLE 8

| Example No. | Compound No. | R¹⁵ | R¹⁶ | R¹⁷ | R¹⁸ | ¹H-NMR (δ) ppm |
|---|---|---|---|---|---|---|
| 60 | A-60 | Et | Et | Me | 2-NHAc-4-F | 1.31(6H, t, J=7.3), 2.32(3H, s), 2.48(3H, s), 3.38(4H, br), 4.48(2H, s), 6.84(1H, m), 7.78(1H, dd, J=9.1, 6.1), 8.34(1H, s), 8.60(1H, dd, J=11.6, 2.4), 11.0(1H, s) |
| 61 | A-61 | Et | Et | Me | 2-NHAc-4-Cl | 1.31(6H, t, J=7.3), 2.31(3H, s), 2.48(3H, s), 3.38(4H, br), 4.48(2H, s), 7.12(1H, dd, J=8.5, 1.8), 7.71(1H, d, J=8.5), 8.34(1H, s), 8.88(1H, d, J=1.8), 10.91(1H, s) |
| 62 | A-62 | Et | Et | Me | 4-Cl | 1.30(6H, t, J=7.3), 2.48(3H, s), 3.38(4H, br), 4.47(2H, s), 7.46(2H, d, J=8.5), 7.92(2H, d, J=8.5), 8.32(1H, s) |
| 63 | A-63 | Et | Et | Me | 2-NH$_2$-4-Me | 1.30(6H, t, J=7.3), 2.29(3H, s), 2.48(3H, s), 3.37(4H, br), 4.46(2H, s), 5.69(2H, s), 6.55(1H, d, J=8.5), |

TABLE 8-continued

| Example No. | Compound No. | $R^{15}$ | $R^{16}$ | $R^{17}$ | $R^{18}$ | $^1$H-NMR ($\delta$) ppm |
|---|---|---|---|---|---|---|
| 64 | A-64 | Et | Et | Me | 4-NH$_2$-2-Cl | 6.58(1H, s), 7.52(1H, d, J=8.5), 8.31(1H, s)<br>1.29(6H, t, J=7.3), 2.47(3H, s), 3.37(4H, br), 4.08(2H, br), 4.45(2H, s), 6.60(1H, dd, J=8.5, 2.5), 6.76(1H, d, J=1.8), 7.70(1H, d, J=8.5), 8.31(1H, s) |
| 65 | A-65 | Et | Et | H | 2-NH$_2$-4-F | 1.30(6H, t, J=7.3), 3.38(4H, br), 4.47(2H, s), 5.94(2H, br), 6.40–6.47(2H, m), 7.62(1H, dd, J=9.2, 6.1), 8.40(1H, s), 8.55(1H, s) |
| 66 | A-66 | Et | Et | H | 4-NHMe | 1.30(6H, t, J=7.3), 2.89(3H, d, J=4.3), 3.38(4H, br), 4.14(1H, s), 4.45(2H, s), 6.62(2H, d, J=9.2), 7.79(2H, d, J=9.2), 8.39(1H, s), 8.54(1H, s) |
| 67 | A-67 | Et | Et | H | 4-NMe$_2$ | 1.29(6H, t, J=7.3), 3.04(6H, s), 3.38(4H, br), 4.45(2H, s), 6.71(2H, d, J=9.2), 7.82(2H, d, J=9.2), 8.39(1H, s), 8.54(1H, s) |
| 68 | A-68 | Et | Et | H | 4-NHEt | 1.28(3H, t, J=7.3), 1.29(6H, t, J=7.3), 3.14–3.27(2H, m), 3.37(4H, br), 3.99(1H, br), 4.45(2H, s), 6.61(2H, d, J=8.5), 7.77(2H, d, J=8.5), 8.38(1H, s), 8.54(1H, s) |
| 69 | A-69 | Et | Et | H | 4-NEt$_2$ | 1.20(6H, t, J=7.3), 1.29(6H, t, J=7.3), 3.41(4H, q, J=7.3), 3.38(4H, br), 4.44(2H, s), 6.67(2H, d, J=9.2), 7.79(2H, d, J=9.2), 8.39(1H, s), 8.54(1H, s) |

TABLE 9

| Example No. | Compound No. | $R^{15}$ | $R^{16}$ | $R^{17}$ | $R^{18}$ | $^1$H-NMR ($\delta$) ppm |
|---|---|---|---|---|---|---|
| 70 | A-70 | Me | Me | Me | 2-NH$_2$ | 2.50(3H, s), 2.98(6H, d, J=3.7), 4.49(2H, s), 5.76(2H, br), 6.72(1H, ddd, J=8.1, 7.2, 1.0), 6.77(1H, dd, J=8.4, 1.0), 7.24(1H, ddd, J=8.4, 7.2, 1.5), 7.64(1H, dd, J=8.1, 1.5), 8.33(1H, s) |
| 71 | A-71 | Et | Et | Me | 4-NH$_2$-3-Me | 1.29(6H, t, J=7.3), 2.20(3H, s), 2.48(3H, s), 3.37(4H, br), 3.95(2H, s), 4.44(2H, s), 6.66(1H, d, J=8.5), 7.64(2H, d, J=8.5, 1.8), 7.69(1H, s), 8.30(1H, s) |
| 72 | A-72 | Et | Et | Me | 4-NH$_2$-3-OMe | 1.30(6H, t, J=7.3), 2.48(3H, s), 3.37(4H, br), 3.92(3H, s), 4.17(2H, s), 4.43(2H, s), 6.71(1H, d, J=8.5), 7.37–7.48(2H, m), 8.30(1H, s) |
| 73 | A-73 | Et | Et | Me | 4-OMe | 1.30(6H, t, J=7.3), 2.48(3H, s), 3.38(4H, br), 3.87(3H, s), 4.46(2H, s), 6.98(2H, d, J=8.5), 7.92(2H, d, J=8.5), 8.31(1H, s) |
| 74 | A-74 | Et | Et | Me | 4-Me | 1.30(6H, t, J=7.3), 2.41(3H, s), 2.48(3H, s), 3.38(4H, br), 4.46(2H, s), 7.28(2H, d, J=8.5), 7.86(2H, d, J=8.5), 8.32(1H, s) |
| 75 | A-75 | Et | Et | Me | 2-NH$_2$-4-NO$_2$ | 1.31(6H, t, J=7.2), 2.49(3H, s), 3.38(4H, br), 4.49(2H, s), 6.17(2H, br), 7.52(1H, dd, J=8.8, 2.1), 7.63(1H, d, J=2.1), 7.79(1H, d, J=8.8), 8.34(1H, s) |
| 76 | A-76 | Et | Et | Me | 2,4-(NH$_2$)$_2$ | 1.17(6H, t, J=7.2), 2.35(3H, s), 3.30(4H, br), 4.32(2H, s), 5.43(2H, br), 5.96–5.98(2H, m), 6.25(2H, br), 7.24(1H, d, J=9.3), 8.11(1H, s)<br>(in DMSOd6) |
| 77 | A-77 | Et | Et | Me | 2-Cl | 1.30(6H, t, J=7.3), 2.48(3H, s), 3.38(4H, br), 4.48(2H, s), 7.34–7.55(3H, m), 7.93(1H, dd, J=7.3, 1.2), 8.33(1H, s) |
| 78 | A-78 | Et | Et | Me | 2-Me | 1.30(6H, t, J=7.3), 2.49(3H, s), 2.68(3H, s), 3.38(4H, br), 4.48(2H, s), |

TABLE 9-continued

| Example No. | Compound No. | $R^{15}$ | $R^{16}$ | $R^{17}$ | $R^{18}$ | $^1$H-NMR ($\delta$) ppm |
|---|---|---|---|---|---|---|
| | | | | | | 7.28–7.41(3H, m), 7.83(1H, dd, J=7.9, 1.8), 8.35(1H, s) |
| 79 | A-79 | Et | Et | Me | 2,3-Cl$_2$ | 1.30(6H, t, J=7.3), 2.48(3H, s), 3.37(4H, br), 4.48(2H, s), 7.56(1H, d, J=8.5), 7.82(1H, dd, J=8.5, 1.8), 8.06(1H, d, J=1.8), 8.31(1H, s) |
| 80 | A-80 | Et | Et | Me | 2,4-Cl$_2$ | 1.30(6H, t, J=7.3), 2.48(3H, s), 3.38(4H, br), 4.48(2H, s), 7.37(1H, dd, J=8.5, 2.4), 7.55(1H, d, J=2.4), 7.88(1H, d, J=8.5), 8.33(1H, s) |

TABLE 10

| Example No. | Compound No. | $R^{15}$ | $R^{16}$ | $R^{17}$ | $R^{18}$ | $^1$H-NMR ($\delta$) ppm |
|---|---|---|---|---|---|---|
| 81 | A-81 | Et | Et | Me | 4-NH$_2$-2-F | 1.30(6H, t, J=7.3), 2.47(3H, s), 3.37(4H, br), 4.14(2H, s), 4.43(2H, s), 6.45(1H, dd, J=17.1, 2.4), 6.48(1H, dd, J=13.4, 2.4), 7.73(1H, t, J=7.9), 8.32(1H, s) |
| 82 | A-82 | Et | Et | Me | 4-NO$_2$ | 1.31(6H, t, J=7.3), 2.48(3H, s), 3.38(4H, br), 4.51(2H, s), 8.17(2H, d, J=8.5), 8.35(2H, d, J=8.5), 8.33(1H, s) |
| 83 | A-83 | Et | Et | Me | 4-Ph | 1.31(6H, t, J=7.3), 2.49(3H, s), 3.39(4H, br), 4.49(2H, s), 7.36–7.50(3H, m), 7.63(2H, d, J=6.7), 7.71(2H, d, J=8.5), 8.05(2H, d, J=8.5), 8.34(1H, s) |
| 84 | A-84 | Et | Et | Me | 4-COPh | 1.31(6H, t, J=7.3), 2.48(3H, s), 3.39(4H, br), 4.50(2H, s), 7.48–7.67(3H, m), 7.81(2H, dd, J=7.3, 1.2), 7.90(2H, d, J=8.5), 8.10(2H, d, J=8.5), 8.34(1H, s) |
| 85 | A-85 | Et | Et | Me | 3,4-(NH$_2$)$_2$ | 1.15(6H, t, J=7.2), 2.36(3H, s), 3.28(4H, br), 4.37(2H, s), 7.29(1H, d, J=8.3), 7.62(1H, s), 7.72(1H, d, J=8.3), 8.13(1H, s) (in DMSOd6) |
| 86 | A-86 | Et | Et | Me | 4-OMPM | 1.30(6H, t, J=7.2), 2.47(3H, s), 3.37(4H, br), 3.82(3H, s), 4.45(2H, s), 5.05(2H, s), 6.93(2H, d, J=8.8), 7.04(2H, d, J=8.8), 7.36(2H, d, J=8.8), 7.91(2H, d J=8.8), 8.31(1H, s) |
| 87 | A-87 | Et | Et | Me | 4-NH$_2$-3-OMPM | 1.30(6H, t, J=7.2), 2.47(3H, s), 3.37(4H, br), 4.17(2H, br), 4.44(2H, s), 5.07(2H, s), 6.73(1H, d, J=8.1), 6.93(2H, d, J=8.8), 7.38(2H, d, J=8.8), 7.41(1H, dd J=8.1, 1.7), 7.52(1H, d, J=1.7), 8.30(1H, s) |
| 88 | A-88 | Et | Et | Me | 4-OH | 1.31(6H, t, J=7.1), 2.48(3H, s), 3.38(4H, br), 4.42(2H, s), 6.86(2H, d, J=8.5), 7.88(2H, d, J=8.8), 8.45(1H, s) |
| 89 | A-89 | Et | Et | Me | 4-NH$_2$-3-OH | 1.30(6H, t, J=7.2), 2.50(3H, s), 3.37(4H, br), 4.13(2H, br), 4.31(2H, s), 6.73(1H, d, J=8.1), 7.35(1H, d, J=1.7), 7.43(1H, dd, J=8.1, 1.7), 8.33(1H, s) |
| 90 | A-90 | Et | Et | Me | 2-NH$_2$-4-COOH | 1.12(6H, br), 2.37(3H, s), 3.26(4H, br), 4.34(2H, s), 6.87(2H, m), 7.19(1H, dd, J=8.3, 1.5), 7.54(1H, d,=1.5), 7.72(1H, d, J=8.3), 8.09(1H, s) (in DMSOd6) |
| 91 | A-91 | Et | Et | Me | 4-CO$_2$tBu | 1.30(6H, t, J=7.1), 1.61(9H, s), 2.48(3H, s), 3.38(4H, br), 4.49(2H, s), 8.02(2H, d, J=8.8), 8.08(2H, d, J=8.8), 8.33(1H, s) |

TABLE 11

| Example No. | Compound No. | $R^{15}$ | $R^{16}$ | $R^{17}$ | $R^{18}$ | $^1$H-NMR (δ) ppm |
|---|---|---|---|---|---|---|
| 92 | A-92 | Et | Et | Me | 4-CO$_2$Me | 1.30(6H, t, J=7.1), 2.48(3H, s), 3.38(4H, br), 3.95(3H, s), 4.49(2H, s), 8.05(2H, d, J=8.5), 8.14(2H, d, J=8.5), 8.32(1H, s) |
| 93 | A-93 | Et | Et | Me | 4-CONMe$_2$ | 1.30(6H, t, J=7.2), 2.47(3H, s), 2.99(3H, br), 3.13(3H, br), 3.38(4H, br), 4.48(2H, s), 7.53(2H, d, J=8.2), 8.02(2H, d, J=8.2), 8.32(1H, s) |
| 94 | A-94 | Et | Et | Me | 4-CO$_2$H | 1.12(6H, br), 2.37(3H, s), 3.26(4H, br), 4.36(2H, s), 8.09(2H, d, J=8.3), 8.11(1H, br), 8.13(2H, d, J=8.3) (in DMSOd6) |
| 95 | A-95 | Et | Et | Me | 2-NH$_2$-4-CO$_2$Me | 1.30(6H, t, J=7.2), 2.48(3H, s), 3.38(4H, br), 3.92(3H, s), 4.48(2H, s), 5.91(2H, br), 7.35(1H, dd, J=8.3, 1.5), 7.46(1H, d, J=1.5), 7.70(1H, d, J=8.3), 8.33(1H, s) |
| 96 | A-96 | Et | Et | Me | 4-NH$_2$-2-OH | 1.30(6H, t, J=7.2), 2.48(3H, s), 3.37(4H, br), 4.02(2H, br), 4.44(2H, s), 6.26(1H, dd, J=8.5, 2.3), 6.32(1H, d, J=2.3), 7.42(1H, d, J=8.5), 8.30(1H, s), 9.94(1H, s) |
| 97 | A-97 | Et | Et | Me | 4-(1-pyrrolidinyl) | 1.30(6H, t, J=7.2), 2.04(4H, m), 2.48(3H, s), 3.35(4H, br), 4.44(2H, s), 6.57(2H, d, J=8.9), 7.81(2H, d, J=8.9), 8.30(1H, s) |
| 98 | A-98 | Et | Et | Me | 4-piperidino | 1.30(6H, t, J=7.2), 1.68(6H, m), 2.49(3H, s), 3.35(4H, br), 4.44(2H, s), 6.91(2H, d, J=8.9), 7.82(2H, d, J=8.9), 8.32(1H, s) |
| 99 | A-99 | Et | Et | Me | 4-O-prenyl | 1.30(6H, t, J=7.3), 1.76(3H, s), 1.81(3H, s), 2.47(3H, s), 3.37(4H, br), 4.45(2H, s), 4.57(2H, d, J=6.7), 5.49(1H, t, J=6.7), 6.98(2H, d, J=9.2), 7.90(2H, d, J=9.2), 8.31(1H, s) |
| 100 | A-100 | Et | Et | Me | 4-O-i-Pr | 1.30(6H, t, J=7.3), 1.36(6H, d, J=6.1), 2.47(3H, s), 3.37(4H, br), 4.45(2H, s), 4.62(1H, sept, J=6.1), 6.94(2H, d, J=8.5), 7.89(2H, d, J=8.5), 8.31(1H, s) |
| 101 | A-101 | Et | Et | Me | 4-OEt | 1.29(6H, t, J=7.3), 1.44(3H, t, J=7.3), 2.47(3H, s), 3.37(4H, br), 4.09(2H, q, J=7.3), 4.45(2H, s), 6.96(2H, d, J=8.5), 7.90(2H, d, J=8.5), 8.31(1H, s) |
| 102 | A-102 | Et | Et | Me | 4-SO$_2$NH$_2$ | 1.30(6H, t, J=7.2), 2.46(3H, s), 3.38(4H, br), 4.46(2H, s), 8.04(2H, d, J=8.8), 8.10(2H, d, J=8.8), 8.23(1H, s) |

TABLE 12

| Example No. | Compound No. | $R^{15}$ | $R^{16}$ | $R^{17}$ | $R^{18}$ | $^1$H—NMR (δ) ppm |
|---|---|---|---|---|---|---|
| 103 | A-103 | Et | Et | Me | 4-O—Pr | 1.05(3H, t, J=7.3), 1.30(6H, t, J=7.3), 1.83(2H, sext, J=7.3), 2.47(3H, s), 3.37(4H, br), 3.98(2H, t, J=7.3), 4.45(2H, s), 6.96(2H, d, J=9.2), 7.90(2H, d, J=9.2), 8.31(1H, s) |
| 104 | A-104 | Et | Et | Me | 2-NO$_2$ | 1.30(6H, t, J=7.3), 2.48(3H, s), 3.38(4H, br), 4.46(2H, s), 7.66–7.79(2H, m), 7.92–8.02(2H, m), 8.30(1H, s) |
| 105 | A-105 | Et | Et | Me | 4-I | 1.30(6H, t, J=7.3), 2.48(3H, s), 3.38(4H, br), 4.47(2H, s), 7.69(2H, d, J=8.5), 7.83(2H, d, J=8.5), 8.31(1H, s) |
| 106 | A-106 | Et | Et | Me | 4-CF$_3$ | 1.31(6H, t, J=7.3), 2.52(3H, s), 3.38(4H, br), 4.49(2H, s), 7.75(2H, d, J=7.9), 8.11(2H, d, J=7.9), 8.37(1H, s) |
| 107 | A-107 | Et | Et | Me | H | 1.30(6H, t, J=73), 2.48(3H, s), 3.38(4H, br), 4.48(2H, s), 7.43–7.52(3H, m), 7.96–8.00(2H, m), 8.32(1H, s) |

TABLE 12-continued

| Example No. | Compound No. | R15 | R16 | R17 | R18 | 1H—NMR (δ) ppm |
|---|---|---|---|---|---|---|
| 108 | A-108 | Et | Et | Me | 4-Br | 1.30(6H, t, J=7.3), 2.48(3H, s), 3.38(4H, br), 4.48(2H, s), 7.62(2H, d, J=8.5), 7.85(2H, d, J=8.5), 8.32(1H, s) |
| 109 | A-109 | Et | Et | H | 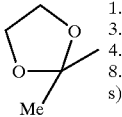 | 1.03(6H, t, J=7.3), 1.67(3H, s), 3.39(4H, br), 3.75–3.81(2H, m), 4.03–4.09(2H, m), 4.48(2H, s), 7.60(2H, d, J=8.6), 7.96(2H, d, J=8.6), 8.40(1H, s), 8.54(1H, s) |
| 110 | A-110 | Et | Et | H | 4-F | 1.31(6H, t, J=7.3), 3.39(4H, br), 4.49(2H, s), 7.18(2H, t, J=8.9), 7.97(2H, dd, J=5.3, 8.9), 8.41(1H, s), 8.55(1H, s) |
| 111 | A-111 | Et | CH2C(Br)=CH2 | H | 4-NH2 | 1.31(3H, t, J=7.3), 3.36(2H, t, J=5.9), 4.07(2H, br), 4.26(2H, br), 4.43(2H, s), 5.61(1H, s), 5.91(1H, s), 6.69(2H, d, J=8.7), 7.55(2H, d, J=8.7), 8.41(1H, s), 8.55(1H, s) |
| 112 | A-112 | Et | CH2CH2OAc | H | 4-NH2 | 1.32(3H, t, J=7.2), 2.10(3H, s), 3.32(2H, br), 3.68(2H, br), 4.01(2H, br), 4.30(2H, t, J=5.5), 4.45(2H, s), 6.71(2H, d, J=8.8), 7.77(2H, d, J=8.8), 8.40(1H, s), 8.54(1H, s) |
| 113 | A-113 | Et | CH2CH2OH | H | 4-NH2 | 1.32(3H, t, J=7.5), 3.32(2H, br), 3.62(2H, br), 3.85(2H, t, J=5.0), 4.01(2H, s), 4.45(2H, s), 6.70(2H, d, J=8.7), 7.76(2H, d, J=8.7), 8.41(1H, s), 8.55(1H, s) |
| 114 | A-114 | Et | Et | H | 4-Et | 1.26(3H, t, J=7.6), 1.30(6H, t, J=7.6), 2.71(2H, q, J=7.6), 3,38(4H, br), 4.48(2H, s), 7.30(2H, d, J=8.3), 7.89(2H, d, J=8.3), 8.40(1H, s), 8.54(1H, s) |

TABLE 13

| Example No. | Compound No. | R15 | R16 | R17 | R18 | 1H-NMR (δ) ppm |
|---|---|---|---|---|---|---|
| 115 | A-115 | Et | Et | H | 4-i-Pr | 1.27(6H, t, J=6.8), 1.30(6H, t, J=7.3), 2.96(1H, sept., J=6.8), 3.38(4H, br), 4.48(2H, s), 7.33(2H, d, J=8.3), 7.90(2H, d, J=8.3), 8.40(1H, s), 8.54(1H, s) |
| 116 | A-116 | Et | Et | H | 4-Pr | 0.95(3H, t, J=7.3), 1.30(6H, t, J=7.3), 1.67(2H, sext, J=7.3), 2.64(2H, t, J=7.3), 3.39(4H, br), 4.48(2H, s), 7.28(2H, d, J=8.1), 7.88(2H, d, J=8.1), 8.40(1H, s), 8.54(1H, s) |
| 117 | A-117 | Et | Et | H | 4-Ac | 1.32(6H, t, J=7.3), 2.66(3H, s), 3.40(4H, br), 4.52(2H, s), 8.06(2H, d, J=8.7), 8.10(2H, d, J=8.7), 8.43(1H, s), 8.55(1H, s) |
| 118 | A-118 | Et | Et | H | 4-CH2NHBoc | 1.30(6H, t, J=7.3), 1.46(9H, s), 3.38(4H, br), 4.37(2H, d, J=5.9), 4.48(2H, s), 4.90(1H, br), 7.39(2H, d, J=8.6), 8.00(2H, d, J=8.6), 8.40(1H, s), 8.57(1H, s) |
| 119 | A-119 | Et | Et | H | 4-CH2NH2 | 1.30(6H, t, J=7.3), 3.38(4H, br), 3.94(2H, s), 4.48(2H, s), 7.44(2H, d, J=8.6), 7.95(2H, d, J=8.6), 8.40(1H, s), 8.54(1H, s) |
| 120 | A-120 | Et | Et | H | 4-SMe | 1.30(6H, t, J=7.3), 2.53(3H, s), 3.38(4H, br), 4.47(2H, s), 7.30(2H, d, J=8.6), 7.87(2H, d, J=8.6), 8.40(1H, s), 8.54(1H, s) |
| 121 | A-121 | Et | i-Pr | H | 4-NO2 | 1.30(6H, d, J=6.3), 1.32(3H, t, J=7.2), 3.35(2H, br), 4.08(1H, br), 4.51(2H, s), 8.17(2H, d, J=9.0), 8.35(2H, d, J=9.0), 8.41(1H, s), 8.54(1H, s) |
| 122 | A-122 | Et | CH2CH2 | H | 4-NO2 | 1.30(3H, t, J=7.2), 3.01(2H, t, J= |

TABLE 13-continued

| Example No. | Compound No. | $R^{15}$ | $R^{16}$ | $R^{17}$ | $R^{18}$ | $^1$H-NMR ($\delta$) ppm |
|---|---|---|---|---|---|---|
| | | | NH$_2$ | | | 5.4), 3.42(4H, br), 4.52(2H, s), 8.17(2H, d, J=9.0), 8.35(2H, d, J=9.0), 8.40(1H, s), 8.53(1H, s) |
| 123 | A-123 | Et | Et | H | 4-CSNH$_2$ | 1.29(6H, t, J=7.3), 3.26(4H, br), 4.46(2H, s), 7.98(2H, d, J=8.9), 8.02(2H, d, J=8.9), 8.31(1H, s), 8.47(1H, s) (in CDCl$_3$ + CD$_3$OD) |
| 124 | A-124 | Et | Et | H | 4-NO$_2$, -2-MeO | 1.31(6H, t, J=7.3), 3.40(4H, br), 4.08(3H, s), 4.50(2H, s), 7.88–7.94(2H, m), 8.07(1H, d, J=8.3), 8.42(1H, s), 8.55(1H, s) |
| 125 | A-125 | Et | Et | H | 2,3,5,6-F$_4$, -4-NH$_2$ | 1.31(6H, t, J=7.3), 3.38(4H, br), 4.41(2H, s), 4.48(2H, s), 8.40(1H, s), 8.54(1H, s) |
| 126 | A-126 | Et | Et | H | 2-Cl,-4-NO$_2$ | 1.31(6H, t, J=7.1), 3.40(4H, br), 4.53(2H, s), 8.19–8.22(2H, m), 8.40–8.43(2H, m), 8.55(1H, s) |

TABLE 14

| Example No. | Compound No. | $R^{15}$ | $R^{16}$ | $R^{17}$ | $R^{18}$ | $^1$H-NMR ($\delta$) ppm |
|---|---|---|---|---|---|---|
| 127 | A-127 | Pr | Pr | Me | 4-NO$_2$ | 1.04(6H, t, J=7.3), 1.71(4H, sext, J=7.3), 2.48(3H, s), 3.31(4H, br), 4.50(2H, s), 8.16(2H, d, J=9.0), 8.33(1H, s), 8.35(2H, d, J=9.0) |
| 128 | A-128 | Bu | Bu | Me | 4-NO$_2$ | 0.98(6H, t, J=7.3), 1.42–1.51(4H, m), 1.61–1.72(4H, m), 2.47(3H, s), 3.35(4H, br), 4.50(2H, s), 8.17(2H, d, J=9.1), 8.33(1H, s), 8.35(2H, d, J=9.1) |
| 129 | A-129 | i-Bu | i-Bu | Me | 4-NO$_2$ | 1.03(12H, d, J=6.6), 2.00(2H, sept, J=6.6), 2.48(3H, s), 3.18(4H, br), 4.49(2H, s), 8.17(2H, d, J=9.0), 8.32(1H, s), 8.35(2H, d, J=9.0) |
| 130 | A-130 | Et | Et | i-Pr | 4-NO$_2$ | 1.28(6H, d, J=6.8), 1.32(6H, t, J=7.2), 3.00(1H, sept, J=6.8), 3.39(4H, br), 4.51(2H, s), 8.17(2H, d, J=9.0), 8.34(2H, d, J=9.0), 8.36(1H, s) |
| 131 | A-131 | Et | Et | Et | 4-NO$_2$ | 1.29(3H, t, J=7.6), 1.31(6H, t, J=7.6), 2.78(2H, q, J=7.6), 3.39(4H, br), 4.52(2H, s), 8.17(2H, d, J=9.0), 8.35(2H, d, J=9.0), 8.35(1H, s) |
| 132 | A-132 | Et | Et | Me | 2-F,-4-NO$_2$ | 1.31(6H, dt, J=2.1, 7.1), 2.48(3H, s), 3.38(4H, br), 4.51(2H, d, J=2.7), 7.93–8.27(3H, m), 8.33(1H, s) |
| 133 | A-133 | Me | Et | Me | 4-NO$_2$ | 1.31(3H, t, J=7.1), 2.49(3H, s), 2.98(3H, s), 3.40(4H, br), 4.52(2H, s), 8.16(2H, d, J=9.1), 8.34(1H, s), 8.35(2H, d, J=9.1) |
| 134 | A-134 | Et | i-Pr | Me | 4-NO$_2$ | 1.29(6H, d, J=6.4), 1.32(3H, t, J=7.1), 2.48(3H, s), 3.34(2H, br), 4.10(1H, br), 4.50(2H, s), 8.17(2H, d, J=9.1), 8.35(2H, d, J=9.1) |
| 135 | A-135 | Et | Pr | Me | 4-NO$_2$ | 1.05(3H, t, J=7.4), 1.31(3H, t, J=7.2), 1.71(2H, m), 2.48(3H, s), 3.29(2H, br), 3.40(2H, br), 4.50(2H, s), 8.17(2H, d, J=9.2), 8.33(1H, s), 8.35(2H, d, J=9.2) |
| 136 | A-136 | Et | Bu | Me | 4-NO$_2$ | 0.98(3H, t, J=7.3), 1.30(3H, t, J=7.2), 1.47(2H, m), 1.67(2H, m), 2.48(3H, s), 3.32(2H, br), 3.41(2H, br), 4.50(2H, s), 8.17(2H, d, J=9.1), 8.33(1H, s), 8.35(2H, d, J=9.1) |
| 137 | A-137 | Et | Et | H | 3-NO$_2$ | 1.32(6H, t, J=7.3), 3.40(4H, br), 4.52(2H, s), 7.71(1H, t, J=7.9), 8.34–8.38(2H, m), 8.42(1H, s), 8.55(1H, s), 8.79(1H, t, J=1.8) |

TABLE 14-continued

| Example No. | Compound No. | R$^{15}$ | R$^{16}$ | R$^{17}$ | R$^{18}$ | $^1$H-NMR (δ) ppm |
|---|---|---|---|---|---|---|
| 138 | A-138 | Pr | Pr | Et | 4-NO$_2$ | 1.03(6H, t, J=7.3), 1.29(3H, t, J=7.6), 1.70(4H, sext, J=7.3), 2.77(2H, q, J=7.6), 3.30(4H, br), 4.51(2H, s), 8.17(2H, d, J=8.9), 8.34(2H, d, J=8.9), 8.36(1H, s) |

TABLE 15

| Example No. | Compound No. | R$^{15}$ | R$^{16}$ | R$^{17}$ | R$^{18}$ | $^1$H-NMR (δ) ppm |
|---|---|---|---|---|---|---|
| 139 | A-139 | Pr | Pr | Et | 4-NH$_2$ | 0.92(6H, t, J=7.3), 1.19(3H, t, J=7.6), 1.58(4H, sext, J=7.3), 2.63(2H, q, J=7.6), 3.23(4H, br), 4.32(2H, s), 5.92(2H, br), 6.65(2H, d, J=8.6), 7.59(2H, d, J=8.6), 8.15(1H, s) (in DMSOd6) |
| 140 | A-140 | Pr | Pr | Et | 2-NH$_2$,-4-F | 1.03(6H, t, J=7.3), 1.29(3H, t, J=7.6), 1.71(4H, sext, J=7.3), 2.77(2H, q, J=7.6), 3.30(4H, br), 4.68(2H, s), 5.93(2H, br), 6.40–6.47(2H, m), 7.62(1H, dd, J=9.2, 6.2), 8.34(1H, s) |
| 141 | A-141 | Et | Et | Me | 2-OMe,-4-NH$_2$ | 1.29(6H, t, J=7.3), 2.47(3H, s), 3.37(4H, br), 3.90(3H, s), 4.03(2H, s), 4.42(2H, s), 6.26(1H, d, J=2.0), 6.31(1H, dd, J=2.0, 8.2), 7.64(1H, d, J=8.2), 8.30(1H, s) |
| 142 | A-142 | Pr | Pr | Me | 4-Cl | 1.03(6H, t, J=7.3), 1.70(4H, sext, J=7.3), 2.49(3H, s), 3.30(4H, br), 4.47(2H, s), 7.46(2H, d, J=8.7), 7.92(2H, d, J=8.7), 8.33(1H, s) |
| 143 | A-143 | Pr | Pr | Me | 4-Me | 1.03(6H, t, J=7.4), 1.70(4H, sext, J=7.4), 2.41(3H, s), 2.47(3H, s), 3.30(4H, br), 4.46(2H, s), 7.28(2H, d, J=7.9), 7.86(2H, d, J=7.9), 8.31(1H, s) |
| 144 | A-144 | Pr | Pr | Me | 4-NH$_2$ | 1.03(6H, t, J=7.3), 1.70(4H, sext, J=7.3), 2.47(3H, s), 3.30(4H, br), 4.01(2H, s), 4.43(2H, s), 6.71(2H, d, J=8.7), 7.77(2H, d, J=8.7), 8.29(1H, s) |
| 145 | A-145 | Me | Me | Me | 4-NO$_2$ | 2.49(3H, s), 2.99(3H, s), 3.00(3H, s), 4.53(2H, s), 8.16(2H, d, J=9.1), 8.34(1H, s), 8.35(2H, d, J=9.1) |
| 146 | A-146 | Me | Pr | Me | 4-NO$_2$ | 1.04(6H, t, J=7.4), 1.71(2H, sext, J=7.4), 2.48(3H, s), 2.99(3H, d, J=4.8), 3.30(2H, br), 4.51(2H, s), 8.16(2H, d, J=9.1), 8.33(1H, s), 8.35(2H, d, J=7.9) |
| 147 | A-147 | Me | Me | Me | 4-NH$_2$ | 2.48(3H, s), 2.96(3H, s), 2.98(3H, s), 4.01(2H, br), 4.45(2H, s), 6.70(2H, d, J=8.7), 7.75(2H, d, J=8.7), 8.30(1H, s) |
| 148 | A-148 | Me | Pr | Me | 4-NH$_2$ | 1.02(3H, t, J=7.3), 1.69(2H, q, J=7.3), 2.47(3H, s), 2.97(3H, d, J=4.8), 3.28(2H, br), 4.01(2H, s), 4.44(2H, s), 6.70(2H, d, J=8.7), 7.76(2H, d, J=8.7), 8.29(1H, s) |
| 149 | A-149 | Et | Pr | Et | 4-NO$_2$ | 1.04(3H, t, J=7.6), 1.23–1.32(6H, m), 1.71(2H, sext, J=7.6), 2.77(2H, q, J=7.6), 3.29(2H, br), 3.43(2H, br), 4.51(2H, s), 8.17(2H, d, J=9.2), 8.35(2H, d, J=9.2), 8.36(1H, s) |

TABLE 16

| Example No. | Compound No. | R$^{15}$ | R$^{16}$ | R$^{17}$ | R$^{18}$ | $^1$H-NMR (δ) ppm |
|---|---|---|---|---|---|---|
| 150 | A-150 | Me | Pr | Et | 4-NO$_2$ | 1.04(3H, t, J=7.3), 1.29(3H, t, J=7.6), 1.71(2H, sext, J=7.3), 2.77(2H, q, J=7.6), 3.00(3H, d, J=4.8), 3.30(2H, br), 4.53(2H, s), 8.16(2H, d, J=8.9), 8.35(2H, d, J=8.9), 8.36(1H, s) |

TABLE 16-continued

| Example No. | Compound No. | $R^{15}$ | $R^{16}$ | $R^{17}$ | $R^{18}$ | $^1$H-NMR (δ) ppm |
|---|---|---|---|---|---|---|
| 151 | A-151 | Me | Pr | Et | 4-NH$_2$ | 0.93(3H, t, J=7.3), 1.19(3H, t, J= 7.8), 1.59(2H, sext, J=7.3), 2.64(2H, q, J=7.8), 2.85(3H, d, J=4.5), 3.20(2H, br), 4.34(2H, s), 5.92(2H, br), 6.65(2H, d, J=8.6), 7.58(2H, d, J= 8.6), 8.17(1H, s) (in DMSOd6) |
| 152 | A-152 | Me | Me | Et | 4-NO$_2$ | 1.29(3H, t, J=7.6), 2.78(2H, q, J= 7.6), 2.99(3H, s), 3.01(3H, s), 4.54(2H, s), 8.16(2H, d, J=9.2), 8.35(2H, d, J= 9.2), 8.37(1H, s) |
| 153 | A-153 | Me | Me | Et | 4-NH$_2$ | 1.19(3H, t, J=7.8), 2.65(2H, q, J= 7.8), 2.83(3H, s), 2.85(3H, s), 4.35(2H, s), 5.91(2H, br), 6.65(2H, d, J=8.7), 7.58(2H, d, J=8.7), 8.16(1H, s) (in DMSOd6) |
| 154 | A-154 | Et | Et | Et | 4-NH$_2$ | 1.17(3H, t, J=7.6), 1.20(6H, t, J= 7.6), 2.65(2H, q, J=7.6), 3.29(4H, br), 4.33(2H, s), 5.92(2H, br), 6.65(2H, d, J= 8.6), 7.59(2H, d, J=8.6), 8.16(1H, s) (in DMSOd6) |
| 155 | A-155 | Pr | Pr | H | 4-NO$_2$ | 1.03(6H, t, J=7.4), 1.71(4H, sext, J= 7.4), 3.31(4H, br), 4.52(2H, s), 8.17(2H, d, J=9.1), 8.33(2H, d, J= 9.1), 8.42(1H, s), 8.54(1H, s) |
| 156 | A-156 | Pr | Pr | Me | 2-OMe,-4-NH$_2$ | 1.03(6H, t, J=7.2), 1.70(4H, sext, J= 7.2), 2.46(3H, s), 3.30(4H, br), 3.90(3H, s), 4.03(2H, s), 4.41(2H, s), 6.26(1H, d, J=2.0), 6.31(1H, dd, J= 2.0, 8.2), 7.64(1H, d, J=8.2), 8.30(1H, s) |
| 157 | A-157 | H | Pr | Me | 4-NH$_2$ | 1.03(3H, t, J=7.3), 1.69(2H, sext, J= 7.3), 2.49(3H, s), 3.21(2H, t, J=7.3), 4.02(2H, s), 4.42(2H, s), 6.40(2H, br), 6.71(2H, d, J=8.7), 7.77(2H, d, J= 8.7), 8.32(1H, s) |
| 158 | A-158 | H | Pr | Me | 4-NO$_2$ | 1.04(3H, t, J=7.3), 1.70(2H, sext, J= 7.3), 2.50(3H, s), 3.24(2H, t, J=7.3), 4.49(2H, s), 6.46(2H, br), 8.16(2H, d, J= 9.1), 8.35(2H, d, J=9.1), 8.36(1H, s) |

TABLE 17

| Example No. | Compound No. | $R^{15}$ | $R^{16}$ | $R^{17}$ | $R^{18}$ | Salt | $^1$H-NMR (δ) ppm |
|---|---|---|---|---|---|---|---|
| 159 | A-159 | Me | Me | Me | 4-NO$_2$ | HCl | 2.46(3H, s), 2.92(6H, br), 4.44(2H, s), 8.10(1H, s), 8.24(2H, d, J=9.2), 8.42(2H, d, J=9.2) (in CD$_3$OD) |
| 160 | A-160 | n-Pr | n-Pr | Me | 4-NH$_2$ | 2HCl | 0.96(6H, br), 1.65(4H, br), 2.45(3H, s), 3.25(4H, br), 3.35(2H, br), 4.39(2H, br), 7.41(2H, d, J=8.9), 8.05(2H, d, J= 8.9), 8.07(1H, s) (in CD$_3$OD) |
| 161 | A-161 | Et | Et | Me | 2-OMe-4-NO$_2$ | — | 1.31(6H, t, J=7.3), 2.48(3H, s), 3.39(4H, br), 4.07(3H, s), 4.48(2H, s), 7.88–7.94(2H, m), 8.07(1H, d, J=8.2), 8.33(1H, s) |
| 162 | A-162 | Me | Me | Me | 2-OMe-4-NO$_2$ | — | 2.50(3H, s), 3.00(6H, d, J=4.0), 4.07(3H, s), 4.51(2H, s), 7.88–7.94(2H, m), 8.07(1H, d, J=7.9), 8.35(1H, s) |
| 163 | A-163 | Me | Et | Me | 4-NO$_2$ | HCl | 1.11(3H, br), 2.39(3H, br), 2.75(3H, br), 3.30(2H, br), 4.38(2H, s), 8.13(1H, s), 8.24(2H, d, J=9.1), 8.43(2H, d, J=9.1) (in DMSOd6) |
| 164 | A-164 | Me | n-Pr | Me | 4-NO$_2$ | HCl | 0.86(3H, br), 1.52(2H, br), 2.39(3H, br), 2.80(3H, br), 3.15(2H, br), 4.38(2H, s), 8.13(1H, s), 8.24(2H, d, J=9.1), 8.43(2H, d, J=9.1) (in DMSOd6) |
| 165 | A-165 | i-Pr | i-Pr | Me | 4-NO$_2$ | — | 1.30(12H, d, J=6.4), 2.47(3H, s), 4.00(2H, br), 4.49(2H, s), |

TABLE 17-continued

| Example No. | Compound No. | R$^{15}$ | R$^{16}$ | R$^{17}$ | R$^{18}$ | Salt | $^1$H-NMR (δ) ppm |
|---|---|---|---|---|---|---|---|
| 166 | A-166 | i-Pr | i-Pr | Me | 4-NH$_2$ | — | 8.17(2H, d, J=9.1), 8.32(1H, s), 8.35(2H, d, J=9.1) 1.29(12H, d, J=6.4), 2.46(3H, s), 4.00(2H, br), 4.01(2H, s), 4.42(2H, s), 6.71(2H, d, J=8.9), 7.77(2H, d, J=8.9), 8.29(1H, s) |
| 167 | A-167 | Et | n-Pr | Me | 4-NH$_2$ | — | 1.04(3H, t, J=7.5), 1.29(3H, t, J=7.3), 1.70(2H, q, J=7.2), 2.47(3H, s), 3.28(2H, br), 3.40(2H, br), 4.01(2H, s), 4.43(2H, s), 6.71(2H, d, J=8.7), 7.77(2H, d, J=8.7), 8.29(1H, s) |
| 168 | A-168 | Me | Et | Me | 4-NH$_2$ | — | 1.29(3H, t, J=7.3), 2.48(3H, s), 2.96(3H, d, J=4.8), 3.40(2H, br), 4.00(2H, s), 4.45(2H, s), 6.71(2H, d, J=8.8), 7.77(2H, d, J=8.8), 8.30(1H, s) |

TABLE 18

| Example No. | Compound No. | R$^{15}$ | R$^{16}$ | R$^{17}$ | R$^{18}$ | Salt | $^1$H-NMR (δ) ppm |
|---|---|---|---|---|---|---|---|
| 169 | A-169 | n-Bu | n-Bu | Me | 4-NH$_2$ | — | 0.97(6H, t, J=7.2), 1.46(4H, q, J=7.1), 1.55–1.73(4H, m), 2.46(3H, s), 3.33(4H, br), 4.00(2H, s), 4.43(2H, s), 6.71(2H, d, J=8.8), 7.77(2H, d, J=8.8), 8.29(1H, s) |
| 170 | A-170 | Me | i-Pr | Me | 4-NO$_2$ | — | 1.30(6H, d, J=6.4), 2.49(3H, s), 2.96(3H, d, J=4.9), 4.10(1H, br), 4.51(2H, s), 8.17(2H, d, J=9.1), 8.33(1H, s), 8.35(2H, d, J=9.1) |
| 171 | A-171 | Me | i-Pr | Me | 4-NH$_2$ | — | 1.28(6H, d, J=6.4), 2.48(3H, s), 2.95(3H, d, J=4.9), 4.01(2H, s), 4.10(1H, br), 4.44(2H, s), 6.71(2H, d, J=8.7), 7.77(2H, d, J=8.7), 8.30(1H, s) |
| 172 | A-172 | Et | Et | H | 4-NO$_2$ | — | 1.31(6H, t, J=7.1), 3.40(4H, br), 4.52(2H, s), 8.17(2H, d, J=9.1), 8.35(2H, d, J=9.1), 8.42(1H, s), 8.55(1H, s) |
| 173 | A-173 | Me | Me | H | 4-NO$_2$ | — | 3.01(6H, d, J=4.8), 4.54(2H, s), 8.16(2H, d, J=9.1), 8.35(2H, d, J=9.1) 8.43(1H, s), 8.55(1H, s) |
| 174 | A-174 | Me | Me | H | 4-NH$_2$ | — | 2.99(6H, d, J=4.6), 4.01(2H, br), 4.48(2H, s), 6.71(2H, d, J=8.7), 7.76(2H, d, J=8.7), 8.40(1H, s), 8.53(1H, s) |
| 175 | A-175 | Et | CF$_3$CH$_2$ | Me | 4-NO$_2$ | — | 1.38(3H, t, J=7.3), 2.51(3H, s), 3.30–3.38(2H, m), 4.23(2H, q, J=7.3), 4.52(2H, s), 8.17(2H, d, J=9.1), 8.35(2H, d, J=9.1), 8.40(1H, s) |
| 176 | A-176 | Me | Et | H | 4-NH$_2$ | — | 1.29(3H, t, J=7.3), 2.97(3H, d, J=4.9), 3.42(2H, br), 4.00(2H, br), 4.46(2H, s), 6.71(2H, d, J=8.7), 7.77(2H, d, J=8.7), 8.39(1H, s), 8.54(1H, s) |
| 177 | A-177 | Me | Et | H | 4-NO$_2$ | — | 1.31(3H, t, J=7.3), 2.99(3H, d, J=4.5), 3.45(2H, br), 4.53(2H, s), 8.17(2H, d, J=8.9), 8.35(2H, d, J=8.9), 8.43(1H, s), 8.55(1H, s) |
| 178 | A-178 | Et | n-Pr | H | 4-NH$_2$ | — | 1.02(3H, t, J=7.4), 1.30(3H, t, J=7.2), 1.70(2H, q, J=7.3), 3.29(2H, br), 3.40(2H, br), 4.01(2H, s), 4.45(2H, s), 6.71(2H, d, J=8.6), 7.77(2H, d, J=8.6), 8.38(1H, s), 8.53(1H, s) |

TABLE 18-continued

| Example No. | Compound No. | R¹⁵ | R¹⁶ | R¹⁷ | R¹⁸ | Salt | ¹H-NMR (δ) ppm |
|---|---|---|---|---|---|---|---|
| 179 | A-179 | Et | n-Pr | H | 4-NO$_2$ | — | 1.03(3H, t, J=7.4), 1.31(3H, t, J=7.3), 1.71(2H, q, J=7.3), 3.30(2H, br), 3.40(2H, br), 4.52(2H, s), 8.17(2H, d, J=9.2), 8.35(2H, d, J=9.2), 8.42(1H, s), 8.55(1H, s) |

TABLE 19

| Example No. | Compound No. | R¹⁵ | R¹⁶ | R¹⁷ | R¹⁸ | Salt | ¹H-NMR (δ) ppm |
|---|---|---|---|---|---|---|---|
| 180 | A-180 | Et | n-Bu | Me | 4-NH$_2$ | — | 0.98(3H, t, J=7.3), 1.29(3H, t, J=7.3), 1.47(2H, q, J=7.4), 1.63–1.69(2H, m), 2.47(3H, s), 3.30(2H, br), 3.39(2H, br), 4.01(2H, s), 4.43(2H, s), 6.71(2H, d, J=8.7), 7.77(2H, d, J=8.7), 8.30(1H, s) |
| 181 | A-181 | Et | CH$_2$CH=CH$_2$ | Me | 4-NO$_2$ | — | 1.30(3H, t, J=7.1), 2.49(3H, s), 3.40(2H, br), 4.01(2H, br), 4.51(2H, s), 5.30(2H, dd, J=17.3, 10.2), 5.97(1H, ddt, J=17.3, 10.2, 5.4), 8.16(2H, d, J=8.5), 8.35(2H, d, J=8.5), 8.35(1H, s) |
| 182 | A-182 | Et | i-Pr | Me | 4-NH$_2$ | — | 1.28(6H, d, J=6.4), 1.31(3H, t, J=7.3), 2.47(3H, s), 3.33(2H, br), 4.01(3H, br), 4.43(2H, s), 6.71(2H, d, J=8.7), 7.77(2H, d, J=8.7), 8.29(1H, s) |
| 183 | A-183 | Et | CH$_2$C≡CH | Me | 4-NO$_2$ | — | 1.34(3H, t, J=7.3), 2.33(1H, br), 2.50(3H, s), 3.36(2H, br), 4.23(2H, br), 4.53(2H, s), 8.17(2H, d, J=9.2), 8.35(2H, d, J=9.2), 8.38(1H, s) |
| 184 | A-184 | H | Et | Me | 4-NH$_2$ | — | 1.11(3H, t, J=7.1), 2.36(3H, s), 3.30(2H, br), 4.33(2H, s), 5.93(2H, br), 6.65(2H, d, J=7.3), 7.59(2H, d, J=7.3), 8.15(1H, s) |
| 185 | A-185 | H | Et | Me | 4-NO$_2$ | — | 1.32(3H, t, J=7.3), 2.50(3H, s), 3.32(2H, br), 4.49(2H, s), 8.16(2H, d, J=9.1), 8.35(2H, d, J=9.1), 8.36(1H, s) |

TABLE 20

| Example No. | Compound No. | R¹⁵ | R¹⁶ | R¹⁷ | R¹⁸ | Salt | ¹H-NMR (δ) ppm |
|---|---|---|---|---|---|---|---|
| 186 | A-186 | Et | Et | Me | 4-NH$_2$ | 2HCl | 1.09(6H, t, J=7.1), 2.28(3H, s), 3.04(4H, br), 4.20(2H, s), 7.39(2H, d, J=8.9), 7.83(1H, s), 7.93(2H, d, J=8.9) (in CD$_3$OD) |
| 187 | A-187 | Et | Et | Me | 4-NO$_2$ | HCl | 1.24(6H, br), 2.44(3H, s), 4.42(2H, 2H, s), 8.07(1H, s), 8.24(2H, d, J=9.1), 8.42(2H, d, J=9.1) (in CD$_3$OD) |
| 188 | A-188 | Et | Pr | Me | 4-NO$_2$ | HCl | 0.97(3H, br), 1.22(6H, br), 1.65(2H, br), 2.43(3H, s), 3.30(2H, br), 3.40(2H, br), 4.41(2H, s), 8.07(1H, s), 8.22(2H, d, J=9.1), 8.41(2H, d, J=9.1) (in CD$_3$OD) |
| 189 | A-189 | Et | Et | Me | 2-MeO, 4-NH$_2$ | HCl | 1.23(6H, br), 2.46(3H, s), 4.00(3H, s), 4.41(2H, s), 6.89(1H, dd, J=1.8, 8.4), 6.95(1H, d, J=1.8), 7.87(1H, d, J=8.4), 8.07(1H, s) (in CD$_3$OD) |

TABLE 21

[Structure 1: oxadiazole-S-CH2-pyrimidine with guanidine-type substituent bearing N(Me)2 and NHR16, R18-phenyl]

or

[Structure 2: similar scaffold with NHR16 and N(Me)(Me) arrangement]

| Example No. | Compound No. | R16 | R17 | R18 | 1H-NMR (δ) ppm |
|---|---|---|---|---|---|
| 190 | A-190 | Et | H | 4-NO2 | 1.24(3H, t, J=7.2), 3.05(6H, s), 3.28(2H, dq, J=7.2, 5.1), 4.50(2H, s), 8.03(1H, br), 8.17(2H, d, J=9.0), 8.36(2H, d, J=9.0), 8.39(1H, s), 8.53 (1H, s) |

Example 191 Synthesis of Compound B-1

To a solution of 2-(2-aminophenyl)-5-mercaptooxadiazole (2.0 g) in 50 ml of methanol were added 600 mg of potassium hydroxide and 1.48 g of methyl iodide and the mixture was stirred for 1 h at room temperature. Methanol was removed and dichloromethane was added. The organic layer was washed with water and purified by column chromatography on silica gel to give 1.87 g of 2-(2-aminophenyl)-(5-methylthio)oxadiazole.

$^1$H-NMR: (CDCl$_3$) 2.78(3H, s), 5.76(2H, br), 6.74(1H, dt, J=1.0, 7.8 Hz), 6.78(1H, dd, J=7.8, 1.0 Hz), 7.26(1H, dt, J=1.5, 7.8 Hz), 7.69(1H, dd, J=1.5, 7.8 Hz).

To a solution of 2-(2-aminophenyl)-5-(methylthio) oxadiazole (1.8 g) in methoxyethanol was added 4.4 g of hydrazine hydrate and the mixture was stirred for 30 h at 120° C. The solvent and excess hydrazine were removed and the residue was purified by column chromatography on silica gel to give 613 mg of 2-(2-aminophenyl)-5-hydrazinooxadiazole.

$^1$H-NMR (CDCl$_3$): 4.04(2H, br), 5.44(2H, br), 6.66(1H, dt, J=1.4, 7.8 Hz), 6.69(1H, dd, J=7.8, 1.4 Hz), 7.23(1H, dt, J=1.4, 7.8 Hz), 7.23(1H, br), 7.29(1H, dd, J=7.8, 1.4 Hz).

Compound 5 (100 mg) was dissolved in 25% solution of hydrogen bromide in acetic acid (3 ml) and the mixture was stirred overnight at 40° C. The solvent was removed under reduced pressure and the residue was dissolved in 3 ml of methanol. To the solution was added 180 mg of 2-(2-aminophenyl)-5-hydrazino-oxadiazole and the mixture was stirred for 4 h. After a half amount of methanol was removed, the residual mixture was purified by the use of silica gel column chromatography gave 55 mg of compound II-1. The physical data was shown in Table 22.

Example 192 Synthesis of Compound B-2

To a solution of 2-aminobenzoic hydrazide (1.0 g) in 30 ml of THF was added 1.3 g of carbonyldimidazole and the mixture was heated at reflux for 15 h. The solvent was removed under reduced pressure and the residue was crystallized from aqueous ethanol to give 809 mg of 2-(2-aminophenyl)-5-oxadiazolinone.

$^1$H-NMR(DMSOd$_6$): 6.30(2H, br), 6.64(1H, ddd, J=7.9, 7.0, 0.9 Hz), 6.84(1H, dd, J=8.6, 0.9 Hz), 7.22(1H, ddd, J=8.6, 7.0, 1.5 Hz), 7.44(1H, dd, J=7.9, 1.5 Hz), 12.50(1H, br).

Compound 5 (200 mg) was dissolved in 25% solution of hydrogen bromide in acetic acid (1 ml) and the mixture was stirred overnight at 40° C. The solvent was removed under reduced pressure and the residue was dissolved in 1 ml of DMF. The mixture was added to a solution of 320 mg of 2-(2-aminophenyl)-5-oxadiazolinone and 75 mg of sodium hydride in 5 ml of DMF at ice-cooling. The reaction mixture was stirred for 1 h at room temperature and water was added to the mixture. The mixture was extracted with dichloromethane and the organic layer was washed with brine and dried. Purification by the use of silica gel column chromatography gave 40 mg of desired compound. The physical data was shown in Table 22.

Example 193 Synthesis of Compound B-3

To a solution of 1-(2-aminobenzoyl)thiosemicarbazide (1.3 g) in 30 ml of methanol was added 1.52 g of red mercuric oxide and the mixture was heated at reflux for 5 h. The insoluble material was removed by filtration and filtrate was concentrated in vacuo. The residue was purified by column chromatography on silica gel to give 645 mg of 2-amino-5-(2-aminophenyl)oxadiazole.

$^1$H-NMR(DMSOd$_6$): 6.53(2H, br), 6.62(1H, t, J=7.8 Hz), 6.83(1H, d, J=7.8 Hz), 7.16(1H, dt, J=1.6, 7.8 Hz), 7.16(2H, br), 7.43(1H, dd, J=7.8, 1.6 Hz).

Using 2-amino-5-(2-aminophenyl)oxadiazole as a starting material, compound B3 (33 mg) was obtained in a manner similar to that described in Example 192. The physical data was shown in Table 22.

Example 194 Synthesis of Compound B-4

To a solution of 2-aminobenzoic hydrazide (1.5 g) in DMF was added 0.7 g of methyl isothiocyanate and the mixture was stand for a day. The solvent was removed and chloroform was added to the residue to give 2.1 of 1-(2-aminobenzoyl) 4-methylthiosemicarbazide as a precipitate.

$^1$H-NMR(DMSOd$_6$): 2.87(3H, d, J=4.3 Hz), 6.51(1H, t, J=7.8 Hz), 6.71(1H, d, J=7.8 Hz), 7.18(1H, t, J=7.8 Hz), 7.64(1H, d, J=7.8 Hz), 7.95(1H, br).

Condensation with pyrimidine derivative which was carried out in a manner similar to that described in Example 191 gave compound B-4. The physical data was shown in Table 22.

TABLE 22

| Example No. | Compound No. | X | $^1$H-NMR (δ) ppm |
|---|---|---|---|
| 191 | B-1 | —NHNH— | 1.14(3H, t, J=7.2), 2.37(3H, s), 2.82 (3H, d, J=4.6), 3.26(2H, dq, J=5.6, 7.2), 4.21(2H, s), 6.56(1H, ddd, J=7.8, 7.1, 1.0), 6.68(1H, dd, J=8.7, 1.0), 7.22(1H, ddd, J=8.7, 7.1, 1.4), 7.47(1H, dd, J=7.8, 1.4), 7.76(1H, s) (in DMSOd6) |
| 192 | B-2 | —O— | 1.27(3H, t, J=7.1), 2.49(3H, s), 2.96 (3H, d, J=4.9), 3.39(2H, br), 4.95(2H, s), 5.22(2H, br), 6.69(1H, dd, J=8.3, 0.7), 6.72(1H, ddd, J=8.1, 7.0, 0.7), 7.21(1H, ddd, J=8.3, 7.0, 1.5), 7.61 (1H, dd, J=8.1, 1.5), 8.16(1H, s) |
| 193 | B-3 | —NH— | 1.34(3H, t, J=7.1), 2.50(3H, s) 2.99(3H, d, J=4.2), 3.40(2H, br), 4.46(2H, d, J=2.9), 5.72 (2H, br), 6.70(1H, ddd, J=7.8, 7.3, 1.0), 6.74(1H, dd, J=8.3, 1.0), 6.75(1H, br), 7.18(1H, ddd, J=8.3, 7.3, 1.5), 7.55 (1H, dd, J=7.8, 1.5), 8.21(1H, s) |
| 194 | B-4 | —NMe— | 1.20(3H, t, J=6.8), 2.50(3H, s), 2.89 (3H, d, J=4.6), 3.11(3H, s), 3.29(2H, br), 4.68(2H, s), 5.74(2H, br), 6.70(1H, ddd, J=7.8, 7.3, 0.7), 6.75(1H, dd, J=8.3, 0.7), 7.17(1H, ddd, J=8.3, 7.8, 1.5), 7.58(1H, dd, J=7.8, 1.5), 8.14 (1H, s) |

Example 195–Example 196

Compound (C-1) and compound (C-2) were synthesized in a manner similar to those described in Example 1 to Example 190. The physical data were shown in Table 23.

TABLE 23

| Example No. | Compound No. | $R^{19}$ | $^1$H-NMR (δ) ppm |
|---|---|---|---|
| 195 | C-1 | Me | 1.27(6H, t, J=7.1), 2.57(3H, s), 3.36(4H, br), 4.70(2H, s), 5.78(2H, br), 6.73(1H, ddd, J=8.1, 6.8, 1.1), 6.78(1H, dd, J=8.3, 1.1), 7.25(1H, ddd, J=8.3, 6.8, 1.5), 7.65(1H, dd, J=8.1, 1.5), 8.45(1H, s) |
| 196 | C-2 | Et | 1.27(6H, t, J=7.1), 1.28(3H, t, J=7.6), 2.87(2H, q, J=7.6), 3.36(4H, br), 4.72(2H, s), 5.78(2H, br), 6.73(1H, t, J=7.7), 6.78(1H, d, J=7.7), 7.26(1H, td, J=7.7, 1.5), 7.66(1H, dd, J=7.7, 1.5), 8.51(1H, s) |

Example 197 Synthesis of Compound D-1

A mixture of 2-aminonicotinic acid methylester (0.97 g) and 1.81 g of hydrazine hydrate was heated for 2 h at 100° C. Excess hydrazine was removed under reduced pressure and the residue was suspended in 20 ml of ethanol. To the suspension were added 1.65 g of carbon disulfide and 2.19 g of triethylamine and the mixture was heated for 15 h. Ethanol was removed and water was added to the reside. After removal of the insoluble material, the mixture was neutralized by adding aqueous potassium hydrogen sulfate and the precipitate was collected to give 0.51 g of 2-(2-aminopyridine-3-yl)-5-mercaptooxadiazole.

$^1$H-NMR (CDCl$_3$+CD$_3$OD): 6.77(1H, dd, J=7.8, 4.9 Hz), 8.06(1H, dd, J=7.8, 1.2), 8.19(1H, dd, J=4.9, 1.2 Hz).

Compound 10 (200 mg) was dissolved in 25% solution of hydrogen bromide in acetic acid (1 ml) and the mixture was stirred overnight at 40° C. The solvent was removed under reduced pressure and the residue was dissolved in 2 ml of DMF. The mixture was added to a solution of 332 mg of 2-(2-aminopyridine-3-yl)-5-mercapto-1,3,4-oxadiazole and 68 mg of sodium hydride in 2 ml of DMF at ice-cooling. After stirring for 1 h at room temperature, water was added to the mixture. The resulting mixture was extracted with dichloromethane and the organic layer was washed with brine and dried. Purification by use of silica gel column chromatography gave 182 mg of compound D-1. The physical data was shown in Table 24.

Example 198–Example 241

Compound D-2 to compound D-45 were synthesized in a manner similar to those described in Example 1 to Example 190 and Example 197. The physical data were shown in Tables 24 to 27.

TABLE 24

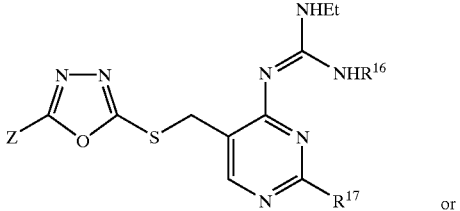

| Example No. | Compound No. | R[16] | R[17] | Z | $^1$H-NMR (δ) ppm |
|---|---|---|---|---|---|
| 197 | D-1 | Et | Me | 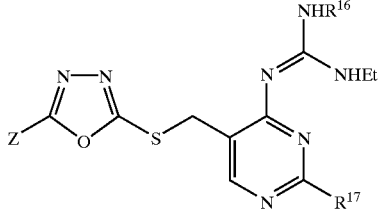 | 1.30(6H, t, J=7.2), 2.48(3H, s), 3.38(4H, br), 4.47(2H, s), 6.48(1H, br), 6.70(1H, dd, J=7.8, 4.8), 7.90(1H, dd, J=7.8, 2.0), 8.19(1H, dd, J=7.8, 2.0), 8.32(1H, s) |
| 198 | D-2 | Me | Me | 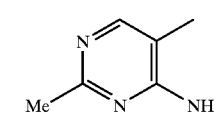 | 1.30(3H, t, J=7.2), 2.49(3H, s), 2.98(3H, d, J=4.6), 3.41(2H, br), 4.51(2H, s), 7.43(1H, dd, J=8.1, 4.9), 8.27(1H, dt, 8.1, 2.0), 8.33(1H, s), 8.74(1H, dd, J=4.9, 2.0), 9.19(1H, d, J=2.0) |
| 199 | D-3 | Et | Me | 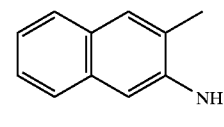 | 1.17(6H, t, J=7.2), 2.35(3H, s), 2.43(3H, s), 3.30(4H, dq, J=5.4, 7.2), 4.40(2H, s), 7.56(2H, br), 8.16(1H, s), 8.59(1H, s) (in DMSOd6) |
| 200 | D-4 | Et | Me | 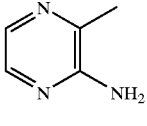 | 1.30(6H, t, J=7.3), 2.49(3H, s), 3.38(4H, br), 4.51(2H, s), 5.73(2H, br), 7.08(1H, s), 7.20(1H, m), 7.40(1H), 7.56(1H, d, J=7.9), 7.72(1H, d, J=7.9), 8.23(1H, s), 8.36(1H, s) |
| 201 | D-5 | Et | Me | 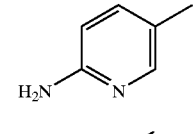 | 1.30(6H, t, J=7.3), 2.48(3H, s), 3.37(4H, br), 4.50(2H, s), 6.58(2H, br), 8.03(1H, d, J=2.5), 8.16(1H, d, J=2.5), 8.35(1H, s) |
| 202 | D-6 | Et | Me | 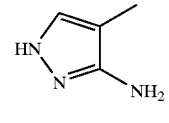 | 1.30(6H, t, J=7.2), 2.47(3H, s), 3.37(4H, br), 4.45(2H, s), 4.80(2H, br), 6.55(1H, dd, J=8.5, 0.7), 8.00(1H, dd, J=8.5, 2.3), 8.30(1H, s), 8.65(1H, dd, J=2.3, 0.7) |
| 203 | D-7 | Et | Me | 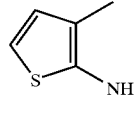 | 1.30(6H, t, J=7.2), 2.48(3H, s), 3.37(4H, br), 4.42(2H, s), 4.93(2H, br), 7.72(1H, s), 8.29(1H, s) |
| 204 | D-8 | Et | Me | 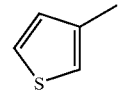 | 1.30(6H, t, J=7.1), 2.47(3H, s), 3.37(4H, br), 4.41(2H, s), 5.39(2H, br), 6.62(1H, d, J=5.2), 7.27(1H, d, J=5.2), 8.30(1H, s) |
| 205 | D-9 | Et | H | 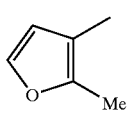 | 1.30(6H, t, J=7.3), 3.38(4H, br), 4.47(2H, s), 7.43(1H, dd, J=4.9, 3.0), 7.61(1H, dd, J=4.9, 1.3), 7.94(1H, dd, J=3.0, 1.3), 8.40(1H, s), 8.54(1H, s) |
| 206 | D-10 | Et | H | 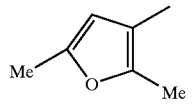 | 1.30(6H, t, J=7.3), 2.62(3H, s), 3.39(4H, br), 4.46(2H, s), 6.71(1H, d, J=2.0), 7.33(1H, d, J=2.0), 8.39(1H, s), 8.54(1H, s) |
| 207 | D-11 | Et | H |  | 1.30(6H, t, J=7.3), 2.28(3H, s), 2.56(3H, s), 3.38(4H, br), 4.44(2H, s), 6.28(1H, s), 8.38(1H, s), 8.54(1H, s) |

TABLE 24-continued
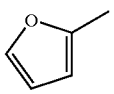
| Example No. | Compound No. | R¹⁶ | R¹⁷ | Z | ¹H-NMR (δ) ppm |
|---|---|---|---|---|---|
| 208 | D-12 | Et | H | 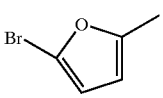 | 1.30(6H, t, J=7.3), 3.38(4H, br), 4.48(2H, s), 6.57(1H, dd, J=3.6, 2.0), 7.08(1H, dd, J=3.6, 1.0), 7.61(1H, dd, J=2.0, 1.0), 8.39(1H, s), 8.54(1H, s) |
| 209 | D-13 | Et | H | 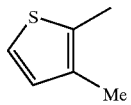 | 1.30(6H, t, J=7.3), 3.39(4H, br), 4.48(2H, s), 6.50(1H, d, J=3.5), 7.03(1H, d, J=3.5), 8.38(1H, s), 8.54(1H, s) |
| 210 | D-14 | Et | H | 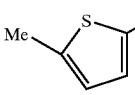 | 1.30(6H, t, J=7.3), 2.58(3H, s), 3.39(4H, br), 4.46(2H, s), 6.96(1H, d, J=4.9), 7.38(1H, d, J=4.9), 8.41(1H, s), 8.54(1H, s) |
TABLE 25
| Example No. | Compound No. | R¹⁶ | R¹⁷ | Z | ¹H-NMR (δ) ppm |
|---|---|---|---|---|---|
| 211 | D-15 | Et | H | 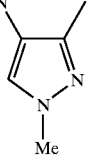 | 1.30(6H, t, J=7.3), 2.54(3H, s), 3.38(4H, br), 4.45(2H, s), 6.79(1H, d, J=4.0), 7.46(1H, d, J=4.0), 8.38(1H, s), 8.54(1H, s) |
| 212 | D-16 | Et | H | 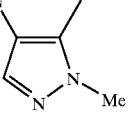 | 1.30(6H, t, J=7.3), 3.39(4H, br), 4.06(3H, s), 4.51(2H, s), 8.28(1H, s), 8.40(1H, s), 8.54(1H, s) |
| 213 | D-17 | Et | H | 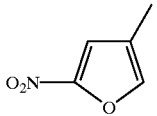 | 1.31(6H, t, J=7.3), 3.40(4H, br), 4.13(3H, s), 4.51(2H, s), 8.20(1H, s), 8.41(1H, s), 8.55(1H, s) |
| 214 | D-18 | Et | H | 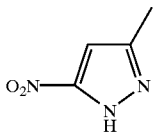 | 1.31(6H, s), 3.39(4H, br), 4.52(2H, s), 7.27(1H, d, J=4.0), 7.43(1H, d, J=4.0), 8.40(1H, s), 8.55(1H, s) |
| 215 | D-19 | Et | H |  | 1.16(6H, t, J=7.3), 3.31(4H, br), 4.40(2H, s), 7.38(1H, s), 8.26(1H, s), 8.44(1H, s) (in DMSOd6) |

TABLE 25-continued

| Example No. | Compound No. | R¹⁶ | R¹⁷ | Z | ¹H-NMR (δ) ppm |
|---|---|---|---|---|---|
| 216 | D-20 | Et | H | 3-methyl-4-nitro-1H-pyrazol-5-yl | 1.16(6H, t, J=7.3), 3.30(4H, br), 4.42(2H, s), 8.25(1H, s), 8.43(1H, s), 9.04(1H, s) (in DMSOd6) |
| 217 | D-21 | Et | H | 4-methylthiophen-2-yl | 1.30(6H, t, J=7.3), 3.38(4H, br), 4.47(2H, s), 7.43(1H, dd, J=4.9, 3.0), 7.60(1H, dd, J=4.9, 1.3), 7.94(1H, dd, J=3.0, 1.3), 8.40(1H, s), 8.54(1H, s) |
| 218 | D-22 | Et | H | 3-methyl-4-nitro-1H-pyrazol-5-yl | 1.16(6H, t, J=7.3), 3.30(4H, br), 4.42(2H, s), 8.25(1H, s), 8.43(1H, s), 9.04(1H, s) (in DMSOd6) |
| 219 | D-23 | Et | H | 3-methyl-5-nitro-1H-pyrazol-4-yl | 1.16(6H, t, J=7.3), 3.31(4H, br), 4.40(2H, s), 7.38(1H, s), 8.26(1H, s), 8.44(1H, s) (in DMSOd6) |
| 220 | D-24 | Et | H | 5-nitrofuran-2-yl (methyl) | 1.31(6H, t, J=7.3), 3.39(4H, br), 4.52(2H, s), 7.27(1H, d, J=4.0), 7.43(1H, d, J=4.0), 8.40(1H, s), 8.55(1H, s) |
| 221 | D-25 | Et | H | 3-methoxy-5-methylisoxazol-4-yl | 1.16(6H, t, J=7.3), 3.31(4H, quint, J=7.3), 4.00(3H, s), 4.43(2H, s), 7.13(1H, s), 8.26(1H, s), 8.43(1H, s) (in DMSOd6) |
| 223 | D-26 | Et | H | 4,5-dimethyl-1H-imidazol-2-yl | 1.16(6H, t, J=6.9), 2.48(3H, s), 3.32(4H, quint, J=6.9), 4.36(2H, s), 7.69(1H, s), 8.22(1H, s), 8.42(1H, s) (in DMSOd6) |
| 223 | D-27 | Et | H | 2,3,4-trimethyl-1H-pyrrol-5-yl | 1.16(6H, t, J=7.1), 2.20(3H, s), 2.22(3H, s), 3.31(4H, quint, J=7.1), 4.36(2H, s), 5.80(1H, d, J=2.0), 8.20(1H, s), 8.42(1H, s), 11.32(1H, br) (in DMSOd6) |

TABLE 26

| Example No. | Compound No. | R¹⁶ | R¹⁷ | Z | ¹H-NMR (δ) ppm |
|---|---|---|---|---|---|
| 224 | D-28 | Et | H | quinoxalin-6-yl | 1.32(6H, t, J=7.1), 3.41(4H, br), 4.54(2H, s), 8.22(1H, d, J=8.9), 8.40–8.45(1H, m), 8.55(1H, s), 8.67(1H, d, J=1.8), 8.92(2H, dd, J=1.8, 4.3) |
| 225 | D-29 | Et | H | 6-methylpyridin-3-yl | 1.30(6H, t, J=7.3), 2.64(3H, s), 3.39(4H, br), 4.50(2H, s), 7.28(1H, d, J=8.1), 8.16(1H, dd, J=8.1, 2.3), 8.41(1H, s), 8.54(1H, s), 9.06(1H, d, J=2.3) |

TABLE 26-continued

| Example No. | Compound No. | R¹⁶ | R¹⁷ | Z | ¹H-NMR (δ) ppm |
|---|---|---|---|---|---|
| 226 | D-30 | Et | H | | 1.30(6H, t, J=7.3), 3.38(4H, br), 4.46(2H, s), 6.87(1H, dd, J=1.5, 0.8), 7.51(1H, t, J=0.8), 8.01(1H, dd, J=1.5, 0.8), 8.38(1H, s), 8.54(1H, s) |
| 227 | D-31 | Et | H | | 1.15(6H, t, J=7.1), 3.31(4H, br), 4.40(2H, s), 6.72(1H, s), 8.26(1H, s), 8.43(1H, s) (in DMSOd6) |
| 228 | D-32 | Et | H | | 1.30(6H, t, J=7.3), 2.67(3H, s), 3.39(4H, br), 4.53(2H, s), 8.43(1H, s), 8.54(1H, s), 8.57(1H, d, J=1.0), 9.28(1H, d, J=1.0) |
| 229 | D-33 | Et | H | | 1.17(6H, t, J=7.3), 3.30(4H, br), 4.44(2H, s), 7.61(1H, dd, J=7.9, 4.8), 8.32(1H, s), 8.42(1H, d, J=7.9), 8.45(1H, s), 8.70(1H, s), 8.74(1H, d, J=4.8), 9.23(1H, d, J=2.1) (in DMSOd6) |
| 230 | D-34 | Et | H | | 1.31(6H, t, J=7.3), 3.40(4H, br), 4.52(2H, s), 7.90(2H, d, J=6.3), 8.17(1H, s), 8.43(1H, s), 8.55(1H, s), 8.77(2H, d, J=6.3) |
| 231 | D-35 | Et | H | | 1.30(6H, t, J=7.3), 3.39(4H, br), 4.50(2H, s), 6.40(2H, t, J=2.3), 7.40(1H, d, J=8.6), 7.57(2H, t, J=2.3), 8.31(1H, dd, J=8.6, 2.3), 8.42(1H, s), 8.55(1H, s), 8.97(1H, dd, J=2.3, 1.0). |
| 232 | D-36 | Et | Me | | 1.31(6H, t, J=7.3), 2.29(3H, s), 2.48(3H, s), 3.38(4H, br), 4.44(2H, s), 7.45(1H, d, J=5.3), 8.19(1H, d, J=5.3), 8.33(1H, s), 10.02(1H, br) |
| 233 | D-37 | Et | H | | 1.31(6H, t, J=7.3), 3.39(4H, br), 4.50(2H, s), 5.76(2H, br), 7.44(1H, d, J=5.3), 8.00(1H, d, J=5.3), 8.28(1H, s), 8.42(1H, s), 8.55(1H, s) |
| 234 | D-38 | Et | H | | 1.31(6H, t, J=7.3), 3.39(4H, br), 4.46(2H, s), 6.69(1H, dd, J=8.9, 1.7), 7.99–8.04(2H, m), 8.38(1H, s), 8.54(1H, s), 11.73(1H, br) |
| 235 | D-39 | Et | H | | 1.31(6H, t, J=7.3), 3.39(4H, br), 4.00(3H, s), 4.49(2H, s), 6.84(1H, d, J=8.9), 8.14(1H, dd, J=8.9, 2.3), 8.40(1H, s), 8.55(1H, s), 8.74(1H, d, J=2.3) |

TABLE 26-continued

| Example No. | Compound No. | R16 | R17 | Z | 1H-NMR (δ) ppm |
|---|---|---|---|---|---|
| 236 | D-40 | Et | H | (5-methyl-1-methyl-2-oxo-1,2-dihydropyridin-3-yl) | 1.31(6H, t, J=7.3), 3.39(4H, br), 3.62(3H, s), 4.46(2H, s), 6.66(1H, d, J=9.6), 7.86(1H, dd, J=9.6, 2.3), 8.04(1H, d, J=2.3), 8.38(1H, s), 8.54(1H, s) |

TABLE 27

| Example No. | Compound No. | R16 | R17 | Z | 1H-NMR (δ) ppm |
|---|---|---|---|---|---|
| 237 | D-41 | Et | H | (pyridin-4-yl)methyl | 1.31(6H, t, J=7.1), 3.39(4H, br), 4.51(2H, s), 7.83(2H, d, J=6.1), 8.42(1H, s), 8.55(1H, s), 8.78(2H, d, J=6.1) |
| 238 | D-42 | Et | H | (pyridine N-oxide-4-yl)methyl | 1.31(6H, t, J=7.1), 3.39(4H, br), 4.50(2H, s), 7.83(2H, d, J=7.4), 8.25(2H, d, J=7.4), 8.40(1H, s), 8.55(1H, s) |
| 239 | D-43 | Et | H | (4-methyl-2-nitrothiophen-5-yl) | 1.31(6H, t, J=7.3), 3.39(4H, br), 4.49(2H, s), 8.08(1H, d, J=1.8), 8.35(1H, d, J=1.8), 8.40(1H, s), 8.55(1H, s) |
| 240 | D-44 | Et | H | (E)-2-(4-aminophenyl)vinyl | 1.30(6H, t, J=7.3), 3.38(4H, br), 3.91(2H, br), 4.46(2H, s), 6.67(2H, d, J=8.6), 6.76(1H, d, J=16.3), 7.32(1H, d, J=16.3), 7.34(2H, d, J=8.6), 8.39(1H, s), 8.54(1H, s) |
| 241 | D-45 | Et | Me | (6-methyl-3-nitropyridin-5-yl) | 1.31(6H, t, J=7.3), 2.48(3H, s), 3.39(4H, br), 4.53(2H, s), 8.36(1H, s), 8.40(1H, dd, J=8.6, 0.7), 8.64(1H, dd, J=8.6, 2.6), 9.53(1H, dd, J=2.6, 0.7) |

Example 242 Synthesis of Compound E-1

To a solution of 1-amino-(4-chlorobenzaldehyde)oxime (50 mg) in 4 ml of dichloromethane was added 40 mg of thiophosgene at 0° C. The mixture was stirred for 2 h at room temperature and water was added to the mixture. The resulting mixture was extracted with dichloromethane. The organic layer was extracted with aqueous potassium carbonate. The aqueous layer was neutralized by adding dilute hydrochloric acid and extracted with dichloromethane. The organic layer was dried and purified by the use of silica gel column chromatography to give 12 mg of 3-(4-chlorophenyl)-5-mercapto-1,2,4-oxadiazole.

1H-NMR(CDCl3): 6.96(2H, d, J=8.8 Hz), 7.32(2H, d, J=8.8 Hz).

Compound 10 (58 mg) was dissolved in 25% solution of hydrogen bromide in acetic acid (1 ml) and the mixture was stirred overnight at 40° C. The solvent was removed under reduced pressure and the residue was dissolved in 2 ml of DMF. The mixture was added to a solution of 35 mg of 3-(4-chlorophenyl)-5-mercapto-1,2,4-oxadiazole and 55 mg of potassium t-butoxide in 1 ml of DMF at ice-cooling. After stirring for 3 h at room temperature, water was added to the mixture. The resulting mixture was extracted with dichloromethane. The organic layer was washed with brine, dried, and purified by the use of preparative thin layer chromatography to give 12 mg of compound E-1. The physical data was shown in Table 28.

Example 243 Synthesis of Compound E-2

Compound E-2 was synthesized in a manner similar to that described in Example 242. The physical data was shown in Table 28.

Example 244 Synthesis of Compound E-3

To a solution of 2-amino-4'-chloroacetophenone hydrochloride (1.48 g) in 30 ml of dichloromethane were added 1.65 g of thiophosgene and 3.63 g of triethylamine at 0° C. and the mixture was stirred over night at room temperature. To the reaction mixture were added IN sodium hydroxide solution and methanol. The resulting mixture was stirred at room temperature and partitioned between ethyl acetate and water. The aqueous layer was neutralized by adding dil. hydrochloric acid and the resulting crystal was collected and dried to give 220 mg of 5-(4-chlorophenyl)-2-mercaptooxazole.

¹H-NMR(CDCl₃): 7.10(1H, s), 7.39(2H, d, J=8.6 Hz), 7.52(2H, d, J=8.6 Hz).

Condensation with pyrimidine derivative which was carried out in a manner similar to that described in Example 242 gave 284 mg of compound E-3. The physical data was shown in Table 28.

Example 245 Synthesis of Compound E-4

To a solution of 4-chlorobenzoic hydrazide (500 mg) in 10 ml of ethanol were added 444 mg of carbon disulfide and 163 mg of potassium hydroxide and the mixture was stirred for 2 h at room temperature. Ethanol was removed under reduced pressure and the obtained powder was gradually added to 3 ml of conc. sulfuric acid at ice-cooling. After stirring for 10 min, the mixture was poured into ice-water and extracted with ethyl acetate. The organic layer was extracted with aqueous potassium carbonate and the aqueous layer was neutralized by adding conc. hydrochloric acid. The precipitate was collected and dried to give 235 mg of 5-(4-chlorophenyl)-2-mercaptothiadiazole.

¹H-NMR(CDCl₃): 7.46(2H, d, J=8.5 Hz), 7.62(2f, d, J=8.5 Hz), 10.26(1H, br).

Condensation with pyrimidine derivative which was carried out in a manner similar to that described in Example 242 gave 301 mg of compound E-4. The physical data was shown in Table 28.

Example 246 Synthesis of Compound E-5

Isatoic anhydride (4.9 g) and thiosemicarbazide (2.8 g) were dissolved in 30 ml of DMF and the resulting mixture was stirred 20 h at 60 to 80° C. The solvent was removed under reduced pressure and the residue was recrystallized from methanol and ethanol to give 2.94 g of 1-(2-aminobenzoyl)thiosemicarbazide.

¹H-NMR(DMSOd6) 6.49(1H, t, J=7.8 Hz), 6.70(1H, dd, J=7.8, 1.3 Hz), 7.16(1H, dt, J=1.6, 7.8 Hz), 7.51(1H, br), 7.62(1H, d, J=7.8 Hz), 7.78(1H, br), 9.96(1H, br).

To a solution of 1-(2-aminobenzoyl)thiosemicarbazide (500 mg) and 2-ethoxyethanol was added 300 mg of potassium t-butoxide and the resulting mixture was heated at reflux for 2.5 h. The solvent was removed under reduced pressure and the residue was neutralized by adding aqueous potassium hydrogen sulfate. The resulting participate was collected to give 281 mg of 2-(2-aminophenyl)-5-mercaptotriazole.

¹H-NMR(DMSOd₆): 6.53(2H, br), 6.62(1H, t, J=7.8 Hz), 6.83(1H, d, J=7.8 Hz), 7.16(1H, dt, J=1.6, 7.8 Hz), 7.16(2H, br), 7.43(1H, dd, J=7.8, 1.6 Hz), 7.78(1H, br), 9.96(1H, br).

Condensation with pyrimidine derivative which was carried out in a manner similar to that described in Example 242 gave compound E-5. The physical data was shown in Table 28.

Example 247 Synthesis of Compound E-6

To a solution of ethyl 4-chlorobenzoylacetate (500 mg) in 4 ml of ethanol was added 202 mg of methylhydrazine and the resulting mixture was stirred over night at room temperature. The solvent was removed under reduced pressure and to the residue was purified by the use of silica gel column chromatography to give 199 mg of 3-(4-chlorophenyl)-1-methylpyrazoline-5-one.

¹H-NMR(CDCl₃): 3.41(3H, s), 3.58(2H, s), 7.39(2H, d, J=8.8 Hz), 7.60(2H, d, J=8.8Hz).

To a solution of the compound synthesized in the above step in dioxane was added 231 mg of Lawesson's Reagent and the resulting mixture was heated at reflux for 4 h. The reaction mixture was concentrated and the residue was purified by the use of silica gel column chromatography to give 91 mg of 3-(4-chlorophenyl)-1-methyl-5-mercaptopyrazole. 3-(4-chlorophenyl)-1-methyl-5-mercaptopyrazole (91 mg) and pyrimidine derivative are condensed in a manner similar to that described in Example 242 to give 103 mg of compound E-6. The physical data was shown in Table 28.

Example 248 Synthesis of Compound E 7

4-tolylboronic acid (500 mg), 2-bromofuran, and tetrakis (triphenylphosphine)palladium (177 mg) were added to the mixture of 24 ml of dimethoxyethane and 15 ml of ethanol under nitrogen atmosphere. Additionally 1N sodium carbonate (12 ml) was added to the mixture and the resulting mixture was heated at reflux for 2 h. Water was added to the mixture and the mitture was extracted with diethyl ether. The organic layer was dried and the solvent was removed under reduced pressure. The residue was purified by the use of silica gel column chromatography to give 438 mg of 2-(4-tolyl)furan.

¹H-NMR(CDCl₃): 2.36(3H, s), 6.45(1H, dd, J=3.4, 1.5 Hz), 6.59(11, d, J=3.4 Hz), 7.19(2H, d, J=8.0 Hz), 7.44(1H, d, J=1.5 Hz), 7.57(2, d, J=8.0 Hz).

To a solution of the compound obtained in the above step in 5 ml of THF was added 2.08 ml of 1.6 M butyllithium at −78° C. and the resulting mixture was stirred for 30 min. To the reaction mixture was added 133 mg of sulfur powder and the resulting mixture was stirred for an additional hour. Dil. hydrochloric acid was added to the mixture and the mixture was extracted with diethyl ether. The organic layer was washed with brine and the solvent was removed under reduced pressure. The residue was purified by the use of silica gel column chromatography gave 236 mg of 2-mercapto-5-(4-tolyl)furan.

¹H-NMR(CDCl₃): 2.38(3H, s), 6.66(1H, d, J=3.8 Hz), 6.72(11, d, J=3.8 Hz), 7.17 (2H, d, J=8.2 Hz), 7.58(1H, d, J=8.2 Hz).

2-mercapto-5-(4-tolyl)furan (70 mg) and pyrimidine derivative are condensed in a manner similar to that described in Example 242 to give 78 mg of compound E-7. The physical data was shown in Table 28.

TABLE 28

| Example No. | Compound No. | R[16] | R[18] | Y | $^1$H-NMR (δ) ppm |
|---|---|---|---|---|---|
| 242 | E-1 | Et | 4-Cl | 3-methyl-1,2,4-oxadiazol-5-yl (N—O, N) | 1.26(6H, t, J=7.5), 2.49(3H, s), 3.28(4H, br), 4.73(2H, s), 7.10(2H, d, J=8.8), 7.28(2H, d, J=8.8), 8.13(1H, s) |
| 243 | E-2 | Me | H | 3-methyl-1,2,4-oxadiazol-5-yl | 1.30(3H, t, J=7.2), 2.48(3H, s), 2.98(3H, d, J=3.4 1(2H, br), 4.50(2H, s), 7.46–7.50(3H, m), 8.06–8.09(2H, m), 8.40(1H, s) |
| 244 | E-3 | Et | 4-Cl | 2,5-dimethyloxazol-4-yl | 1.30(6H, t, J=7.2), 2.47(3H, s), 3.37(4H, br), 4.38(2H, s), 7.28(1H, s), 7.35(2H, d, J=8.6), 7.48(2H, d, J=8.6), 8.27(1H, s) |
| 245 | E-4 | Et | 4-Cl | 2,5-dimethyl-1,3,4-thiadiazol-yl | 1.29(6H, t, J=7.2), 2.46(3H, s), 3.37(4H, br), 4.55(2H, s), 7.44(2H, d, J=8.5), 7.80(2H, d, J=8.5), 8.23(1H, s) |
| 246 | E-5 | Me | 2-NH$_2$ | 3,5-dimethyl-1,2,4-triazol-yl (NH) | 1.36(3H, t, J=7.2), 2.52(3H, s), 3.10(3H, br), 3.47(2H, br), 4.31(2H, s), 5.49(2H, br), 6.71(1H, d, J=8.2), 6.72(1H, t, J=6.9), 7.13(1H, ddd, J=8.2, 6.9, 1.6), 7.97(1H, dd, J=6.9, 1.6), 8.43(1H, s) |
| 247 | E-6 | Et | 4-Cl | 1,3,5-trimethylpyrazol-4-yl | 1.29(3H, t, J=7.1), 2.47(3H, s), 3.36(4H, br), 3.78(3H, s), 3.93(2H, s), 6.55(1H, s), 7.34(2H, d, J=8.8), 7.66(2H, d, J=8.8), 7.85(1H, s) |
| 248 | E-7 | Et | 4-Me | 5-methylfuran-2-yl | 1.28(6H, t, J=7.2), 2.36(3H, s), 2.46(3H, s), 3.34(4H, br), 3.96(2H, s), 6.39(1H, d, J=3.4), 6.51(1H, d, J=3.4), 7.17(2H, d, J=7.9), 7.54(2H, d, J=7.9), 7.78(1H, s) |

Compounds F-1 to F-1142 shown in Tables 29 to 43 are able to synthesize in a manner similar to those described in Examples 1 to 248.

TABLE 29

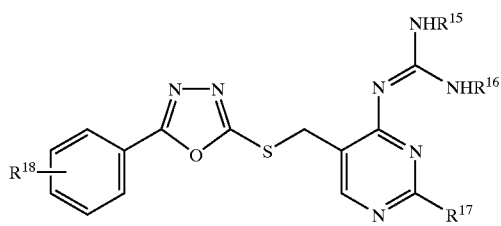

or

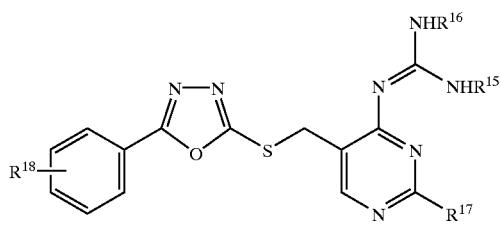

| Compound No. | R^15 | R^16 | R^17 | R^18 |
|---|---|---|---|---|
| F-1 | H | H | H | 4-NH$_2$ |
| F-2 | H | Me | H | 4-NH$_2$ |
| F-3 | H | Et | H | 4-NH$_2$ |
| F-4 | H | n-Pr | H | 4-NH$_2$ |
| F-5 | H | i-Pr | H | 4-NH$_2$ |
| F-6 | H | n-Bu | H | 4-NH$_2$ |
| F-7 | Me | n-Pr | H | 4-NH$_2$ |
| F-8 | Me | i-Pr | H | 4-NH$_2$ |
| F-9 | Me | n-Bu | H | 4-NH$_2$ |
| F-10 | Et | i-Pr | H | 4-NH$_2$ |
| F-11 | Et | n-Bu | H | 4-NH$_2$ |
| F-12 | n-Pr | n-Pr | H | 4-NH$_2$ |
| F-13 | n-Pr | i-Pr | H | 4-NH$_2$ |
| F-14 | n-Pr | n-Bu | H | 4-NH$_2$ |
| F-15 | i-Pr | i-Pr | H | 4-NH$_2$ |
| F-16 | i-Pr | n-Bu | H | 4-NH$_2$ |
| F-17 | n-Bu | n-Bu | H | 4-NH$_2$ |
| F-18 | H | H | Me | 4-NH$_2$ |
| F-19 | H | Me | Me | 4-NH$_2$ |
| F-20 | H | i-Pr | Me | 4-NH$_2$ |
| F-21 | H | n-Bu | Me | 4-NH$_2$ |
| F-22 | Me | n-Bu | Me | 4-NH$_2$ |
| F-23 | n-Pr | i-Pr | Me | 4-NH$_2$ |
| F-24 | n-Pr | n-Bu | Me | 4-NH$_2$ |
| F-25 | i-Pr | n-Bu | Me | 4-NH$_2$ |
| F-26 | H | H | Et | 4-NH$_2$ |
| F-27 | H | Me | Et | 4-NH$_2$ |
| F-28 | H | Et | Et | 4-NH$_2$ |
| F-29 | H | n-Pr | Et | 4-NH$_2$ |
| F-30 | H | n-Bu | Et | 4-NH$_2$ |
| F-31 | Me | Et | Et | 4-NH$_2$ |
| F-32 | Me | i-Pr | Et | 4-NH$_2$ |
| F-33 | Me | n-Bu | Et | 4-NH$_2$ |
| F-34 | Et | n-Pr | Et | 4-NH$_2$ |
| F-35 | Et | i-Pr | Et | 4-NH$_2$ |
| F-36 | Et | n-Bu | Et | 4-NH$_2$ |
| F-37 | n-Pr | i-Pr | Et | 4-NH$_2$ |
| F-38 | n-Pr | n-Bu | Et | 4-NH$_2$ |
| F-39 | i-Pr | i-Pr | Et | 4-NH$_2$ |
| F-40 | i-Pr | n-Bu | Et | 4-NH$_2$ |
| F-41 | n-Bu | n-Bu | Et | 4-NH$_2$ |
| F-42 | H | H | H | 4-NO$_2$ |
| F-43 | H | Me | H | 4-NO$_2$ |
| F-44 | H | Et | H | 4-NO$_2$ |
| F-45 | H | n-Pr | H | 4-NO$_2$ |
| F-46 | H | i-Pr | H | 4-NO$_2$ |
| F-47 | H | n-Bu | H | 4-NO$_2$ |
| F-48 | Me | n-Pr | H | 4-NO$_2$ |
| F-49 | Me | i-Pr | H | 4-NO$_2$ |
| F-50 | Me | n-Bu | H | 4-NO$_2$ |
| F-51 | Et | i-Pr | H | 4-NO$_2$ |

TABLE 29-continued

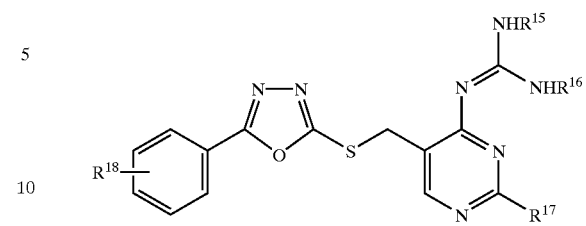

or

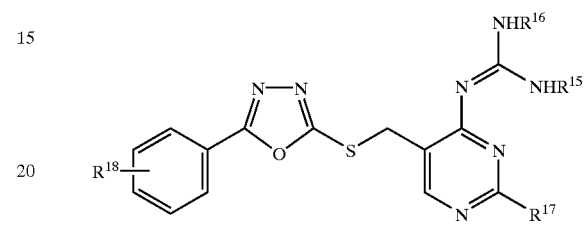

| Compound No. | R^15 | R^16 | R^17 | R^18 |
|---|---|---|---|---|
| F-52 | Et | n-Bu | H | 4-NO$_2$ |
| F-53 | n-Pr | i-Pr | H | 4-NO$_2$ |
| F-54 | n-Pr | n-Bu | H | 4-NO$_2$ |
| F-55 | i-Pr | i-Pr | H | 4-NO$_2$ |
| F-56 | i-Pr | n-Bu | H | 4-NO$_2$ |
| F-57 | n-Bu | n-Bu | H | 4-NO$_2$ |
| F-58 | H | H | Me | 4-NO$_2$ |
| F-59 | H | Me | Me | 4-NO$_2$ |
| F-60 | H | i-Pr | Me | 4-NO$_2$ |
| F-61 | H | n-Bu | Me | 4-NO$_2$ |
| F-62 | Me | n-Bu | Me | 4-NO$_2$ |
| F-63 | Et | Et | Me | 4-NO$_2$ |
| F-64 | n-Pr | i-Pr | Me | 4-NO$_2$ |
| F-65 | n-Pr | n-Bu | Me | 4-NO$_2$ |
| F-66 | i-Pr | n-Bu | Me | 4-NO$_2$ |
| F-67 | H | H | Et | 4-NO$_2$ |
| F-68 | H | Me | Et | 4-NO$_2$ |
| F-69 | H | Et | Et | 4-NO$_2$ |
| F-70 | H | n-Pr | Et | 4-NO$_2$ |
| F-71 | H | i-Pr | Et | 4-NO$_2$ |
| F-72 | H | n-Bu | Et | 4-NO$_2$ |
| F-73 | Me | Et | Et | 4-NO$_2$ |
| F-74 | Me | i-Pr | Et | 4-NO$_2$ |
| F-75 | Me | n-Bu | Et | 4-NO$_2$ |
| F-76 | Et | i-Pr | Et | 4-NO$_2$ |
| F-77 | Et | n-Bu | Et | 4-NO$_2$ |
| F-78 | n-Pr | i-Pr | Et | 4-NO$_2$ |
| F-79 | n-Pr | n-Bu | Et | 4-NO$_2$ |
| F-80 | i-Pr | i-Pr | Et | 4-NO$_2$ |

TABLE 30

| Compound No. | R^15 | R^16 | R^17 | R^18 |
|---|---|---|---|---|
| F-81 | i-Pr | n-Bu | Et | 4-NO$_2$ |
| F-82 | n-Bu | n-Bu | Et | 4-NO$_2$ |
| F-83 | H | H | H | 2-F-4-NH$_2$ |
| F-84 | H | Me | H | 2-F-4-NH$_2$ |
| F-85 | H | Et | H | 2-F-4-NH$_2$ |
| F-86 | H | n-Pr | H | 2-F-4-NH$_2$ |
| F-87 | H | i-Pr | H | 2-F-4-NH$_2$ |
| F-88 | H | n-Bu | H | 2-F-4-NH$_2$ |
| F-89 | Me | Me | H | 2-F-4-NH$_2$ |
| F-90 | Me | Et | H | 2-F-4-NH$_2$ |
| F-91 | Me | n-Pr | H | 2-F-4-NH$_2$ |
| F-92 | Me | i-Pr | H | 2-F-4-NH$_2$ |
| F-93 | Me | n-Bu | H | 2-F-4-NH$_2$ |
| F-94 | Et | Et | H | 2-F-4-NH$_2$ |

TABLE 30-continued

| Compound No. | R15 | R16 | R17 | R18 |
|---|---|---|---|---|
| F-95 | Et | n-Pr | H | 2-F-4-NH2 |
| F-96 | Et | i-Pr | H | 2-F-4-NH2 |
| F-97 | Et | n-Bu | H | 2-F-4-NH2 |
| F-98 | n-Pr | n-Pr | H | 2-F-4-NH2 |
| F-99 | n-Pr | i-Pr | H | 2-F-4-NH2 |
| F-100 | n-Pr | n-Bu | H | 2-F-4-NH2 |
| F-101 | i-Pr | i-Pr | H | 2-F-4-NH2 |
| F-102 | i-Pr | n-Bu | H | 2-F-4-NH2 |
| F-103 | n-Bu | n-Bu | H | 2-F-4-NH2 |
| F-104 | H | H | Me | 2-F-4-NH2 |
| F-105 | H | Me | Me | 2-F-4-NH2 |
| F-106 | H | Et | Me | 2-F-4-NH2 |
| F-107 | H | n-Pr | Me | 2-F-4-NH2 |
| F-108 | H | i-Pr | Me | 2-F-4-NH2 |
| F-109 | H | n-Bu | Me | 2-F-4-NH2 |
| F-110 | Me | Me | Me | 2-F-4-NH2 |
| F-111 | Me | Et | Me | 2-F-4-NH2 |
| F-112 | Me | n-Pr | Me | 2-F-4-NH2 |
| F-113 | Me | i-Pr | Me | 2-F-4-NH2 |
| F-114 | Me | n-Bu | Me | 2-F-4-NH2 |
| F-115 | Et | n-Pr | Me | 2-F-4-NH2 |
| F-116 | Et | i-Pr | Me | 2-F-4-NH2 |
| F-117 | Et | n-Bu | Me | 2-F-4-NH2 |
| F-118 | n-Pr | n-Pr | Me | 2-F-4-NH2 |
| F-119 | n-Pr | i-Pr | Me | 2-F-4-NH2 |
| F-120 | n-Pr | n-Bu | Me | 2-F-4-NH2 |
| F-121 | i-Pr | i-Pr | Me | 2-F-4-NH2 |
| F-122 | i-Pr | n-Bu | Me | 2-F-4-NH2 |
| F-123 | n-Bu | n-Bu | Me | 2-F-4-NH2 |
| F-124 | H | H | Et | 2-F-4-NH2 |
| F-125 | H | Me | Et | 2-F-4-NH2 |
| F-126 | H | Et | Et | 2-F-4-NH2 |
| F-127 | H | n-Pr | Et | 2-F-4-NH2 |
| F-128 | H | i-Pr | Et | 2-F-4-NH2 |
| F-129 | H | n-Bu | Et | 2-F-4-NH2 |
| F-130 | Me | Me | Et | 2-F-4-NH2 |
| F-131 | Me | Et | Et | 2-F-4-NH2 |
| F-132 | Me | n-Pr | Et | 2-F-4-NH2 |
| F-133 | Me | i-Pr | Et | 2-F-4-NH2 |
| F-134 | Me | n-Bu | Et | 2-F-4-NH2 |
| F-135 | Et | Et | Et | 2-F-4-NH2 |
| F-136 | Et | n-Pr | Et | 2-F-4-NH2 |
| F-137 | Et | i-Pr | Et | 2-F-4-NH2 |
| F-138 | Et | n-Bu | Et | 2-F-4-NH2 |
| F-139 | n-Pr | n-Pr | Et | 2-F-4-NH2 |
| F-140 | n-Pr | i-Pr | Et | 2-F-4-NH2 |
| F-141 | n-Pr | n-Bu | Et | 2-F-4-NH2 |
| F-142 | i-Pr | i-Pr | Et | 2-F-4-NH2 |
| F-143 | i-Pr | n-Bu | Et | 2-F-4-NH2 |
| F-144 | n-Bu | n-Bu | Et | 2-F-4-NH2 |
| F-145 | H | H | H | 2-F-4-NO2 |
| F-146 | H | Me | H | 2-F-4-NO2 |
| F-147 | H | Et | H | 2-F-4-NO2 |
| F-148 | H | n-Pr | H | 2-F-4-NO2 |
| F-149 | H | i-Pr | H | 2-F-4-NO2 |
| F-150 | H | n-Bu | H | 2-F-4-NO2 |
| F-151 | Me | Me | H | 2-F-4-NO2 |
| F-152 | Me | Et | H | 2-F-4-NO2 |
| F-153 | Me | n-Pr | H | 2-F-4-NO2 |
| F-154 | Me | i-Pr | H | 2-F-4-NO2 |
| F-155 | Me | n-Bu | H | 2-F-4-NO2 |
| F-156 | Et | Et | H | 2-F-4-NO2 |
| F-157 | Et | n-Pr | H | 2-F-4-NO2 |
| F-158 | Et | i-Pr | H | 2-F-4-NO2 |
| F-159 | Et | n-Bu | H | 2-F-4-NO2 |
| F-160 | n-Pr | n-Pr | H | 2-F-4-NO2 |

TABLE 31

| Compound No. | R15 | R16 | R17 | R18 |
|---|---|---|---|---|
| F-161 | n-Pr | i-Pr | H | 2-F-4-NO2 |
| F-162 | n-Pr | n-Bu | H | 2-F-4-NO2 |

TABLE 31-continued

| Compound No. | R15 | R16 | R17 | R18 |
|---|---|---|---|---|
| F-163 | i-Pr | i-Pr | H | 2-F-4-NO2 |
| F-164 | i-Pr | n-Bu | H | 2-F-4-NO2 |
| F-165 | n-Bu | n-Bu | H | 2-F-4-NO2 |
| F-166 | H | H | Me | 2-F-4-NO2 |
| F-167 | H | Me | Me | 2-F-4-NO2 |
| F-168 | H | Et | Me | 2-F-4-NO2 |
| F-169 | H | n-Pr | Me | 2-F-4-NO2 |
| F-170 | H | i-Pr | Me | 2-F-4-NO2 |
| F-171 | H | n-Bu | Me | 2-F-4-NO2 |
| F-172 | Me | Me | Me | 2-F-4-NO2 |
| F-173 | Me | Et | Me | 2-F-4-NO2 |
| F-174 | Me | n-Pr | Me | 2-F-4-NO2 |
| F-175 | Me | i-Pr | Me | 2-F-4-NO2 |
| F-176 | Me | n-Bu | Me | 2-F-4-NO2 |
| F-177 | Et | n-Pr | Me | 2-F-4-NO2 |
| F-178 | Et | i-Pr | Me | 2-F-4-NO2 |
| F-179 | Et | n-Bu | Me | 2-F-4-NO2 |
| F-180 | n-Pr | n-Pr | Me | 2-F-4-NO2 |
| F-181 | n-Pr | i-Pr | Me | 2-F-4-NO2 |
| F-182 | n-Pr | n-Bu | Me | 2-F-4-NO2 |
| F-183 | i-Pr | i-Pr | Me | 2-F-4-NO2 |
| F-184 | i-Pr | n-Bu | Me | 2-F-4-NO2 |
| F-185 | n-Bu | n-Bu | Me | 2-F-4-NO2 |
| F-186 | H | H | Et | 2-F-4-NO2 |
| F-187 | H | Me | Et | 2-F-4-NO2 |
| F-188 | H | Et | Et | 2-F-4-NO2 |
| F-189 | H | n-Pr | Et | 2-F-4-NO2 |
| F-190 | H | i-Pr | Et | 2-F-4-NO2 |
| F-191 | H | n-Bu | Et | 2-F-4-NO2 |
| F-192 | Me | Me | Et | 2-F-4-NO2 |
| F-193 | Me | Et | Et | 2-F-4-NO2 |
| F-194 | Me | n-Pr | Et | 2-F-4-NO2 |
| F-195 | Me | i-Pr | Et | 2-F-4-NO2 |
| F-196 | Me | n-Bu | Et | 2-F-4-NO2 |
| F-197 | Et | Et | Et | 2-F-4-NO2 |
| F-198 | Et | n-Pr | Et | 2-F-4-NO2 |
| F-199 | Et | i-Pr | Et | 2-F-4-NO2 |
| F-200 | Et | n-Bu | Et | 2-F-4-NO2 |
| F-201 | n-Pr | n-Pr | Et | 2-F-4-NO2 |
| F-202 | n-Pr | i-Pr | Et | 2-F-4-NO2 |
| F-203 | n-Pr | n-Bu | Et | 2-F-4-NO2 |
| F-204 | i-Pr | i-Pr | Et | 2-F-4-NO2 |
| F-205 | i-Pr | n-Bu | Et | 2-F-4-NO2 |
| F-206 | n-Bu | n-Bu | Et | 2-F-4-NO2 |
| F-207 | H | H | H | 2-OMe-4-NH2 |
| F-208 | H | Me | H | 2-OMe-4-NH2 |
| F-209 | H | Et | H | 2-OMe-4-NH2 |
| F-210 | H | n-Pr | H | 2-OMe-4-NH2 |
| F-211 | H | i-Pr | H | 2-OMe-4-NH2 |
| F-212 | H | n-Bu | H | 2-OMe-4-NH2 |
| F-213 | Me | Me | H | 2-OMe-4-NH2 |
| F-214 | Me | Et | H | 2-OMe-4-NH2 |
| F-215 | Me | n-Pr | H | 2-OMe-4-NH2 |
| F-216 | Me | i-Pr | H | 2-OMe-4-NH2 |
| F-217 | Me | n-Bu | H | 2-OMe-4-NH2 |
| F-218 | Et | Et | H | 2-OMe-4-NH2 |
| F-219 | Et | n-Pr | H | 2-OMe-4-NH2 |
| F-220 | Et | i-Pr | H | 2-OMe-4-NH2 |
| F-221 | Et | n-Bu | H | 2-OMe-4-NH2 |
| F-222 | n-Pr | n-Pr | H | 2-OMe-4-NH2 |
| F-223 | n-Pr | i-Pr | H | 2-OMe-4-NH2 |
| F-224 | n-Pr | n-Bu | H | 2-OMe-4-NH2 |
| F-225 | i-Pr | i-Pr | H | 2-OMe-4-NH2 |
| F-226 | i-Pr | n-Bu | H | 2-OMe-4-NH2 |
| F-227 | n-Bu | n-Bu | H | 2-OMe-4-NH2 |
| F-228 | H | H | Me | 2-OMe-4-NH2 |
| F-229 | H | Me | Me | 2-OMe-4-NH2 |
| F-230 | H | Et | Me | 2-OMe-4-NH2 |
| F-231 | H | n-Pr | Me | 2-OMe-4-NH2 |
| F-232 | H | i-Pr | Me | 2-OMe-4-NH2 |
| F-233 | H | n-Bu | Me | 2-OMe-4-NH2 |
| F-234 | Me | Me | Me | 2-OMe-4-NH2 |
| F-235 | Me | Et | Me | 2-OMe-4-NH2 |
| F-236 | Me | n-Pr | Me | 2-OMe-4-NH2 |
| F-237 | Me | i-Pr | Me | 2-OMe-4-NH2 |
| F-238 | Me | n-Bu | Me | 2-OMe-4-NH2 |

TABLE 31-continued

| Compound No. | $R^{15}$ | $R^{16}$ | $R^{17}$ | $R^{18}$ |
| --- | --- | --- | --- | --- |
| F-239 | Et | n-Pr | Me | 2-OMe-4-$NH_2$ |
| F-240 | Et | i-Pr | Me | 2-OMe-4-$NH_2$ |

TABLE 32

| Compound No. | $R^{15}$ | $R^{16}$ | $R^{17}$ | $R^{18}$ |
| --- | --- | --- | --- | --- |
| F-241 | Et | n-Bu | Me | 2-OMe-4-$NH_2$ |
| F-242 | n-Pr | i-Pr | Me | 2-OMe-4-$NH_2$ |
| F-243 | n-Pr | n-Bu | Me | 2-OMe-4-$NH_2$ |
| F-244 | i-Pr | i-Pr | Me | 2-OMe-4-$NH_2$ |
| F-245 | i-Pr | n-Bu | Me | 2-OMe-4-$NH_2$ |
| F-246 | n-Bu | n-Bu | Me | 2-OMe-4-$NH_2$ |
| F-247 | H | H | Et | 2-OMe-4-$NH_2$ |
| F-248 | H | Me | Et | 2-OMe-4-$NH_2$ |
| F-249 | H | Et | Et | 2-OMe-4-$NH_2$ |
| F-250 | H | n-Pr | Et | 2-OMe-4-$NH_2$ |
| F-251 | H | i-Pr | Et | 2-OMe-4-$NH_2$ |
| F-252 | H | n-Bu | Et | 2-OMe-4-$NH_2$ |
| F-253 | Me | Me | Et | 2-OMe-4-$NH_2$ |
| F-254 | Me | Et | Et | 2-OMe-4-$NH_2$ |
| F-255 | Me | n-Pr | Et | 2-OMe-4-$NH_2$ |
| F-256 | Me | i-Pr | Et | 2-OMe-4-$NH_2$ |
| F-257 | Me | n-Bu | Et | 2-OMe-4-$NH_2$ |
| F-258 | Et | Et | Et | 2-OMe-4-$NH_2$ |
| F-259 | Et | n-Pr | Et | 2-OMe-4-$NH_2$ |
| F-260 | Et | i-Pr | Et | 2-OMe-4-$NH_2$ |
| F-261 | Et | n-Bu | Et | 2-OMe-4-$NH_2$ |
| F-262 | n-Pr | n-Pr | Et | 2-OMe-4-$NH_2$ |
| F-263 | n-Pr | i-Pr | Et | 2-OMe-4-$NH_2$ |
| F-264 | n-Pr | n-Bu | Et | 2-OMe-4-$NH_2$ |
| F-265 | i-Pr | i-Pr | Et | 2-OMe-4-$NH_2$ |
| F-266 | i-Pr | n-Bu | Et | 2-OMe-4-$NH_2$ |
| F-267 | n-Bu | n-Bu | Et | 2-OMe-4-$NH_2$ |
| F-268 | H | H | H | 2-OMe-4-$NO_2$ |
| F-269 | H | Me | H | 2-OMe-4-$NO_2$ |
| F-270 | H | Et | H | 2-OMe-4-$NO_2$ |
| F-271 | H | n-Pr | H | 2-OMe-4-$NO_2$ |
| F-272 | H | i-Pr | H | 2-OMe-4-$NO_2$ |
| F-273 | H | n-Bu | H | 2-OMe-4-$NO_2$ |
| F-274 | Me | Me | H | 2-OMe-4-$NO_2$ |
| F-275 | Me | Et | H | 2-OMe-4-$NO_2$ |
| F-276 | Me | n-Pr | H | 2-OMe-4-$NO_2$ |
| F-277 | Me | i-Pr | H | 2-OMe-4-$NO_2$ |
| F-278 | Me | n-Bu | H | 2-OMe-4-$NO_2$ |
| F-279 | Et | n-Pr | H | 2-OMe-4-$NO_2$ |
| F-280 | Et | i-Pr | H | 2-OMe-4-$NO_2$ |
| F-281 | Et | n-Bu | H | 2-OMe-4-$NO_2$ |
| F-282 | n-Pr | n-Pr | H | 2-OMe-4-$NO_2$ |
| F-283 | n-Pr | i-Pr | H | 2-OMe-4-$NO_2$ |
| F-284 | n-Pr | n-Bu | H | 2-OMe-4-$NO_2$ |
| F-285 | i-Pr | i-Pr | H | 2-OMe-4-$NO_2$ |
| F-286 | i-Pr | n-Bu | H | 2-OMe-4-$NO_2$ |
| F-287 | n-Bu | n-Bu | H | 2-OMe-4-$NO_2$ |
| F-288 | H | H | Me | 2-OMe-4-$NO_2$ |
| F-289 | H | Me | Me | 2-OMe-4-$NO_2$ |
| F-290 | H | Et | Me | 2-OMe-4-$NO_2$ |
| F-291 | H | n-Pr | Me | 2-OMe-4-$NO_2$ |
| F-292 | H | i-Pr | Me | 2-OMe-4-$NO_2$ |
| F-293 | H | n-Bu | Me | 2-OMe-4-$NO_2$ |
| F-294 | Me | Et | Me | 2-OMe-4-$NO_2$ |
| F-295 | Me | n-Pr | Me | 2-OMe-4-$NO_2$ |
| F-296 | Me | i-Pr | Me | 2-OMe-4-$NO_2$ |
| F-297 | Me | n-Bu | Me | 2-OMe-4-$NO_2$ |
| F-298 | Et | n-Pr | Me | 2-OMe-4-$NO_2$ |
| F-299 | Et | i-Pr | Me | 2-OMe-4-$NO_2$ |
| F-300 | Et | n-Bu | Me | 2-OMe-4-$NO_2$ |
| F-301 | n-Pr | n-Pr | Me | 2-OMe-4-$NO_2$ |
| F-302 | n-Pr | i-Pr | Me | 2-OMe-4-$NO_2$ |
| F-303 | n-Pr | n-Bu | Me | 2-OMe-4-$NO_2$ |
| F-304 | i-Pr | i-Pr | Me | 2-OMe-4-$NO_2$ |
| F-305 | i-Pr | n-Bu | Me | 2-OMe-4-$NO_2$ |
| F-306 | n-Bu | n-Bu | Me | 2-OMe-4-$NO_2$ |

TABLE 32-continued

| Compound No. | $R^{15}$ | $R^{16}$ | $R^{17}$ | $R^{18}$ |
| --- | --- | --- | --- | --- |
| F-307 | H | H | Et | 2-OMe-4-$NO_2$ |
| F-308 | H | Me | Et | 2-OMe-4-$NO_2$ |
| F-309 | H | Et | Et | 2-OMe-4-$NO_2$ |
| F-310 | H | n-Pr | Et | 2-OMe-4-$NO_2$ |
| F-311 | H | i-Pr | Et | 2-OMe-4-$NO_2$ |
| F-312 | H | n-Bu | Et | 2-OMe-4-$NO_2$ |
| F-313 | Me | Me | Et | 2-OMe-4-$NO_2$ |
| F-314 | Me | Et | Et | 2-OMe-4-$NO_2$ |
| F-315 | Me | n-Pr | Et | 2-OMe-4-$NO_2$ |
| F-316 | Me | i-Pr | Et | 2-OMe-4-$NO_2$ |
| F-317 | Me | n-Bu | Et | 2-OMe-4-$NO_2$ |
| F-318 | Et | Et | Et | 2-OMe-4-$NO_2$ |
| F-319 | Et | n-Pr | Et | 2-OMe-4-$NO_2$ |
| F-320 | Et | i-Pr | Et | 2-OMe-4-$NO_2$ |

TABLE 33

| Compound No. | $R^{15}$ | $R^{16}$ | $R^{17}$ | $R^{18}$ |
| --- | --- | --- | --- | --- |
| F-321 | Et | n-Bu | Et | 2-OMe-4-$NO_2$ |
| F-322 | n-Pr | n-Pr | Et | 2-OMe-4-$NO_2$ |
| F-323 | n-Pr | i-Pr | Et | 2-OMe-4-$NO_2$ |
| F-324 | n-Pr | n-Bu | Et | 2-OMe-4-$NO_2$ |
| F-325 | i-Pr | i-Pr | Et | 2-OMe-4-$NO_2$ |
| F-326 | i-Pr | n-Bu | Et | 2-OMe-4-$NO_2$ |
| F-327 | n-Bu | n-Bu | Et | 2-OMe-4-$NO_2$ |
| F-328 | H | H | H | 2-$NH_2$-4-F |
| F-329 | H | Me | H | 2-$NH_2$-4-F |
| F-330 | H | Et | H | 2-$NH_2$-4-F |
| F-331 | H | n-Pr | H | 2-$NH_2$-4-F |
| F-332 | H | i-Pr | H | 2-$NH_2$-4-F |
| F-333 | H | n-Bu | H | 2-$NH_2$-4-F |
| F-334 | Me | Me | H | 2-$NH_2$-4-F |
| F-335 | Me | Et | H | 2-$NH_2$-4-F |
| F-336 | Me | n-Pr | H | 2-$NH_2$-4-F |
| F-337 | Me | i-Pr | H | 2-$NH_2$-4-F |
| F-338 | Me | n-Bu | H | 2-$NH_2$-4-F |
| F-339 | Et | n-Pr | H | 2-$NH_2$-4-F |
| F-340 | Et | i-Pr | H | 2-$NH_2$-4-F |
| F-341 | Et | n-Bu | H | 2-$NH_2$-4-F |
| F-342 | n-Pr | n-Pr | H | 2-$NH_2$-4-F |
| F-343 | n-Pr | i-Pr | H | 2-$NH_2$-4-F |
| F-344 | n-Pr | n-Bu | H | 2-$NH_2$-4-F |
| F-345 | i-Pr | i-Pr | H | 2-$NH_2$-4-F |
| F-346 | i-Pr | n-Bu | H | 2-$NH_2$-4-F |
| F-347 | n-Bu | n-Bu | H | 2-$NH_2$-4-F |
| F-348 | H | H | Me | 2-$NH_2$-4-F |
| F-349 | H | Me | Me | 2-$NH_2$-4-F |
| F-350 | H | Et | Me | 2-$NH_2$-4-F |
| F-351 | H | n-Pr | Me | 2-$NH_2$-4-F |
| F-352 | H | i-Pr | Me | 2-$NH_2$-4-F |
| F-353 | H | n-Bu | Me | 2-$NH_2$-4-F |
| F-354 | Me | Me | Me | 2-$NH_2$-4-F |
| F-355 | Me | Et | Me | 2-$NH_2$-4-F |
| F-356 | Me | n-Pr | Me | 2-$NH_2$-4-F |
| F-357 | Me | i-Pr | Me | 2-$NH_2$-4-F |
| F-358 | Me | n-Bu | Me | 2-$NH_2$-4-F |
| F-359 | Et | n-Pr | Me | 2-$NH_2$-4-F |
| F-360 | Et | i-Pr | Me | 2-$NH_2$-4-F |
| F-361 | Et | n-Bu | Me | 2-$NH_2$-4-F |
| F-362 | n-Pr | n-Pr | Me | 2-$NH_2$-4-F |
| F-363 | n-Pr | i-Pr | Me | 2-$NH_2$-4-F |
| F-364 | n-Pr | n-Bu | Me | 2-$NH_2$-4-F |
| F-365 | i-Pr | i-Pr | Me | 2-$NH_2$-4-F |
| F-366 | i-Pr | n-Bu | Me | 2-$NH_2$-4-F |
| F-367 | n-Bu | n-Bu | Me | 2-$NH_2$-4-F |
| F-368 | H | H | Et | 2-$NH_2$-4-F |
| F-369 | H | Me | Et | 2-$NH_2$-4-F |
| F-370 | H | Et | Et | 2-$NH_2$-4-F |
| F-371 | H | n-Pr | Et | 2-$NH_2$-4-F |
| F-372 | H | i-Pr | Et | 2-$NH_2$-4-F |
| F-373 | H | n-Bu | Et | 2-$NH_2$-4-F |
| F-374 | Me | Me | Et | 2-$NH_2$-4-F |

TABLE 33-continued

| Compound No. | $R^{15}$ | $R^{16}$ | $R^{17}$ | $R^{18}$ |
|---|---|---|---|---|
| F-375 | Me | Et | Et | 2-$NH_2$-4-F |
| F-376 | Me | n-Pr | Et | 2-$NH_2$-4-F |
| F-377 | Me | i-Pr | Et | 2-$NH_2$-4-F |
| F-378 | Me | n-Bu | Et | 2-$NH_2$-4-F |
| F-379 | Et | Et | Et | 2-$NH_2$-4-F |
| F-380 | Et | n-Pr | Et | 2-$NH_2$-4-F |
| F-381 | Et | i-Pr | Et | 2-$NH_2$-4-F |
| F-382 | Et | n-Bu | Et | 2-$NH_2$-4-F |
| F-383 | n-Pr | i-Pr | Et | 2-$NH_2$-4-F |
| F-384 | n-Pr | n-Bu | Et | 2-$NH_2$-4-F |
| F-385 | i-Pr | i-Pr | Et | 2-$NH_2$-4-F |
| F-386 | i-Pr | n-Bu | Et | 2-$NH_2$-4-F |
| F-387 | n-Bu | n-Bu | Et | 2-$NH_2$-4-F |
| F-388 | H | H | H | 2-$NO_2$-4-F |
| F-389 | H | Me | H | 2-$NO_2$-4-F |
| F-390 | H | Et | H | 2-$NO_2$-4-F |
| F-391 | H | n-Pr | H | 2-$NO_2$-4-F |
| F-392 | H | i-Pr | H | 2-$NO_2$-4-F |
| F-393 | H | n-Bu | H | 2-$NO_2$-4-F |
| F-394 | Me | Me | H | 2-$NO_2$-4-F |
| F-395 | Me | Et | H | 2-$NO_2$-4-F |
| F-396 | Me | n-Pr | H | 2-$NO_2$-4-F |
| F-397 | Me | i-Pr | H | 2-$NO_2$-4-F |
| F-398 | Me | n-Bu | H | 2-$NO_2$-4-F |
| F-399 | Et | Et | H | 2-$NO_2$-4-F |
| F-400 | Et | n-Pr | H | 2-$NO_2$-4-F |

TABLE 34

| Compound No. | $R^{15}$ | $R^{16}$ | $R^{17}$ | $R^{18}$ |
|---|---|---|---|---|
| F-401 | Et | i-Pr | H | 2-$NO_2$-4-F |
| F-402 | Et | n-Bu | H | 2-$NO_2$-4-F |
| F-403 | n-Pr | n-Pr | H | 2-$NO_2$-4-F |
| F-404 | n-Pr | i-Pr | H | 2-$NO_2$-4-F |
| F-405 | n-Pr | n-Bu | H | 2-$NO_2$-4-F |
| F-406 | i-Pr | i-Pr | H | 2-$NO_2$-4-F |
| F-407 | i-Pr | n-Bu | H | 2-$NO_2$-4-F |
| F-408 | n-Bu | n-Bu | H | 2-$NO_2$-4-F |
| F-409 | H | H | Me | 2-$NO_2$-4-F |
| F-410 | H | Me | Me | 2-$NO_2$-4-F |
| F-411 | H | Et | Me | 2-$NO_2$-4-F |
| F-412 | H | n-Pr | Me | 2-$NO_2$-4-F |
| F-413 | H | i-Pr | Me | 2-$NO_2$-4-F |
| F-414 | H | n-Bu | Me | 2-$NO_2$-4-F |
| F-415 | Me | Me | Me | 2-$NO_2$-4-F |
| F-416 | Me | Et | Me | 2-$NO_2$-4-F |
| F-417 | Me | n-Pr | Me | 2-$NO_2$-4-F |
| F-418 | Me | i-Pr | Me | 2-$NO_2$-4-F |
| F-419 | Me | n-Bu | Me | 2-$NO_2$-4-F |
| F-420 | Et | Et | Me | 2-$NO_2$-4-F |
| F-421 | Et | n-Pr | Me | 2-$NO_2$-4-F |
| F-422 | Et | i-Pr | Me | 2-$NO_2$-4-F |
| F-423 | Et | n-Bu | Me | 2-$NO_2$-4-F |
| F-424 | n-Pr | n-Pr | Me | 2-$NO_2$-4-F |
| F-425 | n-Pr | i-Pr | Me | 2-$NO_2$-4-F |
| F-426 | n-Pr | n-Bu | Me | 2-$NO_2$-4-F |
| F-427 | i-Pr | i-Pr | Me | 2-$NO_2$-4-F |
| F-428 | i-Pr | n-Bu | Me | 2-$NO_2$-4-F |
| F-429 | n-Bu | n-Bu | Me | 2-$NO_2$-4-F |
| F-430 | H | H | Et | 2-$NO_2$-4-F |
| F-431 | H | Me | Et | 2-$NO_2$-4-F |
| F-432 | H | Et | Et | 2-$NO_2$-4-F |
| F-433 | H | n-Pr | Et | 2-$NO_2$-4-F |
| F-434 | H | i-Pr | Et | 2-$NO_2$-4-F |
| F-435 | H | n-Bu | Et | 2-$NO_2$-4-F |
| F-436 | Me | Me | Et | 2-$NO_2$-4-F |
| F-437 | Me | Et | Et | 2-$NO_2$-4-F |
| F-438 | Me | n-Pr | Et | 2-$NO_2$-4-F |
| F-439 | Me | i-Pr | Et | 2-$NO_2$-4-F |
| F-440 | Me | n-Bu | Et | 2-$NO_2$-4-F |
| F-441 | Et | Et | Et | 2-$NO_2$-4-F |
| F-442 | Et | n-Pr | Et | 2-$NO_2$-4-F |

TABLE 34-continued

| Compound No. | $R^{15}$ | $R^{16}$ | $R^{17}$ | $R^{18}$ |
|---|---|---|---|---|
| F-443 | Et | i-Pr | Et | 2-$NO_2$-4-F |
| F-444 | Et | n-Bu | Et | 2-$NO_2$-4-F |
| F-445 | n-Pr | n-Pr | Et | 2-$NO_2$-4-F |
| F-446 | n-Pr | i-Pr | Et | 2-$NO_2$-4-F |
| F-447 | n-Pr | n-Bu | Et | 2-$NO_2$-4-F |
| F-448 | i-Pr | i-Pr | Et | 2-$NO_2$-4-F |
| F-449 | i-Pr | n-Bu | Et | 2-$NO_2$-4-F |
| F-450 | n-Bu | n-Bu | Et | 2-$NO_2$-4-F |
| F-451 | H | Et | H | 2-Cl-4-$NH_2$ |
| F-452 | Me | Me | H | 2-Cl-4-$NH_2$ |
| F-453 | Me | Et | H | 2-Cl-4-$NH_2$ |
| F-454 | Me | n-Pr | H | 2-Cl-4-$NH_2$ |
| F-455 | Me | i-Pr | H | 2-Cl-4-$NH_2$ |
| F-456 | Me | n-Bu | H | 2-Cl-4-$NH_2$ |
| F-457 | Et | Et | H | 2-Cl-4-$NH_2$ |
| F-458 | Et | n-Pr | H | 2-Cl-4-$NH_2$ |
| F-459 | Et | i-Pr | H | 2-Cl-4-$NH_2$ |
| F-460 | n-Pr | n-Pr | H | 2-Cl-4-$NH_2$ |
| F-461 | n-Pr | i-Pr | H | 2-Cl-4-$NH_2$ |
| F-462 | i-Pr | i-Pr | H | 2-Cl-4-$NH_2$ |
| F-463 | H | Et | Me | 2-Cl-4-$NH_2$ |
| F-464 | Me | Me | Me | 2-Cl-4-$NH_2$ |
| F-465 | Me | Et | Me | 2-Cl-4-$NH_2$ |
| F-466 | Me | n-Pr | Me | 2-Cl-4-$NH_2$ |
| F-467 | Me | i-Pr | Me | 2-Cl-4-$NH_2$ |
| F-468 | Me | n-Bu | Me | 2-Cl-4-$NH_2$ |
| F-469 | Et | n-Pr | Me | 2-Cl-4-$NH_2$ |
| F-470 | Et | i-Pr | Me | 2-Cl-4-$NH_2$ |
| F-471 | n-Pr | n-Pr | Me | 2-Cl-4-$NH_2$ |
| F-472 | n-Pr | i-Pr | Me | 2-Cl-4-$NH_2$ |
| F-473 | i-Pr | i-Pr | Me | 2-Cl-4-$NH_2$ |
| F-474 | H | Et | Et | 2-Cl-4-$NH_2$ |
| F-475 | Me | Me | Et | 2-Cl-4-$NH_2$ |
| F-476 | Me | Et | Et | 2-Cl-4-$NH_2$ |
| F-477 | Me | n-Pr | Et | 2-Cl-4-$NH_2$ |
| F-478 | Me | i-Pr | Et | 2-Cl-4-$NH_2$ |
| F-479 | Me | n-Bu | Et | 2-Cl-4-$NH_2$ |
| F-480 | Et | Et | Et | 2-Cl-4-$NH_2$ |

TABLE 35

| Compound No. | $R^{15}$ | $R^{16}$ | $R^{17}$ | $R^{18}$ |
|---|---|---|---|---|
| F-481 | Et | n-Pr | Et | 2-Cl-4-$NH_2$ |
| F-482 | Et | i-Pr | Et | 2-Cl-4-$NH_2$ |
| F-483 | H | Et | H | 2-Me-4-$NH_2$ |
| F-484 | Me | Me | H | 2-Me-4-$NH_2$ |
| F-485 | Me | Et | H | 2-Me-4-$NH_2$ |
| F-486 | Me | n-Pr | H | 2-Me-4-$NH_2$ |
| F-487 | Me | i-Pr | H | 2-Me-4-$NH_2$ |
| F-488 | Me | n-Bu | H | 2-Me-4-$NH_2$ |
| F-489 | Et | Et | H | 2-Me-4-$NH_2$ |
| F-490 | Et | n-Pr | H | 2-Me-4-$NH_2$ |
| F-491 | Et | i-Pr | H | 2-Me-4-$NH_2$ |
| F-492 | n-Pr | n-Pr | H | 2-Me-4-$NH_2$ |
| F-493 | n-Pr | i-Pr | H | 2-Me-4-$NH_2$ |
| F-494 | i-Pr | i-Pr | H | 2-Me-4-$NH_2$ |
| F-495 | H | Et | Me | 2-Me-4-$NH_2$ |
| F-496 | Me | Me | Me | 2-Me-4-$NH_2$ |
| F-497 | Me | Et | Me | 2-Me-4-$NH_2$ |
| F-498 | Me | n-Pr | Me | 2-Me-4-$NH_2$ |
| F-499 | Me | i-Pr | Me | 2-Me-4-$NH_2$ |
| F-500 | Me | n-Bu | Me | 2-Me-4-$NH_2$ |
| F-501 | Et | Et | Me | 2-Me-4-$NH_2$ |
| F-502 | Et | n-Pr | Me | 2-Me-4-$NH_2$ |
| F-503 | Et | i-Pr | Me | 2-Me-4-$NH_2$ |
| F-504 | n-Pr | n-Pr | Me | 2-Me-4-$NH_2$ |
| F-505 | n-Pr | i-Pr | Me | 2-Me-4-$NH_2$ |
| F-506 | i-Pr | i-Pr | Me | 2-Me-4-$NH_2$ |
| F-507 | H | Et | Et | 2-Me-4-$NH_2$ |
| F-508 | Me | Me | Et | 2-Me-4-$NH_2$ |
| F-509 | Me | Et | Et | 2-Me-4-$NH_2$ |
| F-510 | Me | n-Pr | Et | 2-Me-4-$NH_2$ |

TABLE 35-continued

| Compound No. | $R^{15}$ | $R^{16}$ | $R^{17}$ | $R^{18}$ |
|---|---|---|---|---|
| F-511 | Me | i-Pr | Et | 2-Me-4-NH$_2$ |
| F-512 | Me | n-Bu | Et | 2-Me-4-NH$_2$ |
| F-513 | Et | Et | Et | 2-Me-4-NH$_2$ |
| F-514 | Et | n-Pr | Et | 2-Me-4-NH$_2$ |
| F-515 | Et | i-Pr | Et | 2-Me-4-NH$_2$ |
| F-516 | H | Et | H | 2-CF$_3$-4-NH$_2$ |
| F-517 | Me | Me | H | 2-CF$_3$-4-NH$_2$ |
| F-518 | Me | Et | H | 2-CF$_3$-4-NH$_2$ |
| F-519 | Me | n-Pr | H | 2-CF$_3$-4-NH$_2$ |
| F-520 | Me | i-Pr | H | 2-CF$_3$-4-NH$_2$ |
| F-521 | Me | n-Bu | H | 2-CF$_3$-4-NH$_2$ |
| F-522 | Et | Et | H | 2-CF$_3$-4-NH$_2$ |
| F-523 | Et | n-Pr | H | 2-CF$_3$-4-NH$_2$ |
| F-524 | Et | i-Pr | H | 2-CF$_3$-4-NH$_2$ |
| F-525 | n-Pr | n-Pr | H | 2-CF$_3$-4-NH$_2$ |
| F-526 | n-Pr | i-Pr | H | 2-CF$_3$-4-NH$_2$ |
| F-527 | i-Pr | i-Pr | H | 2-CF$_3$-4-NH$_2$ |
| F-528 | H | Et | Me | 2-CF$_3$-4-NH$_2$ |
| F-529 | Me | Me | Me | 2-CF$_3$-4-NH$_2$ |
| F-530 | Me | Et | Me | 2-CF$_3$-4-NH$_2$ |
| F-531 | Me | n-Pr | Me | 2-CF$_3$-4-NH$_2$ |
| F-532 | Me | i-Pr | Me | 2-CF$_3$-4-NH$_2$ |
| F-533 | Me | n-Bu | Me | 2-CF$_3$-4-NH$_2$ |
| F-534 | Et | Et | Me | 2-CF$_3$-4-NH$_2$ |
| F-535 | Et | n-Pr | Me | 2-CF$_3$-4-NH$_2$ |
| F-536 | Et | i-Pr | Me | 2-CF$_3$-4-NH$_2$ |
| F-537 | n-Pr | n-Pr | Me | 2-CF$_3$-4-NH$_2$ |
| F-538 | n-Pr | i-Pr | Me | 2-CF$_3$-4-NH$_2$ |
| F-539 | i-Pr | i-Pr | Me | 2-CF$_3$-4-NH$_2$ |
| F-540 | Me | Et | Et | 2-CF$_3$-4-NH$_2$ |
| F-541 | Me | n-Pr | Et | 2-CF$_3$-4-NH$_2$ |
| F-542 | Me | i-Pr | Et | 2-CF$_3$-4-NH$_2$ |
| F-543 | Me | n-Bu | Et | 2-CF$_3$-4-NH$_2$ |
| F-544 | Me | i-Pr | Et | 2-CF$_3$-4-NH$_2$ |
| F-545 | Me | n-Bu | Et | 2-CF$_3$-4-NH$_2$ |
| F-546 | Et | Et | Et | 2-CF$_3$-4-NH$_2$ |
| F-547 | Et | n-Pr | Et | 2-CF$_3$-4-NH$_2$ |
| F-548 | Et | i-Pr | Et | 2-CF$_3$-4-NH$_2$ |
| F-549 | H | Et | H | 2-OEt-4-NH$_2$ |
| F-550 | Me | Me | H | 2-OEt-4-NH$_2$ |
| F-551 | Me | Et | H | 2-OEt-4-NH$_2$ |
| F-552 | Me | n-Pr | H | 2-OEt-4-NH$_2$ |
| F-553 | Me | i-Pr | H | 2-OEt-4-NH$_2$ |
| F-554 | Me | n-Bu | H | 2-OEt-4-NH$_2$ |
| F-555 | Et | Et | H | 2-OEt-4-NH$_2$ |
| F-556 | Et | n-Pr | H | 2-OEt-4-NH$_2$ |
| F-557 | Et | i-Pr | H | 2-OEt-4-NH$_2$ |
| F-558 | n-Pr | n-Pr | H | 2-OEt-4-NH$_2$ |
| F-559 | n-Pr | i-Pr | H | 2-OEt-4-NH$_2$ |
| F-560 | i-Pr | i-Pr | H | 2-OEt-4-NH$_2$ |

TABLE 36

| Compound No. | $R^{15}$ | $R^{16}$ | $R^{17}$ | $R^{18}$ |
|---|---|---|---|---|
| F-561 | H | Et | Me | 2-OEt-4-NH$_2$ |
| F-562 | Me | Me | Me | 2-OEt-4-NH$_2$ |
| F-563 | Me | Et | Me | 2-OEt-4-NH$_2$ |
| F-564 | Me | n-Pr | Me | 2-OEt-4-NH$_2$ |
| F-565 | Me | i-Pr | Me | 2-OEt-4-NH$_2$ |
| F-566 | Me | n-Bu | Me | 2-OEt-4-NH$_2$ |
| F-567 | Et | Et | Me | 2-OEt-4-NH$_2$ |
| F-568 | Et | n-Pr | Me | 2-OEt-4-NH$_2$ |
| F-569 | Et | i-Pr | Me | 2-OEt-4-NH$_2$ |
| F-570 | n-Pr | n-Pr | Me | 2-OEt-4-NH$_2$ |
| F-571 | n-Pr | i-Pr | Me | 2-OEt-4-NH$_2$ |
| F-572 | i-Pr | i-Pr | Me | 2-OEt-4-NH$_2$ |
| F-573 | H | Et | Et | 2-OEt-4-NH$_2$ |
| F-574 | Me | Me | Et | 2-OEt-4-NH$_2$ |
| F-575 | Me | Et | Et | 2-OEt-4-NH$_2$ |
| F-576 | Me | n-Pr | Et | 2-OEt-4-NH$_2$ |
| F-577 | Me | i-Pr | Et | 2-OEt-4-NH$_2$ |

TABLE 36-continued

| Compound No. | $R^{15}$ | $R^{16}$ | $R^{17}$ | $R^{18}$ |
|---|---|---|---|---|
| F-578 | Me | n-Bu | Et | 2-OEt-4-NH$_2$ |
| F-579 | Et | Et | Et | 2-OEt-4-NH$_2$ |
| F-580 | Et | n-Pr | Et | 2-OEt-4-NH$_2$ |
| F-581 | Et | i-Pr | Et | 2-OEt-4-NH$_2$ |
| F-582 | H | Et | H | 2-OCF$_3$-4-NH$_2$ |
| F-583 | Me | Me | H | 2-OCF$_3$-4-NH$_2$ |
| F-584 | Me | Et | H | 2-OCF$_3$-4-NH$_2$ |
| F-585 | Me | n-Pr | H | 2-OCF$_3$-4-NH$_2$ |
| F-586 | Me | i-Pr | H | 2-OCF$_3$-4-NH$_2$ |
| F-587 | Me | n-Bu | H | 2-OCF$_3$-4-NH$_2$ |
| F-588 | Et | Et | H | 2-OCF$_3$-4-NH$_2$ |
| F-589 | Et | n-Pr | H | 2-OCF$_3$-4-NH$_2$ |
| F-590 | Et | i-Pr | H | 2-OCF$_3$-4-NH$_2$ |
| F-591 | n-Pr | n-Pr | H | 2-OCF$_3$-4-NH$_2$ |
| F-592 | n-Pr | i-Pr | H | 2-OCF$_3$-4-NH$_2$ |
| F-593 | i-Pr | i-Pr | H | 2-OCF$_3$-4-NH$_2$ |
| F-594 | H | Et | Me | 2-OCF$_3$-4-NH$_2$ |
| F-595 | Me | Me | Me | 2-OCF$_3$-4-NH$_2$ |
| F-596 | Me | Et | Me | 2-OCF$_3$-4-NH$_2$ |
| F-597 | Me | n-Pr | Me | 2-OCF$_3$-4-NH$_2$ |
| F-598 | Me | i-Pr | Me | 2-OCF$_3$-4-NH$_2$ |
| F-599 | Me | n-Bu | Me | 2-OCF$_3$-4-NH$_2$ |
| F-600 | Et | Et | Me | 2-OCF$_3$-4-NH$_2$ |
| F-601 | Et | n-Pr | Me | 2-OCF$_3$-4-NH$_2$ |
| F-602 | Et | i-Pr | Me | 2-OCF$_3$-4-NH$_2$ |
| F-603 | n-Pr | n-Pr | Me | 2-OCF$_3$-4-NH$_2$ |
| F-604 | n-Pr | i-Pr | Me | 2-OCF$_3$-4-NH$_2$ |
| F-605 | i-Pr | i-Pr | Me | 2-OCF$_3$-4-NH$_2$ |
| F-606 | H | Et | Et | 2-OCF$_3$-4-NH$_2$ |
| F-607 | Me | Me | Et | 2-OCF$_3$-4-NH$_2$ |
| F-608 | Me | Et | Et | 2-OCF$_3$-4-NH$_2$ |
| F-609 | Me | n-Pr | Et | 2-OCF$_3$-4-NH$_2$ |
| F-610 | Me | i-Pr | Et | 2-OCF$_3$-4-NH$_2$ |
| F-611 | Me | n-Bu | Et | 2-OCF$_3$-4-NH$_2$ |
| F-612 | Et | Et | Et | 2-OCF$_3$-4-NH$_2$ |
| F-613 | Et | n-Pr | Et | 2-OCF$_3$-4-NH$_2$ |
| F-614 | Et | i-Pr | Et | 2-OCF$_3$-4-NH$_2$ |
| F-615 | H | Et | H | 2-Cl-4-NO$_2$ |
| F-616 | Me | Me | H | 2-Cl-4-NO$_2$ |
| F-617 | Me | Et | H | 2-Cl-4-NO$_2$ |
| F-618 | Me | n-Pr | H | 2-Cl-4-NO$_2$ |
| F-619 | Me | i-Pr | H | 2-Cl-4-NO$_2$ |
| F-620 | Me | n-Bu | H | 2-Cl-4-NO$_2$ |
| F-621 | Et | Et | H | 2-Cl-4-NO$_2$ |
| F-622 | Et | n-Pr | H | 2-Cl-4-NO$_2$ |
| F-623 | Et | i-Pr | H | 2-Cl-4-NO$_2$ |
| F-624 | n-Pr | n-Pr | H | 2-Cl-4-NO$_2$ |
| F-625 | n-Pr | i-Pr | H | 2-Cl-4-NO$_2$ |
| F-626 | i-Pr | i-Pr | H | 2-Cl-4-NO$_2$ |
| F-627 | H | Et | Me | 2-Cl-4-NO$_2$ |
| F-628 | Me | Me | Me | 2-Cl-4-NO$_2$ |
| F-629 | Me | Et | Me | 2-Cl-4-NO$_2$ |
| F-630 | Me | n-Pr | Me | 2-Cl-4-NO$_2$ |
| F-631 | Me | i-Pr | Me | 2-Cl-4-NO$_2$ |
| F-632 | Me | n-Bu | Me | 2-Cl-4-NO$_2$ |
| F-633 | Et | Et | Me | 2-Cl-4-NO$_2$ |
| F-634 | Et | n-Pr | Me | 2-Cl-4-NO$_2$ |
| F-635 | Et | i-Pr | Me | 2-Cl-4-NO$_2$ |
| F-636 | n-Pr | n-Pr | Me | 2-Cl-4-NO$_2$ |
| F-637 | n-Pr | i-Pr | Me | 2-Cl-4-NO$_2$ |
| F-638 | i-Pr | i-Pr | Me | 2-Cl-4-NO$_2$ |
| F-639 | H | Et | Et | 2-Cl-4-NO$_2$ |
| F-640 | Me | Me | Et | 2-Cl-4-NO$_2$ |

TABLE 37

| Compound No. | $R^{15}$ | $R^{16}$ | $R^{17}$ | $R^{18}$ |
|---|---|---|---|---|
| F-641 | Me | Et | Et | 2-Cl-4-NO$_2$ |
| F-642 | Me | n-Pr | Et | 2-Cl-4-NO$_2$ |
| F-643 | Me | i-Pr | Et | 2-Cl-4-NO$_2$ |
| F-644 | Me | n-Bu | Et | 2-Cl-4-NO$_2$ |

TABLE 37-continued

| Compound No. | $R^{15}$ | $R^{16}$ | $R^{17}$ | $R^{18}$ |
|---|---|---|---|---|
| F-645 | Et | Et | Et | 2-Cl-4-NO$_2$ |
| F-646 | Et | n-Pr | Et | 2-Cl-4-NO$_2$ |
| F-647 | Et | i-Pr | Et | 2-Cl-4-NO$_2$ |
| F-648 | H | Et | H | 2-Me-4-NO$_2$ |
| F-649 | Me | Me | H | 2-Me-4-NO$_2$ |
| F-650 | Me | Et | H | 2-Me-4-NO$_2$ |
| F-651 | Me | n-Pr | H | 2-Me-4-NO$_2$ |
| F-652 | Me | i-Pr | H | 2-Me-4-NO$_2$ |
| F-653 | Me | n-Bu | H | 2-Me-4-NO$_2$ |
| F-654 | Et | Et | H | 2-Me-4-NO$_2$ |
| F-655 | Et | n-Pr | H | 2-Me-4-NO$_2$ |
| F-656 | Et | i-Pr | H | 2-Me-4-NO$_2$ |
| F-657 | n-Pr | n-Pr | H | 2-Me-4-NO$_2$ |
| F-658 | n-Pr | i-Pr | H | 2-Me-4-NO$_2$ |
| F-659 | i-Pr | i-Pr | H | 2-Me-4-NO$_2$ |
| F-660 | H | Et | Me | 2-Me-4-NO$_2$ |
| F-661 | Me | Me | Me | 2-Me-4-NO$_2$ |
| F-662 | Me | Et | Me | 2-Me-4-NO$_2$ |
| F-663 | Me | n-Pr | Me | 2-Me-4-NO$_2$ |
| F-664 | Me | i-Pr | Me | 2-Me-4-NO$_2$ |
| F-665 | Me | n-Bu | Me | 2-Me-4-NO$_2$ |
| F-666 | Et | Et | Me | 2-Me-4-NO$_2$ |
| F-667 | Et | n-Pr | Me | 2-Me-4-NO$_2$ |
| F-668 | Et | i-Pr | Me | 2-Me-4-NO$_2$ |
| F-669 | n-Pr | n-Pr | Me | 2-Me-4-NO$_2$ |
| F-670 | n-Pr | i-Pr | Me | 2-Me-4-NO$_2$ |
| F-671 | i-Pr | i-Pr | Me | 2-Me-4-NO$_2$ |
| F-672 | H | Et | Et | 2-Me-4-NO$_2$ |
| F-673 | Me | Me | Et | 2-Me-4-NO$_2$ |
| F-674 | Me | Et | Et | 2-Me-4-NO$_2$ |
| F-675 | Me | n-Pr | Et | 2-Me-4-NO$_2$ |
| F-676 | Me | i-Pr | Et | 2-Me-4-NO$_2$ |
| F-677 | Me | n-Bu | Et | 2-Me-4-NO$_2$ |
| F-678 | Et | Et | Et | 2-Me-4-NO$_2$ |
| F-679 | Et | n-Pr | Et | 2-Me-4-NO$_2$ |
| F-680 | Et | i-Pr | Et | 2-Me-4-NO$_2$ |
| F-681 | H | Et | H | 2-OEt-4-NO$_2$ |
| F-682 | Me | Me | H | 2-OEt-4-NO$_2$ |
| F-683 | Me | Et | H | 2-OEt-4-NO$_2$ |
| F-684 | Me | n-Pr | H | 2-OEt-4-NO$_2$ |
| F-685 | Me | i-Pr | H | 2-OEt-4-NO$_2$ |
| F-686 | Me | n-Bu | H | 2-OEt-4-NO$_2$ |
| F-687 | Et | Et | H | 2-OEt-4-NO$_2$ |
| F-688 | Et | n-Pr | H | 2-OEt-4-NO$_2$ |
| F-689 | Et | i-Pr | H | 2-OEt-4-NO$_2$ |
| F-690 | n-Pr | n-Pr | H | 2-OEt-4-NO$_2$ |
| F-691 | n-Pr | i-Pr | H | 2-OEt-4-NO$_2$ |
| F-692 | i-Pr | i-Pr | H | 2-OEt-4-NO$_2$ |
| F-693 | H | Et | Me | 2-OEt-4-NO$_2$ |
| F-694 | Me | Me | Me | 2-OEt-4-NO$_2$ |
| F-695 | Me | Et | Me | 2-OEt-4-NO$_2$ |
| F-696 | Me | n-Pr | Me | 2-OEt-4-NO$_2$ |
| F-697 | Me | i-Pr | Me | 2-OEt-4-NO$_2$ |
| F-698 | Me | n-Bu | Me | 2-OEt-4-NO$_2$ |
| F-699 | Et | Et | Me | 2-OEt-4-NO$_2$ |
| F-700 | Et | n-Pr | Me | 2-OEt-4-NO$_2$ |
| F-701 | Et | i-Pr | Me | 2-OEt-4-NO$_2$ |
| F-702 | n-Pr | n-Pr | Me | 2-OEt-4-NO$_2$ |
| F-703 | n-Pr | i-Pr | Me | 2-OEt-4-NO$_2$ |
| F-704 | i-Pr | i-Pr | Me | 2-OEt-4-NO$_2$ |
| F-705 | H | Et | Et | 2-OEt-4-NO$_2$ |
| F-706 | Me | Me | Et | 2-OEt-4-NO$_2$ |
| F-707 | Me | Et | Et | 2-OEt-4-NO$_2$ |
| F-708 | Me | n-Pr | Et | 2-OEt-4-NO$_2$ |
| F-709 | Me | i-Pr | Et | 2-OEt-4-NO$_2$ |
| F-710 | Me | n-Bu | Et | 2-OEt-4-NO$_2$ |
| F-711 | Et | Et | Et | 2-OEt-4-NO$_2$ |
| F-712 | Et | n-Pr | Et | 2-OEt-4-NO$_2$ |
| F-713 | Et | i-Pr | Et | 2-OEt-4-NO$_2$ |
| F-714 | H | Et | H | 2-OCF$_3$-4-NO$_2$ |
| F-715 | Me | Me | H | 2-OCF$_3$-4-NO$_2$ |
| F-716 | Me | Et | H | 2-OCF$_3$-4-NO$_2$ |
| F-717 | Me | n-Pr | H | 2-OCF$_3$-4-NO$_2$ |
| F-718 | Me | i-Pr | H | 2-OCF$_3$-4-NO$_2$ |
| F-719 | Me | n-Bu | H | 2-OCF$_3$-4-NO$_2$ |
| F-720 | Et | Et | H | 2-OCF$_3$-4-NO$_2$ |

TABLE 38

| Compound No. | $R^{15}$ | $R^{16}$ | $R^{17}$ | $R^{18}$ |
|---|---|---|---|---|
| F-721 | Et | n-Pr | H | 2-OCF$_3$-4-NO$_2$ |
| F-722 | Et | i-Pr | H | 2-OCF$_3$-4-NO$_2$ |
| F-723 | n-Pr | n-Pr | H | 2-OCF$_3$-4-NO$_2$ |
| F-724 | n-Pr | i-Pr | H | 2-OCF$_3$-4-NO$_2$ |
| F-725 | i-Pr | i-Pr | H | 2-OCF$_3$-4-NO$_2$ |
| F-726 | H | Et | Me | 2-OCF$_3$-4-NO$_2$ |
| F-727 | Me | Me | Me | 2-OCF$_3$-4-NO$_2$ |
| F-728 | Me | Et | Me | 2-OCF$_3$-4-NO$_2$ |
| F-729 | Me | n-Pr | Me | 2-OCF$_3$-4-NO$_2$ |
| F-730 | Me | i-Pr | Me | 2-OCF$_3$-4-NO$_2$ |
| F-731 | Me | n-Bu | Me | 2-OCF$_3$-4-NO$_2$ |
| F-732 | Et | Et | Me | 2-OCF$_3$-4-NO$_2$ |
| F-733 | Et | n-Pr | Me | 2-OCF$_3$-4-NO$_2$ |
| F-734 | Et | i-Pr | Me | 2-OCF$_3$-4-NO$_2$ |
| F-735 | n-Pr | n-Pr | Me | 2-OCF$_3$-4-NO$_2$ |
| F-736 | n-Pr | i-Pr | Me | 2-OCF$_3$-4-NO$_2$ |
| F-737 | i-Pr | i-Pr | Me | 2-OCF$_3$-4-NO$_2$ |
| F-738 | H | Et | Et | 2-OCF$_3$-4-NO$_2$ |
| F-739 | Me | Me | Et | 2-OCF$_3$-4-NO$_2$ |
| F-740 | Me | Et | Et | 2-OCF$_3$-4-NO$_2$ |
| F-741 | Me | n-Pr | Et | 2-OCF$_3$-4-NO$_2$ |
| F-742 | Me | i-Pr | Et | 2-OCF$_3$-4-NO$_2$ |
| F-743 | Me | n-Bu | Et | 2-OCF$_3$-4-NO$_2$ |
| F-744 | Et | Et | Et | 2-OCF$_3$-4-NO$_2$ |
| F-745 | Et | n-Pr | Et | 2-OCF$_3$-4-NO$_2$ |
| F-746 | Et | i-Pr | Et | 2-OCF$_3$-4-NO$_2$ |
| F-747 | H | CH$_2$CF$_3$ | H | 4-NH$_2$ |
| F-748 | H | CH$_2$CF$_3$ | H | 4-NO$_2$ |
| F-749 | H | CH$_2$CF$_3$ | H | 2-OMe-4-NH$_2$ |
| F-750 | H | CH$_2$CF$_3$ | H | 2-OMe-4-NO$_2$ |
| F-751 | H | CH$_2$CF$_3$ | Me | 4-NH$_2$ |
| F-752 | H | CH$_2$CF$_3$ | Me | 4-NO$_2$ |
| F-753 | H | CH$_2$CF$_3$ | Me | 2-OMe-4-NH$_2$ |
| F-754 | H | CH$_2$CF$_3$ | Me | 2-OMe-4-NO$_2$ |
| F-755 | H | CH$_2$CF$_3$ | Et | 4-NH$_2$ |
| F-756 | H | CH$_2$CF$_3$ | Et | 4-NO$_2$ |
| F-757 | H | CH$_2$CF$_3$ | Et | 2-OMe-4-NH$_2$ |
| F-758 | H | CH$_2$CF$_3$ | Et | 2-OMe-4-NO$_2$ |
| F-759 | H | CH$_2$CH=CH$_2$ | H | 4-NH$_2$ |
| F-760 | H | CH$_2$CH=CH$_2$ | H | 4-NO$_2$ |
| F-761 | H | CH$_2$CH=CH$_2$ | H | 2-OMe-4-NH$_2$ |
| F-762 | H | CH$_2$CH=CH$_2$ | H | 2-OMe-4-NO$_2$ |
| F-763 | H | CH$_2$CH=CH$_2$ | Me | 4-NH$_2$ |
| F-764 | H | CH$_2$CH=CH$_2$ | Me | 4-NO$_2$ |
| F-765 | H | CH$_2$CH=CH$_2$ | Me | 2-OMe-4-NH$_2$ |
| F-766 | H | CH$_2$CH=CH$_2$ | Me | 2-OMe-4-NO$_2$ |
| F-767 | H | CH$_2$CH=CH$_2$ | Et | 4-NH$_2$ |
| F-768 | H | CH$_2$CH=CH$_2$ | Et | 4-NO$_2$ |
| F-769 | H | CH$_2$CH=CH$_2$ | Et | 2-OMe-4-NH$_2$ |
| F-770 | H | CH$_2$CH=CH$_2$ | Et | 2-OMe-4-NO$_2$ |
| F-771 | H | CH$_2$C≡CH | H | 4-NH$_2$ |
| F-772 | H | CH$_2$C≡CH | H | 4-NO$_2$ |
| F-773 | H | CH$_2$C≡CH | H | 2-OMe-4-NH$_2$ |
| F-774 | H | CH$_2$C≡CH | H | 2-OMe-4-NO$_2$ |
| F-775 | H | CH$_2$C≡CH | Me | 4-NH$_2$ |
| F-776 | H | CH$_2$C≡CH | Me | 4-NO$_2$ |
| F-777 | H | CH$_2$C≡CH | Me | 2-OMe-4-NH$_2$ |
| F-778 | H | CH$_2$C≡CH | Me | 2-OMe-4-NO$_2$ |
| F-779 | H | CH$_2$C≡CH | Et | 4-NH$_2$ |
| F-780 | H | CH$_2$C≡CH | Et | 4-NO$_2$ |
| F-781 | H | CH$_2$C≡CH | Et | 2-OMe-4-NH$_2$ |
| F-782 | H | CH$_2$C≡CH | Et | 2-OMe-4-NO$_2$ |
| F-783 | H | CH$_2$CH$_2$CF$_3$ | H | 4-NH$_2$ |
| F-784 | H | CH$_2$CH$_2$CF$_3$ | H | 4-NO$_2$ |
| F-785 | H | CH$_2$CH$_2$CF$_3$ | H | 2-OMe-4-NH$_2$ |
| F-786 | H | CH$_2$CH$_2$CF$_3$ | H | 2-OMe-4-NO$_2$ |

TABLE 38-continued

| Compound No. | $R^{15}$ | $R^{16}$ | $R^{17}$ | $R^{18}$ |
|---|---|---|---|---|
| F-787 | H | $CH_2CH_2CF_3$ | Me | 4-$NH_2$ |
| F-788 | H | $CH_2CH_2CF_3$ | Me | 4-$NO_2$ |
| F-789 | H | $CH_2CH_2CF_3$ | Me | 2-OMe-4-$NH_2$ |
| F-790 | H | $CH_2CH_2CF_3$ | Me | 2-OMe-4-$NO_2$ |
| F-791 | H | $CH_2CH_2CF_3$ | Et | 4-$NH_2$ |
| F-792 | H | $CH_2CH_2CF_3$ | Et | 4-$NO_2$ |
| F-793 | H | $CH_2CH_2CF_3$ | Et | 2-OMe-4-$NH_2$ |
| F-794 | H | $CH_2CH_2CF_3$ | Et | 2-OMe-4-$NO_2$ |
| F-795 | H | $CH_2CH=CHCH_3$ | H | 4-$NH_2$ |
| F-796 | H | $CH_2CH=CHCH_3$ | H | 4-$NO_2$ |
| F-797 | H | $CH_2CH=CHCH_3$ | H | 2-OMe-4-$NH_2$ |
| F-798 | H | $CH_2CH=CHCH_3$ | H | 2-OMe-4-$NO_2$ |
| F-799 | H | $CH_2CH=CHCH_3$ | Me | 4-$NH_2$ |
| F-800 | H | $CH_2CH=CHCH_3$ | Me | 4-$NO_2$ |

TABLE 39

| Compound No. | $R^{15}$ | $R^{16}$ | $R^{17}$ | $R^{18}$ |
|---|---|---|---|---|
| F-801 | H | $CH_2CH=CHCH_3$ | Me | 2-OMe-4-$NH_2$ |
| F-802 | H | $CH_2CH=CHCH_3$ | Me | 2-OMe-4-$NO_2$ |
| F-803 | H | $CH_2CH=CHCH_3$ | Et | 4-$NH_2$ |
| F-804 | H | $CH_2CH=CHCH_3$ | Et | 4-$NO_2$ |
| F-805 | H | $CH_2CH=CHCH_3$ | Et | 2-OMe-4-$NH_2$ |
| F-806 | H | $CH_2CH=CHCH_3$ | Et | 2-OMe-4-$NO_2$ |
| F-807 | H | $CH_2C\equiv CCH_3$ | H | 4-$NH_2$ |
| F-808 | H | $CH_2C\equiv CCH_3$ | H | 4-$NO_2$ |
| F-809 | H | $CH_2C\equiv CCH_3$ | H | 2-OMe-4-$NH_2$ |
| F-810 | H | $CH_2C\equiv CCH_3$ | H | 2-OMe-4-$NO_2$ |
| F-811 | H | $CH_2C\equiv CCH_3$ | Me | 4-$NH_2$ |
| F-812 | H | $CH_2C\equiv CCH_3$ | Me | 4-$NO_2$ |
| F-813 | H | $CH_2C\equiv CCH_3$ | Me | 2-OMe-4-$NH_2$ |
| F-814 | H | $CH_2C\equiv CCH_3$ | Me | 2-OMe-4-$NO_2$ |
| F-815 | H | $CH_2C\equiv CCH_3$ | Et | 4-$NH_2$ |
| F-816 | H | $CH_2C\equiv CCH_3$ | Et | 4-$NO_2$ |
| F-817 | H | $CH_2C\equiv CCH_3$ | Et | 2-OMe-4-$NH_2$ |
| F-818 | H | $CH_2C\equiv CCH_3$ | Et | 2-OMe-4-$NO_2$ |
| F-819 | Me | $CH_2CF_3$ | H | 4-$NH_2$ |
| F-820 | Me | $CH_2CF_3$ | H | 4-$NO_2$ |
| F-821 | Me | $CH_2CF_3$ | H | 4-OMe-4-$NH_2$ |
| F-822 | Me | $CH_2CF_3$ | H | 2-OMe-4-$NO_2$ |
| F-823 | Me | $CH_2CF_3$ | Me | 4-$NH_2$ |
| F-824 | Me | $CH_2CF_3$ | Me | 4-$NO_2$ |
| F-825 | Me | $CH_2CF_3$ | Me | 2-OMe-4-$NH_2$ |
| F-826 | Me | $CH_2CF_3$ | Me | 2-OMe-4-$NO_2$ |
| F-827 | Me | $CH_2CF_3$ | Et | 4-$NH_2$ |
| F-828 | Me | $CH_2CF_3$ | Et | 4-$NO_2$ |
| F-829 | Me | $CH_2CF_3$ | Et | 2-OMe-4-$NH_2$ |
| F-830 | Me | $CH_2CF_3$ | Et | 2-OMe-4-$NO_2$ |
| F-831 | Me | $CH_2CH=CH_2$ | H | 4-$NH_2$ |
| F-832 | Me | $CH_2CH=CH_2$ | H | 4-$NO_2$ |
| F-833 | Me | $CH_2CH=CH_2$ | H | 2-OMe-4-$NH_2$ |
| F-834 | Me | $CH_2CH=CH_2$ | H | 2-OMe-4-$NO_2$ |
| F-835 | Me | $CH_2CH=CH_2$ | Me | 4-$NH_2$ |
| F-836 | Me | $CH_2CH=CH_2$ | Me | 4-$NO_2$ |
| F-837 | Me | $CH_2CH=CH_2$ | Me | 2-OMe-4-$NH_2$ |
| F-838 | Me | $CH_2CH=CH_2$ | Me | 2-OMe-4-$NO_2$ |
| F-839 | Me | $CH_2CH=CH_2$ | Et | 4-$NH_2$ |
| F-840 | Me | $CH_2CH=CH_2$ | Et | 4-$NO_2$ |
| F-841 | Me | $CH_2CH=CH_2$ | Et | 2-OMe-4-$NH_2$ |
| F-842 | Me | $CH_2CH=CH_2$ | Et | 2-OMe-4-$NO_2$ |
| F-843 | Me | $CH_2C\equiv CH$ | H | 4-$NH_2$ |
| F-844 | Me | $CH_2C\equiv CH$ | H | 4-$NO_2$ |
| F-845 | Me | $CH_2C\equiv CH$ | H | 2-OMe-4-$NH_2$ |
| F-846 | Me | $CH_2C\equiv CH$ | H | 2-OMe-4-$NO_2$ |
| F-847 | Me | $CH_2C\equiv CH$ | Me | 4-$NH_2$ |
| F-848 | Me | $CH_2C\equiv CH$ | Me | 4-$NO_2$ |
| F-849 | Me | $CH_2C\equiv CH$ | Me | 2-OMe-4-$NH_2$ |
| F-850 | Me | $CH_2C\equiv CH$ | Me | 2-OMe-4-$NO_2$ |
| F-851 | Me | $CH_2C\equiv CH$ | Et | 4-$NH_2$ |
| F-852 | Me | $CH_2C\equiv CH$ | Et | 4-$NO_2$ |
| F-853 | Me | $CH_2C\equiv CH$ | Et | 2-OMe-4-$NH_2$ |

TABLE 39-continued

| Compound No. | $R^{15}$ | $R^{16}$ | $R^{17}$ | $R^{18}$ |
|---|---|---|---|---|
| F-854 | Me | $CH_2C\equiv CH$ | Et | 2-OMe-4-$NO_2$ |
| F-855 | Me | $CH_2CH_2CF_3$ | H | 4-$NH_2$ |
| F-856 | Me | $CH_2CH_2CF_3$ | H | 4-$NO_2$ |
| F-857 | Me | $CH_2CH_2CF_3$ | H | 2-OMe-4-$NH_2$ |
| F-858 | Me | $CH_2CH_2CF_3$ | H | 2-OMe-4-$NO_2$ |
| F-859 | Me | $CH_2CH_2CF_3$ | Me | 4-$NH_2$ |
| F-860 | Me | $CH_2CH_2CF_3$ | Me | 4-$NO_2$ |
| F-861 | Me | $CH_2CH_2CF_3$ | Me | 2-OMe-4-$NH_2$ |
| F-862 | Me | $CH_2CH_2CF_3$ | Me | 2-OMe-4-$NO_2$ |
| F-863 | Me | $CH_2CH_2CF_3$ | Et | 4-$NH_2$ |
| F-864 | Me | $CH_2CH_2CF_3$ | Et | 4-$NO_2$ |
| F-865 | Me | $CH_2CH_2CF_3$ | Et | 2-OMe-4-$NH_2$ |
| F-866 | Me | $CH_2CH_2CF_3$ | Et | 2-OMe-4-$NO_2$ |
| F-867 | Me | $CH_2CH=CHCH_3$ | H | 4-$NH_2$ |
| F-868 | Me | $CH_2CH=CHCH_3$ | H | 4-$NO_2$ |
| F-869 | Me | $CH_2CH=CHCH_3$ | H | 2-OMe-4-$NH_2$ |
| F-870 | Me | $CH_2CH=CHCH_3$ | H | 2-OMe-4-$NO_2$ |
| F-871 | Me | $CH_2CH=CHCH_3$ | Me | 4-$NH_2$ |
| F-872 | Me | $CH_2CH=CHCH_3$ | Me | 4-$NO_2$ |
| F-873 | Me | $CH_2CH=CHCH_3$ | Me | 2-OMe-4-$NH_2$ |
| F-874 | Me | $CH_2CH=CHCH_3$ | Me | 2-OMe-4-$NO_2$ |
| F-875 | Me | $CH_2CH=CHCH_3$ | Et | 4-$NH_2$ |
| F-876 | Me | $CH_2CH=CHCH_3$ | Et | 4-$NO_2$ |
| F-877 | Me | $CH_2CH=CHCH_3$ | Et | 2-OMe-4-$NH_2$ |
| F-878 | Me | $CH_2CH=CHCH_3$ | Et | 2-OMe-4-$NO_2$ |
| F-879 | Me | $CH_2C\equiv CCH_3$ | H | 4-$NH_2$ |
| F-880 | Me | $CH_2C\equiv CCH_3$ | H | 4-$NO_2$ |

TABLE 40

| Compound No. | $R^{15}$ | $R^{16}$ | $R^{17}$ | $R^{18}$ |
|---|---|---|---|---|
| F-881 | Me | $CH_2C\equiv CCH_3$ | H | 2-OMe-4-$NH_2$ |
| F-882 | Me | $CH_2C\equiv CCH_3$ | H | 2-OMe-4-$NO_2$ |
| F-883 | Me | $CH_2C\equiv CCH_3$ | Me | 4-$NH_2$ |
| F-884 | Me | $CH_2C\equiv CCH_3$ | Me | 4-$NO_2$ |
| F-885 | Me | $CH_2C\equiv CCH_3$ | Me | 2-OMe-4-$NH_2$ |
| F-886 | Me | $CH_2C\equiv CCH_3$ | Me | 2-OMe-4-$NO_2$ |
| F-887 | Me | $CH_2C\equiv CCH_3$ | Et | 4-$NH_2$ |
| F-888 | Me | $CH_2C\equiv CCH_3$ | Et | 4-$NO_2$ |
| F-889 | Me | $CH_2C\equiv CCH_3$ | Et | 2-OMe-4-$NH_2$ |
| F-890 | Me | $CH_2C\equiv CCH_3$ | Et | 2-OMe-4-$NO_2$ |
| F-891 | Et | $CH_2CF_3$ | H | 4-$NH_2$ |
| F-892 | Et | $CH_2CF_3$ | H | 4-$NO_2$ |
| F-893 | Et | $CH_2CF_3$ | H | 2-OMe-4-$NH_2$ |
| F-894 | Et | $CH_2CF_3$ | H | 2-OMe-4-$NO_2$ |
| F-895 | Et | $CH_2CF_3$ | Me | 4-$NH_2$ |
| F-896 | Et | $CH_2CF_3$ | Me | 4-$NO_2$ |
| F-897 | Et | $CH_2CF_3$ | Me | 2-OMe-4-$NH_2$ |
| F-898 | Et | $CH_2CF_3$ | Me | 2-OMe-4-$NO_2$ |
| F-899 | Et | $CH_2CF_3$ | Et | 4-$NH_2$ |
| F-900 | Et | $CH_2CF_3$ | Et | 4-$NO_2$ |
| F-901 | Et | $CH_2CF_3$ | Et | 2-OMe-4-$NH_2$ |
| F-902 | Et | $CH_2CF_3$ | Et | 2-OMe-4-$NO_2$ |
| F-903 | Et | $CH_2CH=CH_2$ | H | 4-$NH_2$ |
| F-904 | Et | $CH_2CH=CH_2$ | H | 4-$NO_2$ |
| F-905 | Et | $CH_2CH=CH_2$ | H | 2-OMe-4-$NH_2$ |
| F-906 | Et | $CH_2CH=CH_2$ | H | 2-OMe-4-$NO_2$ |
| F-907 | Et | $CH_2CH=CH_2$ | Me | 4-$NH_2$ |
| F-908 | Et | $CH_2CH=CH_2$ | Me | 4-$NO_2$ |
| F-909 | Et | $CH_2CH=CH_2$ | Me | 2-OMe-4-$NH_2$ |
| F-910 | Et | $CH_2CH=CH_2$ | Me | 2-OMe-4-$NO_2$ |
| F-911 | Et | $CH_2CH=CH_2$ | Et | 4-$NH_2$ |
| F-912 | Et | $CH_2CH=CH_2$ | Et | 4-$NO_2$ |
| F-913 | Et | $CH_2CH=CH_2$ | Et | 2-OMe-4-$NH_2$ |
| F-914 | Et | $CH_2CH=CH_2$ | Et | 2-OMe-4-$NO_2$ |
| F-915 | Et | $CH_2C\equiv CH$ | H | 4-$NH_2$ |
| F-916 | Et | $CH_2C\equiv CH$ | H | 4-$NO_2$ |
| F-917 | Et | $CH_2C\equiv CH$ | H | 2-OMe-4-$NH_2$ |
| F-918 | Et | $CH_2C\equiv CH$ | H | 2-OMe-4-$NO_2$ |
| F-919 | Et | $CH_2C\equiv CH$ | Me | 4-$NH_2$ |
| F-920 | Et | $CH_2C\equiv CH$ | Me | 4-$NO_2$ |

TABLE 40-continued

| Compound No. | R15 | R16 | R17 | R18 |
|---|---|---|---|---|
| F-921 | Et | CH₂C≡CH | Me | 2-OMe-4-NH₂ |
| F-922 | Et | CH₂C≡CH | Me | 2-OMe-4-NO₂ |
| F-923 | Et | CH₂C≡CH | Et | 4-NH₂ |
| F-924 | Et | CH₂C≡CH | Et | 4-NO₂ |
| F-925 | Et | CH₂C≡CH | Et | 2-OMe-4-NH₂ |
| F-926 | Et | CH₂C≡CH | Et | 2-OMe-4-NO₂ |
| F-927 | Et | CH₂CH₂CF₃ | H | 4-NH₂ |
| F-928 | Et | CH₂CH₂CF₃ | H | 4-NO₂ |
| F-929 | Et | CH₂CH₂CF₃ | H | 2-OMe-4-NH₂ |
| F-930 | Et | CH₂CH₂CF₃ | H | 2-OMe-4-NO₂ |
| F-931 | Et | CH₂CH₂CF₃ | Me | 4-NH₂ |
| F-932 | Et | CH₂CH₂CF₃ | Me | 4-NO₂ |
| F-933 | Et | CH₂CH₂CF₃ | Me | 2-OMe-4-NH₂ |
| F-934 | Et | CH₂CH₂CF₃ | Me | 2-OMe-4-NO₂ |
| F-935 | Et | CH₂CH₂CF₃ | Et | 4-NH₂ |
| F-936 | Et | CH₂CH₂CF₃ | Et | 4-NO₂ |
| F-937 | Et | CH₂CH₂CF₃ | Et | 2-OMe-4-NH₂ |
| F-938 | Et | CH₂CH₂CF₃ | Et | 2-OMe-4-NO₂ |
| F-939 | Et | CH₂CH=CHCH₃ | H | 4-NH₂ |
| F-940 | Et | CH₂CH=CHCH₃ | H | 4-NO₂ |
| F-941 | Et | CH₂CH=CHCH₃ | H | 2-OMe-4-NH₂ |
| F-942 | Et | CH₂CH=CHCH₃ | H | 2-OMe-4-NO₂ |
| F-943 | Et | CH₂CH=CHCH₃ | Me | 4-NH₂ |
| F-944 | Et | CH₂CH=CHCH₃ | Me | 4-NO₂ |
| F-945 | Et | CH₂CH=CHCH₃ | Me | 2-OMe-4-NH₂ |
| F-946 | Et | CH₂CH=CHCH₃ | Me | 2-OMe-4-NO₂ |
| F-947 | Et | CH₂CH=CHCH₃ | Et | 4-NH₂ |
| F-948 | Et | CH₂CH=CHCH₃ | Et | 4-NO₂ |
| F-949 | Et | CH₂CH=CHCH₃ | Et | 2-OMe-4-NH₂ |
| F-950 | Et | CH₂CH=CHCH₃ | Et | 2-OMe-4-NO₂ |
| F-951 | Et | CH₂C≡CCH₃ | H | 4-NH₂ |
| F-952 | Et | CH₂C≡CCH₃ | H | 4-NO₂ |
| F-953 | Et | CH₂C≡CCH₃ | H | 2-OMe-4-NH₂ |
| F-954 | Et | CH₂C≡CCH₃ | H | 2-OMe-4-NO₂ |
| F-955 | Et | CH₂C≡CCH₃ | Me | 4-NH₂ |
| F-956 | Et | CH₂C≡CCH₃ | Me | 4-NO₂ |
| F-957 | Et | CH₂C≡CCH₃ | Me | 2-OMe-4-NH₂ |
| F-958 | Et | CH₂C≡CCH₃ | Me | 2-OMe-4-NO₂ |
| F-959 | Et | CH₂C≡CCH₃ | Et | 4-NH₂ |
| F-960 | Et | CH₂C≡CCH₃ | Et | 4-NO₂ |

TABLE 41

| Compound No. | R15 | R16 | R17 | R18 |
|---|---|---|---|---|
| F-961 | Et | CH₂C≡CCH₃ | Et | 2-OMe-4-NH₂ |
| F-962 | Et | CH₂C≡CCH₃ | Et | 2-OMe-4-NO₂ |
| F-963 | n-Pr | CH₂CF₃ | H | 4-NH₂ |
| F-964 | n-Pr | CH₂CF₃ | H | 4-NO₂ |
| F-965 | n-Pr | CH₂CF₃ | H | 2-OMe-4-NH₂ |
| F-966 | n-Pr | CH₂CF₃ | H | 2-OMe-4-NO₂ |
| F-967 | n-Pr | CH₂CF₃ | Me | 4-NH₂ |
| F-968 | n-Pr | CH₂CF₃ | Me | 4-NO₂ |
| F-969 | n-Pr | CH₂CF₃ | Me | 2-OMe-4-NH₂ |
| F-970 | n-Pr | CH₂CF₃ | Me | 2-OMe-4-NO₂ |
| F-971 | n-Pr | CH₂CF₃ | Et | 4-NH₂ |
| F-972 | n-Pr | CH₂CF₃ | Et | 4-NO₂ |
| F-973 | n-Pr | CH₂CF₃ | Et | 2-OMe-4-NH₂ |
| F-974 | n-Pr | CH₂CF₃ | Et | 2-OMe-4-NO₂ |
| F-975 | n-Pr | CH₂CH=CH₂ | H | 4-NH₂ |
| F-976 | n-Pr | CH₂CH=CH₂ | H | 4-NO₂ |
| F-977 | n-Pr | CH₂CH=CH₂ | H | 2-OMe-4-NH₂ |
| F-978 | n-Pr | CH₂CH=CH₂ | H | 2-OMe-4-NO₂ |
| F-979 | n-Pr | CH₂CH=CH₂ | Me | 4-NH₂ |
| F-980 | n-Pr | CH₂CH=CH₂ | Me | 4-NO₂ |
| F-981 | n-Pr | CH₂CH=CH₂ | Me | 2-OMe-4-NH₂ |
| F-982 | n-Pr | CH₂CH=CH₂ | Me | 2-OMe-4-NO₂ |
| F-983 | n-Pr | CH₂CH=CH₂ | Et | 4-NH₂ |
| F-984 | n-Pr | CH₂CH=CH₂ | Et | 4-NO₂ |
| F-985 | n-Pr | CH₂CH=CH₂ | Et | 2-OMe-4-NH₂ |
| F-986 | n-Pr | CH₂CH=CH₂ | Et | 2-OMe-4-NO₂ |
| F-987 | n-Pr | CH₂C≡CH | H | 4-NH₂ |

TABLE 41-continued

| Compound No. | R15 | R16 | R17 | R18 |
|---|---|---|---|---|
| F-988 | n-Pr | CH₂C≡CH | H | 4-NO₂ |
| F-989 | n-Pr | CH₂C≡CH | H | 2-OMe-4-NH₂ |
| F-990 | n-Pr | CH₂C≡CH | H | 2-OMe-4-NO₂ |
| F-991 | n-Pr | CH₂C≡CH | Me | 4-NH₂ |
| F-992 | n-Pr | CH₂C≡CH | Me | 4-NO₂ |
| F-993 | n-Pr | CH₂C≡CH | Me | 2-OMe-4-NH₂ |
| F-994 | n-Pr | CH₂C≡CH | Me | 2-OMe-4-NO₂ |
| F-995 | n-Pr | CH₂C≡CH | Et | 4-NH₂ |
| F-996 | n-Pr | CH₂C≡CH | Et | 4-NO₂ |
| F-997 | n-Pr | CH₂C≡CH | Et | 2-OMe-4-NH₂ |
| F-998 | n-Pr | CH₂C≡CH | Et | 2-OMe-4-NO₂ |
| F-999 | n-Pr | CH₂CH₂CF₃ | H | 4-NH₂ |
| F-1000 | n-Pr | CH₂CH₂CF₃ | H | 4-NO₂ |
| F-1001 | n-Pr | CH₂CH₂CF₃ | H | 2-OMe-4-NH₂ |
| F-1002 | n-Pr | CH₂CH₂CF₃ | H | 2-OMe-4-NO₂ |
| F-1003 | n-Pr | CH₂CH₂CF₃ | Me | 4-NH₂ |
| F-1004 | n-Pr | CH₂CH₂CF₃ | Me | 4-NO₂ |
| F-1005 | n-Pr | CH₂CH₂CF₃ | Me | 2-OMe-4-NH₂ |
| F-1006 | n-Pr | CH₂CH₂CF₃ | Me | 2-OMe-4-NO₂ |
| F-1007 | n-Pr | CH₂CH₂CF₃ | Et | 4-NH₂ |
| F-1008 | n-Pr | CH₂CH₂CF₃ | Et | 4-NO₂ |
| F-1009 | n-Pr | CH₂CH₂CF₃ | Et | 2-OMe-4-NH₂ |
| F-1010 | n-Pr | CH₂CH₂CF₃ | Et | 2-OMe-4-NO₂ |
| F-1011 | n-Pr | CH₂CH=CHCH₃ | H | 4-NH₂ |
| F-1012 | n-Pr | CH₂CH=CHCH₃ | H | 4-NO₂ |
| F-1013 | n-Pr | CH₂CH=CHCH₃ | H | 2-OMe-4-NH₂ |
| F-1014 | n-Pr | CH₂CH=CHCH₃ | H | 2-OMe-4-NO₂ |
| F-1015 | n-Pr | CH₂CH=CHCH₃ | Me | 4-NH₂ |
| F-1016 | n-Pr | CH₂CH=CHCH₃ | Me | 4-NO₂ |
| F-1017 | n-Pr | CH₂CH=CHCH₃ | Me | 2-OMe-4-NH₂ |
| F-1018 | n-Pr | CH₂CH=CHCH₃ | Me | 2-OMe-4-NO₂ |
| F-1019 | n-Pr | CH₂CH=CHCH₃ | Et | 4-NH₂ |
| F-1020 | n-Pr | CH₂CH=CHCH₃ | Et | 4-NO₂ |
| F-1021 | n-Pr | CH₂CH=CHCH₃ | Et | 2-OMe-4-NH₂ |
| F-1022 | n-Pr | CH₂CH=CHCH₃ | Et | 2-OMe-4-NO₂ |
| F-1023 | n-Pr | CH₂C≡CCH₃ | H | 4-NH₂ |
| F-1024 | n-Pr | CH₂C≡CCH₃ | H | 4-NO₂ |
| F-1025 | n-Pr | CH₂C≡CCH₃ | H | 2-OMe-4-NH₂ |
| F-1026 | n-Pr | CH₂C≡CCH₃ | H | 2-OMe-4-NO₂ |
| F-1027 | n-Pr | CH₂C≡CCH₃ | Me | 4-NH₂ |
| F-1028 | n-Pr | CH₂C≡CCH₃ | Me | 4-NO₂ |
| F-1029 | n-Pr | CH₂C≡CCH₃ | Me | 2-OMe-4-NH₂ |
| F-1030 | n-Pr | CH₂C≡CCH₃ | Me | 2-OMe-4-NO₂ |
| F-1031 | n-Pr | CH₂C≡CCH₃ | Et | 4-NH₂ |
| F-1032 | n-Pr | CH₂C≡CCH₃ | Et | 4-NO₂ |
| F-1033 | n-Pr | CH₂C≡CCH₃ | Et | 2-OMe-4-NH₂ |
| F-1034 | n-Pr | CH₂C≡CCH₃ | Et | 2-OMe-4-NO₂ |
| F-1035 | i-Pr | CH₂CF₃ | H | 4-NH₂ |
| F-1036 | i-Pr | CH₂CF₃ | H | 4-NO₂ |
| F-1037 | i-Pr | CH₂CF₃ | H | 2-OMe-4-NH₂ |
| F-1038 | i-Pr | CH₂CF₃ | H | 2-OMe-4-NO₂ |
| F-1039 | i-Pr | CH₂CF₃ | Me | 4-NH₂ |
| F-1040 | i-Pr | CH₂CF₃ | Me | 4-NO₂ |

TABLE 42

| Compound No. | R15 | R16 | R17 | R18 |
|---|---|---|---|---|
| F-1041 | i-Pr | CH₂CF₃ | Me | 2-OMe-4-NH₂ |
| F-1042 | i-Pr | CH₂CF₃ | Me | 2-OMe-4-NO₂ |
| F-1043 | i-Pr | CH₂CF₃ | Et | 4-NH₂ |
| F-1044 | i-Pr | CH₂CF₃ | Et | 4-NO₂ |
| F-1045 | i-Pr | CH₂CF₃ | Et | 2-OMe-4-NH₂ |
| F-1046 | i-Pr | CH₂CF₃ | Et | 2-OMe-4-NO₂ |
| F-1047 | i-Pr | CH₂CH=CH₂ | H | 4-NH₂ |
| F-1048 | i-Pr | CH₂CH=CH₂ | H | 4-NO₂ |
| F-1049 | i-Pr | CH₂CH=CH₂ | H | 2-OMe-4-NH₂ |
| F-1050 | i-Pr | CH₂CH=CH₂ | H | 2-OMe-4-NO₂ |
| F-1051 | i-Pr | CH₂CH=CH₂ | Me | 4-NH₂ |
| F-1052 | i-Pr | CH₂CH=CH₂ | Me | 4-NO₂ |
| F-1053 | i-Pr | CH₂CH=CH₂ | Me | 2-OMe-4-NH₂ |
| F-1054 | i-Pr | CH₂CH=CH₂ | Me | 2-OMe-4-NO₂ |

TABLE 42-continued

| Compound No. | $R^{15}$ | $R^{16}$ | $R^{17}$ | $R^{18}$ |
|---|---|---|---|---|
| F-1055 | i-Pr | $CH_2CH=CH_2$ | Et | 4-$NH_2$ |
| F-1056 | i-Pr | $CH_2CH=CH_2$ | Et | 4-$NO_2$ |
| F-1057 | i-Pr | $CH_2CH=CH_2$ | Et | 2-OMe-4-$NH_2$ |
| F-1058 | i-Pr | $CH_2CH=CH_2$ | Et | 2-OMe-4-$NO_2$ |
| F-1059 | i-Pr | $CH_2C\equiv CH$ | H | 4-$NH_2$ |
| F-1060 | i-Pr | $CH_2C\equiv CH$ | H | 4-$NO_2$ |
| F-1061 | i-Pr | $CH_2C\equiv CH$ | H | 2-OMe-4-$NH_2$ |
| F-1062 | i-Pr | $CH_2C\equiv CH$ | H | 2-OMe-4-$NO_2$ |
| F-1063 | i-Pr | $CH_2C\equiv CH$ | Me | 4-$NH_2$ |
| F-1064 | i-Pr | $CH_2C\equiv CH$ | Me | 4-$NO_2$ |
| F-1065 | i-Pr | $CH_2C\equiv CH$ | Me | 2-OMe-4-$NH_2$ |
| F-1066 | i-Pr | $CH_2C\equiv CH$ | Me | 2-OMe-4-$NO_2$ |
| F-1067 | i-Pr | $CH_2C\equiv CH$ | Et | 4-$NH_2$ |
| F-1068 | i-Pr | $CH_2C\equiv CH$ | Et | 4-$NO_2$ |
| F-1069 | i-Pr | $CH_2C\equiv CH$ | Et | 2-OMe-4-$NH_2$ |
| F-1070 | i-Pr | $CH_2C\equiv CH$ | Et | 2-OMe-4-$NO_2$ |
| F-1071 | i-Pr | $CH_2CH_2CF_3$ | H | 4-$NH_2$ |
| F-1072 | i-Pr | $CH_2CH_2CF_3$ | H | 4-$NO_2$ |
| F-1073 | i-Pr | $CH_2CH_2CF_3$ | H | 2-OMe-4-$NH_2$ |
| F-1074 | i-Pr | $CH_2CH_2CF_3$ | H | 2-OMe-4-$NO_2$ |
| F-1075 | i-Pr | $CH_2CH_2CF_3$ | Me | 4-$NH_2$ |
| F-1076 | i-Pr | $CH_2CH_2CF_3$ | Me | 4-$NO_2$ |
| F-1077 | i-Pr | $CH_2CH_2CF_3$ | Me | 2-OMe-4-$NH_2$ |
| F-1078 | i-Pr | $CH_2CH_2CF_3$ | Me | 2-OMe-4-$NO_2$ |
| F-1079 | i-Pr | $CH_2CH_2CF_3$ | Et | 4-$NH_2$ |
| F-1080 | i-Pr | $CH_2CH_2CF_3$ | Et | 4-$NO_2$ |
| F-1081 | i-Pr | $CH_2CH_2CF_3$ | Et | 2-OMe-4-$NH_2$ |
| F-1082 | i-Pr | $CH_2CH_2CF_3$ | Et | 2-OMe-4-$NO_2$ |
| F-1083 | i-Pr | $CH_2CH=CHCH_3$ | H | 4-$NH_2$ |
| F-1084 | i-Pr | $CH_2CH=CHCH_3$ | H | 4-$NO_2$ |
| F-1085 | i-Pr | $CH_2CH=CHCH_3$ | H | 2-OMe-4-$NH_2$ |
| F-1086 | i-Pr | $CH_2CH=CHCH_3$ | H | 2-OMe-4-$NO_2$ |
| F-1087 | i-Pr | $CH_2CH=CHCH_3$ | Me | 4-$NH_2$ |
| F-1088 | i-Pr | $CH_2CH=CHCH_3$ | Me | 4-$NO_2$ |
| F-1089 | i-Pr | $CH_2CH=CHCH_3$ | Me | 2-OMe-4-$NH_2$ |
| F-1090 | i-Pr | $CH_2CH=CHCH_3$ | Me | 2-OMe-4-$NO_2$ |
| F-1091 | i-Pr | $CH_2CH=CHCH_3$ | Et | 4-$NH_2$ |
| F-1092 | i-Pr | $CH_2CH=CHCH_3$ | Et | 4-$NO_2$ |
| F-1093 | i-Pr | $CH_2CH=CHCH_3$ | Et | 2-OMe-4-$NH_2$ |
| F-1094 | i-Pr | $CH_2CH=CHCH_3$ | Et | 2-OMe-4-$NO_2$ |
| F-1095 | i-Pr | $CH_2C\equiv CCH_3$ | H | 4-$NH_2$ |
| F-1096 | i-Pr | $CH_2C\equiv CCH_3$ | H | 4-$NO_2$ |
| F-1097 | i-Pr | $CH_2C\equiv CCH_3$ | H | 2-OMe-4-$NH_2$ |
| F-1098 | i-Pr | $CH_2C\equiv CCH_3$ | H | 2-OMe-4-$NO_2$ |
| F-1099 | i-Pr | $CH_2C\equiv CCH_3$ | Me | 4-$NH_2$ |
| F-1100 | i-Pr | $CH_2C\equiv CCH_3$ | Me | 4-$NO_2$ |
| F-1101 | i-Pr | $CH_2C\equiv CCH_3$ | Me | 2-OMe-4-$NH_2$ |
| F-1102 | i-Pr | $CH_2C\equiv CCH_3$ | Me | 2-OMe-4-$NO_2$ |
| F-1103 | i-Pr | $CH_2C\equiv CCH_3$ | Et | 4-$NH_2$ |
| F-1104 | i-Pr | $CH_2C\equiv CCH_3$ | Et | 4-$NO_2$ |
| F-1105 | i-Pr | $CH_2C\equiv CCH_3$ | Et | 2-OMe-4-$NH_2$ |
| F-1106 | i-Pr | $CH_2C\equiv CCH_3$ | Et | 2-OMe-4-$NO_2$ |

TABLE 43

| Compound No. | $R^{15}$ | $R^{16}$ | $R^{17}$ | $R^{18}$ |
|---|---|---|---|---|
| F-1107 | $CH_2CF_3$ | $CH_2CF_3$ | H | 4-$NH_2$ |
| F-1108 | $CH_2CF_3$ | $CH_2CF_3$ | H | 4-$NO_2$ |
| F-1109 | $CH_2CF_3$ | $CH_2CF_3$ | H | 2-OMe-4-$NH_2$ |
| F-1110 | $CH_2CF_3$ | $CH_2CF_3$ | H | 2-OMe-4-$NO_2$ |
| F-1111 | $CH_2CF_3$ | $CH_2CF_3$ | Me | 4-$NH_2$ |
| F-1112 | $CH_2CF_3$ | $CH_2CF_3$ | Me | 4-$NO_2$ |
| F-1113 | $CH_2CF_3$ | $CH_2CF_3$ | Me | 2-OMe-4-$NH_2$ |
| F-1114 | $CH_2CF_3$ | $CH_2CF_3$ | Me | 2-OMe-4-$NO_2$ |
| F-1115 | $CH_2CF_3$ | $CH_2CF_3$ | Et | 4-$NH_2$ |
| F-1116 | $CH_2CF_3$ | $CH_2CF_3$ | Et | 4-$NO_2$ |
| F-1117 | $CH_2CF_3$ | $CH_2CF_3$ | Et | 2-OMe-4-$NH_2$ |
| F-1118 | $CH_2CF_3$ | $CH_2CF_3$ | Et | 2-OMe-4-$NO_2$ |
| F-1119 | $CH_2CH=CH_2$ | $CH_2CH=CH_2$ | H | 4-$NH_2$ |
| F-1120 | $CH_2CH=CH_2$ | $CH_2CH=CH_2$ | H | 4-$NO_2$ |
| F-1121 | $CH_2CH=CH_2$ | $CH_2CH=CH_2$ | H | 2-OMe-4-$NH_2$ |
| F-1122 | $CH_2CH=CH_2$ | $CH_2CH=CH_2$ | H | 2-OMe-4-$NO_2$ |
| F-1123 | $CH_2CH=CH_2$ | $CH_2CH=CH_2$ | Me | 4-$NH_2$ |
| F-1124 | $CH_2CH=CH_2$ | $CH_2CH=CH_2$ | Me | 4-$NO_2$ |
| F-1125 | $CH_2CH=CH_2$ | $CH_2CH=CH_2$ | Me | 2-OMe-4-$NH_2$ |
| F-1126 | $CH_2CH=CH_2$ | $CH_2CH=CH_2$ | Me | 2-OMe-4-$NO_2$ |
| F-1127 | $CH_2CH=CH_2$ | $CH_2CH=CH_2$ | Et | 4-$NH_2$ |
| F-1128 | $CH_2CH=CH_2$ | $CH_2CH=CH_2$ | Et | 4-$NO_2$ |
| F-1129 | $CH_2CH=CH_2$ | $CH_2CH=CH_2$ | Et | 2-OMe-4-$NH_2$ |
| F-1130 | $CH_2CH=CH_2$ | $CH_2CH=CH_2$ | Et | 2-OMe-4-$NO_2$ |
| F-1131 | $CH_2C\equiv CH$ | $CH_2C\equiv CH$ | H | 4-$NH_2$ |
| F-1132 | $CH_2C\equiv CH$ | $CH_2C\equiv CH$ | H | 4-$NO_2$ |
| F-1133 | $CH_2C\equiv CH$ | $CH_2C\equiv CH$ | H | 2-OMe-4-$NH_2$ |
| F-1134 | $CH_2C\equiv CH$ | $CH_2C\equiv CH$ | H | 2-OMe-4-$NO_2$ |
| F-1135 | $CH_2C\equiv CH$ | $CH_2C\equiv CH$ | Me | 4-$NH_2$ |
| F-1136 | $CH_2C\equiv CH$ | $CH_2C\equiv CH$ | Me | 4-$NO_2$ |
| F-1137 | $CH_2C\equiv CH$ | $CH_2C\equiv CH$ | Me | 2-OMe-4-$NH_2$ |
| F-1138 | $CH_2C\equiv CH$ | $CH_2C\equiv CH$ | Me | 2-OMe-4-$NO_2$ |
| F-1139 | $CH_2C\equiv CH$ | $CH_2C\equiv CH$ | Et | 4-$NH_2$ |
| F-1140 | $CH_2C\equiv CH$ | $CH_2C\equiv CH$ | Et | 4-$NO_2$ |
| F-1141 | $CH_2C\equiv CH$ | $CH_2C\equiv CH$ | Et | 2-OMe-4-$NH_2$ |
| F-1142 | $CH_2C\equiv CH$ | $CH_2C\equiv CH$ | Et | 2-OMe-4-$NO_2$ |

Test Example 1 Inhibitory Effect Against Cellular Signaling Derived From Ras Oncogene Products 1) Establishment of Cell Lines Used in Assay Based on the reporter plasmid (pGV-P (Toyo Ink, Japan)), in which luciferase gene was ligated to SV40-derived minimal promoter, we constructed a plasmid designated pRRE3-luc by inserting 3 copies of chemically synthesized oligonucleotides (Sequence: CAGGATATGACTCT, derived from mouse NVL-3 (M. A. Reddy et al.(1992)Mol. Endocrinol., 6, 1051)) into upstream of the promoter. v-ki-ras-transformed NIH3T3 cells (DT cells, provided by Dr. Makoto Noda (Kyoto Univ., School of medicine)) were transfected with this plasmid by liposome-mediated transfection and transfected cell lines stably incorporated and maintained each plasmid were obtained. We named pGV-P and pRRE3-transfected cell line as DT-C and DT-R, respectively and used in the assay described below.

2) Preparation of Samples i) All the cell lines were cultured in Dulbecco's Modified Essential Medium (DMEM: 10% Fetal Calf Serum (FCS: Hyclone, USA)) including 60 mg/ml kanamycin (Meiji Seika, Japan) in humidified incubator under condition of 5% $CO_2$ at 37° C.

ii) DT-C and DT-R cells were seeded at 2500 cells/well into flat-bottom 96 well multiplate (Sumitomo bakelite) and incubated for 24 hours.

iii) Test compounds were prepared as 1 mg/ml DMSO solution.

iv) The solution of test compounds were added to the culture. Tested compounds are used at the concentration from 10 mg/ml to 0.51 ng/ml with by 3-fold dilution.

v) After 24 hours, the culture supernatant was completely aspirated and 20 ml of cell-lysing solution (PGC-50 (Toyo Ink, Japan)) was added before cells were dried up. In order to the cells were lysed completely, multi-well plates were left at room temperature for 10 to 30 min. The plates were wrapped up and stored at −20° C. till the day of measurement.

3) Measurement of Samples i) Melt the samples by putting 96 well multiplate at 37° C. and add 90 μl/well 25 mM Tris (pH 7.5).

ii) Transfer 50 μl of the sample (110 μl) to the 96 well microplate for measurement (Microlite 1 (Dynatech)).

iii) Measure the samples by the luminometer, LUMINOUS CT9000D (Dia-Yatron, Japan). We used Pickagene luminescence kit PGL2000 or LT2.0 (Toyo Ink, Japan) as substrates for luminescence measurement (50 μl/well).

4) Judgment of the Results i) The luciferase activity of DT-C cells and DT-R cells were plotted in the graph where the relative activity and the compound concentration were expressed as Y-axis and X-axis, respectively. We judged by the degree of dissociation between the activities of DT-C cells and DT-R cells as an index.

ii) Concretely, efficacy of the compound was expressed by two values described below.

a) Among the points of concentration tested, the minimal concentration (Minimal Active Concentration: MAC), at which the activities of DT-C cells and DT-R cells dissociated, was shown as an index of efficacy of the compound. The MAC value was not indicated about the compound which did not show dissociation of both activities in this assay (negative).

b) Among the points of concentration tested, the concentration which is the nearest to 50% inhibition concentration at DT-C cells (IC50-C), was shown as an index of non-specific transcription-inhibitory effect or of cytotoxicity. In case of positive compounds, 50% inhibition concentration above the area of active concentration in DT-C cells was expressed as $IC_{50}$-C.

The results of the assay were shown in tables 44 and 45.

TABLE 44

| Compound No. | MAC (μg/ml) | $IC_{50}$-C (μg/ml) |
|---|---|---|
| A-1 | 0.0412 | 10 |
| A-2 | 0.0412 | 10 |
| A-3 | 0.0412 | 10 |
| A-23 | 0.123 | 10 |
| A-24 | 0.0137 | 3.33 |
| A-25 | 0.370 | 10 |
| A-26 | 0.370 | >10 |
| A-33 | 0.0137 | >10 |
| A-36 | 0.0412 | 3.33 |
| A-37 | 0.0412 | 3.33 |
| A-38 | 0.0412 | 10 |
| A-40 | 0.370 | 10 |
| A-42 | 0.0137 | >10 |
| A-44 | <0.000508 | 3.33 |
| A-49 | <0.000508 | 3.33 |
| A-51 | 0.123 | 3.33 |
| A-52 | 0.123 | 10 |
| A-57 | 0.0137 | 10 |
| A-60 | <0.000508 | >10 |
| A-61 | <0.000508 | >10 |
| A-62 | 0.0412 | 10 |
| A-63 | 0.0412 | 3.33 |
| A-64 | 0.370 | 10 |
| A-65 | <0.000508 | 10 |
| A-70 | 0.123 | 10 |
| A-71 | 1.11 | 10 |
| A-73 | 0.123 | >10 |
| A-74 | 0.123 | 10 |
| A-75 | <0.000508 | >10 |
| A-76 | 0.0137 | 10 |
| A-80 | 0.370 | 3.33 |
| A-81 | 0.0412 | >10 |
| A-82 | <0.000508 | 10 |
| A-88 | 0.123 | >10 |
| A-89 | 0.123 | >10 |

TABLE 44-continued

| Compound No. | MAC (μg/ml) | $IC_{50}$-C (μg/ml) |
|---|---|---|
| A-96 | 0.370 | >10 |
| A-106 | 0.370 | >10 |
| A-107 | 0.370 | 10 |
| A-108 | 0.123 | >10 |
| A-110 | 0.123 | >10 |
| A-111 | 0.123 | 10 |
| A-112 | 1.11 | >10 |
| A-114 | 1.11 | 10 |
| A-119 | 0.37 | >10 |
| A-120 | 0.123 | 10 |
| A-121 | <0.000508 | >10 |
| A-122 | 1.11 | 10 |
| A-123 | 1.11 | >10 |
| A-124 | 0.0137 | >10 |
| A-126 | 0.0137 | 10 |
| A-127 | 0.0137 | 3.33 |
| A-128 | 0.0412 | 3.33 |
| A-130 | 0.123 | 3.33 |
| A-131 | 0.0412 | >10 |
| A-132 | 0.123 | 10 |
| A-133 | 0.0137 | >10 |
| A-134 | 0.0137 | 10 |
| A-135 | 0.0137 | 10 |
| A-136 | 0.0137 | 3.33 |
| A-138 | 0.0412 | 1.11 |
| A-139 | <0.000508 | 10 |
| A-140 | 0.0137 | 3.33 |
| A-141 | 0.0412 | 10 |
| A-142 | 0.0412 | 1.11 |
| A-143 | 0.0412 | 1.11 |
| A-144 | 0.0137 | >10 |
| A-145 | 0.0412 | >10 |

TABLE 45

| Compound No. | MAC (μg/ml) | $IC_{50}$-C (μg/ml) |
|---|---|---|
| A-146 | 0.0137 | >10 |
| A-147 | 0.123 | >10 |
| A-148 | 0.123 | 10 |
| A-149 | 0.123 | 3.33 |
| A-150 | 0.123 | 10 |
| A-151 | 0.37 | 10 |
| A-152 | 0.123 | >10 |
| A-153 | 0.0412 | >10 |
| A-154 | 0.0412 | >10 |
| A-155 | 0.00457 | 3.33 |
| A-157 | 0.0137 | >10 |
| A-158 | 0.0412 | >10 |
| A-159 | 0.0412 | 10 |
| A-160 | 0.0137 | >10 |
| A-161 | 0.0412 | >10 |
| A-162 | 0.123 | >10 |
| A-163 | 0.0137 | >10 |
| A-164 | 0.0137 | >10 |
| A-165 | 0.123 | 10 |
| A-166 | 0.123 | 10 |
| A-167 | 0.0137 | 10 |
| A-168 | 0.0412 | >10 |
| A-169 | 0.0412 | 10 |
| A-170 | <0.000508 | >10 |
| A-171 | 0.0137 | 10 |
| A-172 | 0.0137 | 10 |
| A-173 | 0.123 | 10 |
| A-174 | 0.37 | >10 |
| A-175 | 0.0137 | 3.33 |
| A-176 | 0.123 | 10 |
| A-177 | 0.0412 | 10 |
| A-178 | 0.0412 | 10 |
| A-179 | 0.0137 | 10 |
| A-180 | 0.00457 | 10 |
| A-181 | 0.0137 | 10 |
| A-182 | 0.0137 | 3.3 |
| A-183 | 0.00457 | 10 |

TABLE 45-continued

| Compound No. | MAC (µg/ml) | IC$_{50}$-C (µg/ml) |
|---|---|---|
| A-184 | 0.0412 | 10 |
| A-185 | 0.0137 | 10 |
| A-186 | 0.0412 | >10 |
| A-187 | 0.0137 | >10 |
| A-188 | 0.0137 | 10 |
| A-189 | 0.0412 | 10 |
| A-190 | 0.0412 | 10 |
| B-2 | 0.370 | 10 |
| D-1 | 1.11 | >10 |
| D-6 | 0.370 | >10 |
| D-8 | 0.0412 | >10 |
| D-21 | 0.37 | >10 |
| D-29 | 1.11 | >10 |
| D-30 | 1.11 | >10 |
| D-36 | 0.0412 | >10 |
| D-37 | 0.123 | >10 |
| D-41 | 1.11 | >10 |
| D-45 | 1.11 | 10 |
| G-1 | 0.370 | >10 |

Test Example 2 In Vitro Cell Growth Inhibition Test Cells and MTT Assay

Human squamous lung cancer RERF-RC-AI, human squamous lung cancer Ma44, human lung adenocarcinoma A549, human colon cancer HT29 and human pancreas cancer PANC-1 were used. All cell lines were cultured with Eagle's Modified Essential Medium (EMEM, supplemented with 10% fetal calf serum (FCS: Hyclone, USA) and 60 µg/ml Kanamycin (Meiji-seika, Japan) at 37° C. in a humidified incubator (5% CO$_2$). The cells were plated in 96-well microcultureplate. Twenty-four hours later, compound were added at the concentration from 10 µg/ml to 0.1 µg/ml with 2-fold dilution. MTT assay was performed 4 days later and IC$_{50}$ values were determined. The results were shown in Tables 46 to 49 in terms of concentration at ng/ml.

TABLE 46

| Compound No. | RERF-LC-AI | Ma44 | A549 | HT29 | PANC-1 |
|---|---|---|---|---|---|
| A-1 | 18 | 39 | 22 | 12 | 16 |
| A-2 | 9.0 | 22 | 17 | 15 | 15 |
| A-3 | 26 | 90 | 35 | 6.6 | 15 |
| A-5 | 200 | | 160 | 150 | |
| A-8 | 10 | | 12 | 8 | |
| A-9 | 25 | | 90 | 100 | |
| A-12 | 870 | | | 510 | |
| A-18 | 2.2 | | | | |
| A-19 | 20 | | | | |
| A-20 | 20 | | | | |
| A-21 | 20 | | | | |
| A-22 | 20 | | | | |
| A-23 | 7.8 | 25 | 41 | | |
| A-24 | 7.1 | 28 | 26 | | |
| A-25 | 7.8 | 31 | 32 | | |
| A-26 | 16 | 55 | 60 | | |
| A-27 | 79 | 1000 | 690 | | |
| A-33 | 4.0 | 8.7 | 12 | 7.1 | 7.6 |
| A-36 | 7.2 | 26 | | 15 | 14 |
| A-37 | 21 | 240 | | 30 | 25 |
| A-38 | 14 | 34 | | 23 | 28 |
| A-40 | | 71 | | 49 | |
| A-41 | | 65 | | 72 | |
| A-42 | 8.3 | 49 | | 11 | |
| A-44 | 6.1 | 18 | | 6.1 | 160 |
| A-46 | 140 | 1800 | | 320 | |
| A-49 | 1.6 | 3.2 | | 2.8 | |
| A-50 | 47 | 260 | | 90 | |
| A-51 | 12 | 88 | | 28 | |
| A-52 | | 110 | | 49 | 24 |

TABLE 46-continued

| Compound No. | RERF-LC-AI | Ma44 | A549 | HT29 | PANC-1 |
|---|---|---|---|---|---|
| A-56 | | 850 | 180 | | 85 |
| A-57 | | 25 | 14 | | 8.8 |
| A-60 | 4.0 | 12 | | | 3.9 |
| A-61 | 4.1 | 16 | | | 6.3 |
| A-62 | 7.8 | 24 | | | 17 |
| A-63 | 6.0 | 53 | | | 8.7 |
| A-64 | 13 | 86 | 34 | 15 | 30 |

TABLE 47

| Compound No. | RERF-LC-AI | Ma44 | A549 | HT29 | PANC-1 |
|---|---|---|---|---|---|
| A-65 | 1.4 | 90 | 2.8 | 1.4 | 2.1 |
| A-66 | 50 | 1800 | 36 | 67 | 170 |
| A-67 | 53 | 6100 | 83 | 83 | 340 |
| A-70 | 6.7 | 32 | 13 | 8.4 | 15 |
| A-71 | 77 | 310 | 720 | 93 | 180 |
| A-73 | 12 | 48 | 52 | 16 | 29 |
| A-74 | 8 | 12 | 34 | 10 | 17 |
| A-75 | 4.0 | 5.8 | 8.7 | 3.8 | 6.5 |
| A-76 | 8 | 100 | 20 | 8 | 16 |
| A-77 | 30 | 110 | 130 | 44 | 48 |
| A-78 | 17 | 52 | 63 | 21 | 37 |
| A-80 | 18 | 62 | 100 | 24 | 50 |
| A-81 | 9 | 32 | 23 | 7 | 16 |
| A-82 | 8 | 14 | 31 | 6 | 14 |
| A-84 | 180 | 410 | 440 | 380 | 300 |
| A-88 | 20 | 97 | 140 | 43 | 36 |
| A-89 | 16 | 860 | 150 | 50 | 49 |
| A-101 | | 210 | 790 | 52 | 77 |
| A-105 | | 91 | 110 | 64 | 86 |
| A-106 | | 86 | 82 | 43 | 56 |
| A-107 | | 55 | 65 | 36 | 52 |
| A-108 | | 29 | 27 | 22 | 27 |
| A-110 | 6 | 63 | 42 | 7.7 | |
| A-111 | 17 | 400 | 97 | 35 | |
| A-112 | 23 | 2000 | 380 | 64 | |
| A-113 | 27 | 1200 | 620 | 76 | |
| A-114 | 29 | 830 | 320 | 45 | |
| A-115 | 430 | 5800 | 4600 | 65 | |
| A-116 | 620 | 4200 | 3800 | 72 | |
| A-117 | 160 | 8600 | 1100 | 17 | |
| A-119 | 23 | 200 | 1200 | 100 | 68 |
| A-120 | 24 | 100 | 1300 | 23 | 55 |
| A-121 | 20 | 20 | 58 | 20 | 20 |
| A-122 | 140 | 300 | 2100 | 89 | 210 |
| A-123 | 34 | 90 | 150 | 41 | |
| A-124 | 22 | 24 | 26 | 28 | |
| A-126 | 12 | 170 | 28 | 14 | |
| A-127 | 15 | 17 | 28 | 18 | 17 |
| A-128 | 36 | 44 | 47 | 42 | 26 |

TABLE 48

| Compound No. | RERF-LC-AI | Ma44 | A549 | HT29 | PANC-1 |
|---|---|---|---|---|---|
| A-129 | 170 | 330 | 430 | 300 | 210 |
| A-130 | 23 | 39 | 74 | 29 | 18 |
| A-131 | 15 | 28 | 30 | 25 | 28 |
| A-132 | 50 | 77 | 180 | 39 | 81 |
| A-133 | 10 | 15 | 47 | 68 | 15 |
| A-134 | 16 | 26 | 49 | 13 | 25 |
| A-135 | 12 | 16 | 52 | 10 | 17 |
| A-136 | 12 | 16 | 31 | 11 | 16 |
| A-138 | 43 | 40 | 46 | 30 | 26 |
| A-139 | 13 | 14 | 13 | 8 | 7 |
| A-140 | 15 | 47 | 22 | 13 | 12 |
| A-141 | 16 | 85 | 51 | 32 | 21 |
| A-142 | 18 | 21 | 38 | 32 | 15 |
| A-143 | 23 | 33 | 52 | 24 | 20 |
| A-144 | 7 | 31 | 19 | 6 | 16 |
| A-145 | 5 | 32 | 90 | 7 | 14 |

TABLE 48-continued

| Compound No. | RERF-LC-AI | Ma44 | A549 | HT29 | PANC-1 |
|---|---|---|---|---|---|
| A-146 | 11 | 52 | 180 | 14 | 24 |
| A-147 | 8 | 71 | 100 | 8 | 18 |
| A-148 | 11 | 86 | 490 | 16 | 15 |
| A-149 | 26 | 85 | 25 | 34 | 41 |
| A-150 | 16 | 140 | 5 | 31 | 37 |
| A-151 | 13 | 160 | 70 | 20 | 24 |
| A-152 | 6 | 39 | 69 | 82 | 13 |
| A-153 | 11 | 89 | 67 | 15 | 22 |
| A-154 | 8 | 40 |  | 12 | 18 |
| A-155 | 6 | 9 |  | 80 | 9 |
| A-156 | 16 | 72 |  | 23 | 25 |
| A-157 | 5 | 44 |  | 8 | 15 |
| A-158 | 7 | 32 |  | 25 | 30 |
| A-161 | 6.8 | 7.1 | 12 | 5.5 | 5.3 |
| A-162 | 8.5 | 14 | 28 | 6.7 | 9.3 |
| A-165 | 25 | 55 | 95 | 52 | 50 |
| A-166 | 16 | 49 | 56 | 33 | 28 |
| A-167 | 3.2 | 25 | 12 | 6.1 | 6 |
| A-168 | 2.8 | 17 | 12 | 5.5 | 5.9 |
| A-169 | 21 | 50 | 41 | 27 | 25 |
| A-170 | 2.7 | 5.4 | 14 | 7.7 | 6.5 |
| A-171 | 4 | 13 | 12 | 6.4 | 6 |

TABLE 49

| Compound No. | RERF-LC-AI | Ma44 | A549 | HT29 | PANC-1 |
|---|---|---|---|---|---|
| A-172 | 1.5 | 3.8 | 7.5 | 3.3 | 3.1 |
| A-173 | 3.7 | 7.2 | 17 | 6 | 7.2 |
| A-174 | 6.7 | 76 | 32 | 12 | 14 |
| A-175 | 5.3 | 15 | 17 | 10 | 10 |
| A-176 | 3.2 | 18 | 12 | 6 | 5.6 |
| A-177 | 2 | 4.3 | 8.2 | 3.7 | 3.8 |
| A-178 | 3.6 | 24 | 14 | 6.7 | 5 |
| A-179 | 2 | 2.6 | 14 | 6.3 | 1.8 |
| A-180 | 8 | 16 | 14 | 12 | 8.1 |
| A-181 | 5.1 | 6.5 | 8.7 | 6.1 | 5.7 |
| A-182 | 5.6 | 16 | 14 | 11 | 7.3 |
| A-183 | 1.3 | 2.1 | 3.9 | 2 | 2.6 |
| A-184 | 2.7 | 16 | 10 | 7.7 | 3.2 |
| A-185 | 2.9 | 6.2 | 13 | 6.4 | 4.1 |
| A-186 | 14 | 57 | 48 | 14 | 17 |
| A-187 | 12 | 17 | 25 | 13 | 14 |
| A-188 | 12 | 16 | 52 | 10 | 17 |
| A-189 | 16 | 85 | 51 | 32 | 21 |
| D-2 |  | 32 |  | 13 |  |
| D-6 | 37 | 320 | 330 | 39 | 85 |
| D-7 | 83 | 5200 | 3200 | 180 | 2400 |
| D-8 | 12 | 36 | 27 | 30 | 13 |
| D-6 | 37 | 320 | 330 | 39 | 85 |
| D-7 | 83 | 5200 | 3200 | 180 | 2400 |
| D-8 | 12 | 36 | 27 | 30 | 13 |
| D-21 | 13 | 350 | 49 | 16 |  |
| D-29 | 110 | 520 | 220 | 90 |  |
| D-30 | 46 | 2400 | 100 | 33 |  |
| D-32 | 13 | 3100 | 3500 | 13 |  |
| D-35 | 2500 | 1500 | 4600 | 25 |  |
| D-36 | 23 | 65 | 32 | 49 |  |
| D-37 | 11 | 24 | 28 | 15 | 13 |
| D-41 | 24 | 55 | 70 | 40 | 49 |
| D-42 | 82 | 380 | 570 | 71 | 170 |
| D-43 | 210 | 200 | 270 | 100 | 100 |
| D-45 | 62 | 740 | 6.1 | 38 | 120 |
| G-1 | 46 | 56 | 63 | 52 | 51 |

Test Example 3 Evaluation of in Vivo Antitumor Efficacy

Murine colon cancer Colon 26, human lung cancer RERF-LC-AI and human lung cancer Ma44 were used. Murine- and human-derived tumor cells were maintained by serial transplantation in Balb/c and Balb/c nude mice, respectively. After tumor implantation, compound A-42 suspended in 5% methylcellulose solution were orally administered daily for 14 days. Tumor size (short diameter and long diameter) was scored throughout the experiment and tumor volume was calculated. Antitumor efficacy was evaluated as growth inhibition which was estimated by Treated/Control ratio and shown as % inhibition. Growth inhibition of compound A-42 at 30 mg/kg for 14 days were 70% ($P<0.01$), 74% ($P<0.01$) and 66% ($P<0.01$) against Colon 26 and RERF-LC-AI and Ma44, respectively.

FORMULATION EXAMPLE

Formulation Example 1

Granules are prepared using the following ingredients.

| Ingredients | The compound represented by the formula (I) | 10 mg |
|---|---|---|
|  | Lactose | 700 mg |
|  | Corn starch | 274 mg |
|  | HPC-L | 16 mg |
|  |  | 1000 mg |

The compound represented by the formula (I) and lactose were made pass through a 60 mesh sieve. Corn starch was made pass through a 120 mesh sieve. They were mixed by a twin shell blender. An aqueous solution of HPC-L (low mucosity hydroxypropylcellulose) was added to the mixture and the resulting mixture was kneaded, granulated (by the extrusion with pore size 0.5 to 1 mm mesh), and dried. The dried granules thus obtained were sieved by a swing sieve (12/60 mesh) to yield the granules.

Formulation 2

Powders for filling capsules are prepared using the following ingredients.

| Ingredients | The compound represented by the formula (I) | 10 mg |
|---|---|---|
|  | Lactose | 79 mg |
|  | Corn starch | 10 mg |
|  | Magnesium stearate | 1 mg |
|  |  | 100 mg |

The compound represented by the formula (I) and lactose were made pass through a 60 mesh sieve. Corn starch was made pass through a 120 mesh sieve. These ingredients and magnesium stearate were mixed by a twin shell blender. 100 mg of the 10-fold trituration was filled into a No. 5 hard gelatin capsule.

Formulation 3

Granules for filling capsules are prepared using the following ingredients.

| Ingredients | The compound represented by the formula (I) | 15 mg |
|---|---|---|
|  | Lactose | 90 mg |
|  | Corn starch | 42 mg |
|  | HPC-L | 3 mg |
|  |  | 150 mg |

The compound represented by the formula (I) and lactose were made pass through a 60 mesh sieve. Corn starch was made pass through a 120 mesh sieve. After mixing them, an aqueous solution of HPC-L was added to the mixture and the resulting mixture was kneaded, granulated, and dried. After the dried granules were lubricated, 150 mg of that were filled into a No. 4 hard gelatin capsule.

Formulation 4

Tablets are prepared using the following ingredients.

| Ingredients | The compound represented by the formula (I) | 10 mg |
| --- | --- | --- |
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, niicrocrystal cellulose, and CMC-Na (carboxymethylcellulose sodium salt) were made pass through a 60 mesh sieve and then mixed. The resulting mixture was mixed with magnesium stearate to obtain the mixed powder for the tablet formulation. The mixed powder was compressed to yield tablets of 150 mg.

Industrial Applicability

The pyrimidine derivatives of the present invention have an inhibitory activity against a signal derived from Ras oncogene products, whereby they are effective for solid cancer having high frequency ras activation such as pancreatic cancer, colon cancer, and lung cancer.

What is claimed is:

1. A compound represented by the formula (I):

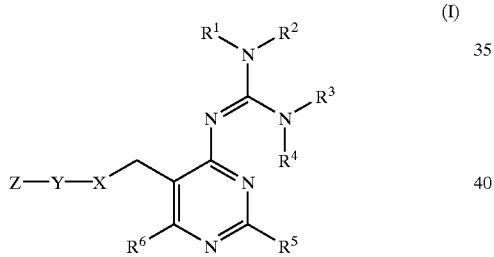

(I)

wherein, $R^1$, $R^2$, $R^3$ and $R^4$ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, or acyl; or $R^1$ and $R^2$, $R^3$ and $R^4$, and $R^2$ and $R^3$ each taken together with the adjacent nitrogen atom form the same or different 3- to 6-membered ring optionally containing O, S, or N, provided that $R^1$ and $R^2$, and $R^3$ and $R^4$ do not form a ring when $R^2$ and $R^3$ taken together form a ring;

$R^5$ and $R^6$ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl, optionally substituted heteroaryl, optionally substituted aryl alkenyl, or optionally substituted alkenyl;

an ester derivative thereof, an acyloxy derivative thereof or an amide derivative thereof, pharmaceutically acceptable salts thereof, or solvates thereof.

2. A compound represented by the formula (II):

(II)

wherein, $R^8$, $R^9$, $R^{10}$, and $R^{11}$ are each independently hydrogen atom, optionally substituted alkyl, alkenyl, alkynyl, optionally substituted aryl, optionally substituted heteroaryl, optionally substituted aralkyl, a non-aromatic heterocyclic group, or acyl;

W is —O—, —S—, or —N($R^A$)— wherein $R^A$ is hydrogen atom or optionally substituted alkyl;

$R^5$, $R^6$, X and Z are as defined in claim 1, an ester derivative thereof, an acyloxy derivative thereof or an amide derivative thereof, pharmaceutically acceptable salts thereof, or solvates thereof.

3. A compound represented by the formula (III):

(III)

wherein $R^5$, $R^6$, $R^8$, $R^9$, $R^{10}$, $R^{11}$, and Z are as defined in claim 2, an ester derivative thereof, an acyloxy derivative thereof or an amide derivative thereof, pharmaceutically acceptable salts thereof, or solvates thereof.

4. A compound represented by the formula (IV):

(IV)

wherein $R^{12}$ is hydrogen atom or alkyl;

V is optionally substituted aryl;

$R^8$, $R^9$, $R^{10}$, and $R^{11}$ are as defined in claim 2, an ester derivative thereof, an acyloxy derivative thereof or an amide derivative thereof, pharmaceutically acceptable salts thereof, or solvates thereof.

5. The compound of claim 1, an ester derivative thereof, an acyloxy derivative thereof or an amide derivative thereof, pharmaceutically acceptable salts thereof, solvates thereof, wherein $R^1$, $R^2$, $R^3$, and $R^4$ are each independently hydrogen atom, optionally substituted alkyl, alkenyl, alkynyl, or acyl.

6. The compound of claim 1, an ester derivative thereof, an acyloxy derivative thereof or an amide derivative thereof, pharmaceutically acceptable salts thereof, or solvates thereof, wherein $R^8$, $R^9$, $R^{10}$, and $R^{11}$ are each independently hydrogen atom, optionally substituted alkyl, alkenyl, alkynyl, or acyl.

7. A pharmaceutical composition comprising a compound of formula 1 as described in claim 1 and a pharmaceutically acceptable carrier.

8. A method of treating a patient suffering from cancer comprising administering an effective amount of an antitumor agent to a subject comprising a compound of formula (I):

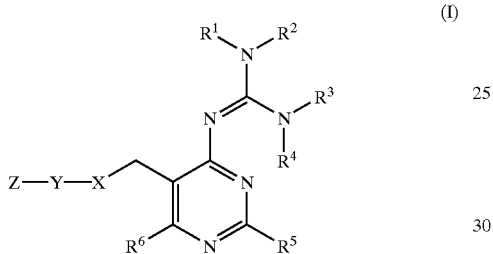

wherein, $R^1$, $R^2$, $R^3$ and $R^4$ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, or acyl; or $R^1$ and $R^2$, $R^3$ and $R^4$, and $R^2$ and $R^3$ each taken together with the adjacent nitrogen atom form the same or different 3- to 6-membered ring optionally containing O, S, or N, provided that $R^1$ and $R^2$, and $R^3$ and $R^4$ do not form a ring when $R^2$ and $R^3$ taken together form a ring;

$R^5$ and $R^6$ are each independently hydrogen atom, optionally substituted alkyl, optionally substituted alkenyl, optionally substituted alkynyl, optionally substituted alkyloxy, alkylthio, optionally gubetituted alkyloxycarbonyl, optionally substituted aryl, optionally substituted heteroaryl, halogen, hydroxy, mercapto, optionally substituted amino, carboxy, cyano, or nitro;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl, optionally substituted heteroaryl, optionally substituted aryl alkenyl, or optionally substituted alkenyl;

and a pharmaceutically acceptable carrier.

9. A method of treating a patient suffering from cancer comprising administering an effective amount of a cytostatic agent to a subject comprising a compound of formula

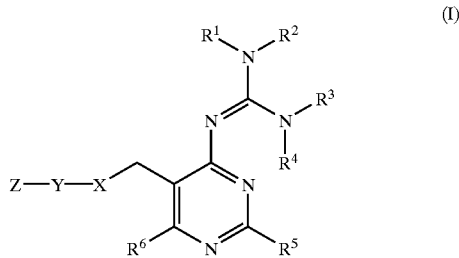

wherein, $R^1$, $R^2$, $R^3$ and $R^4$ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, or acyl; or $R^1$ and $R^2$, $R^3$ and R4, and $R^2$ and $R^3$ each taken together with the adjacent nitrogen atom form the same or different 3- to 6-membered ring optionally containing O, S, or N, provided that $R^1$ and $R^2$, and $R^3$ and $R^4$ do not form a ring when $R^2$ and $R^3$ taken together form a ring;

$R^5$ and $R^6$ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl, optionally substituted heteroaryl, optionally substituted aryl alkenyl, or optionally substituted alkenyl;

and a pharmaceutically acceptable carrier.

10. A method of inhibiting a signal derived from Ras oncogene products comprising administering to a patient an effective amount of the composition of claim 7 and a pharmaceutically acceptable carrier.

11. A method of alleviating the pathological effects of cancer comprising administering to a patient an effective amount of the composition of claim 7 and a pharmaceutically acceptable carrier.

12. The method of any one of claims 10 or 11 wherein the agent is administered in an oral or parental dose form.

13. The method of any one of claims 10 or 11 wherein the composition is administered in an oral or parental dose form.

* * * * *